United States Patent
Py

(10) Patent No.: US 7,490,639 B2
(45) Date of Patent: *Feb. 17, 2009

(54) DEVICE WITH NEEDLE PENETRABLE AND LASER RESEALABLE PORTION AND RELATED METHOD

(75) Inventor: Daniel Py, Stamford, CT (US)

(73) Assignee: Medical Instill Technologies, Inc., New Milford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/949,087

(22) Filed: Dec. 3, 2007

(65) Prior Publication Data

US 2008/0072996 A1 Mar. 27, 2008

Related U.S. Application Data

(60) Continuation of application No. 11/879,485, filed on Jul. 16, 2007, which is a continuation of application No. 11/408,704, filed on Apr. 21, 2006, now Pat. No. 7,243,689, which is a continuation of application No. 10/766,172, filed on Jan. 28, 2004, now Pat. No. 7,032,631, which is a continuation-in-part of application No. 10/694,364, filed on Oct. 27, 2003, now Pat. No. 6,805,170, which is a continuation of application No. 10/393,966, filed on Mar. 21, 2003, now Pat. No. 6,684,916, which is a division of application No. 09/781,846, filed on Feb. 12, 2001, now Pat. No. 6,604,561.

(60) Provisional application No. 60/484,204, filed on Jun. 30, 2003, provisional application No. 60/442,526, filed on Jan. 28, 2003, provisional application No. 60/182,139, filed on Feb. 11, 2000.

(51) Int. Cl.
B65B 1/04 (2006.01)
B65B 51/10 (2006.01)
A61B 19/00 (2006.01)
B65D 39/00 (2006.01)

(52) U.S. Cl. ............... 141/329; 141/2; 141/82; 141/85; 604/415; 215/247; 53/477

(58) Field of Classification Search .............. 141/2, 141/18, 59, 82, 85, 94, 284, 285, 329; 53/403, 53/440, 442, 467, 471, 477, 478; 215/247, 215/274, 280; 604/256, 414, 415, 537
See application file for complete search history.

(56) References Cited

U.S. PATENT DOCUMENTS 2,503,147 A 4/1950 Applezweig ............... 226/116
(Continued)

FOREIGN PATENT DOCUMENTS

CA 1123792 5/1982 ............... 210/49
(Continued)

*Primary Examiner*—Timothy L Maust
(74) *Attorney, Agent, or Firm*—McCarter & English, LLP

(57) ABSTRACT

A device defining a chamber for receiving a substance and a thermoplastic portion in fluid communication with the chamber is provided along with a method of filling and sealing the substance within the chamber. The thermoplastic portion defines a penetrable region that is penetrable by a filling member and is heat resealable to hermetically seal an aperture therein by applying laser radiation at a predetermined wavelength and power. The thermoplastic portion comprises a thermoplastic body defining a predetermined wall thickness and includes a styrene block copolymer, an olefin and a predetermined amount of pigment allowing the body to absorb laser radiation at the predetermined wavelength, substantially prevent the passage of radiation through the predetermined wall thickness, and hermetically seal the aperture in the penetrable region in a predetermined time period. The body includes a predetermined amount of lubricant that reduces friction forces at an interface of the filling member and body during penetration thereof.

21 Claims, 56 Drawing Sheets

U.S. PATENT DOCUMENTS

| | | | |
|---|---|---|---|
| 2,667,986 A | 2/1954 | Perelson | 215/48 |
| 3,092,278 A | 6/1963 | Järnhäll | 215/37 |
| 3,136,440 A | 6/1964 | Krug et al. | 215/47 |
| 3,278,063 A | 10/1966 | Kranzhoff | 215/38 |
| 3,340,671 A | 9/1967 | Loo | 53/37 |
| 3,392,859 A | 7/1968 | Fischer | 215/39 |
| 3,424,329 A | 1/1969 | Hersherg et al. | 215/37 |
| 3,685,248 A | 8/1972 | Godelaine | 53/37 |
| 3,811,591 A | 5/1974 | Novitch | 215/12 R |
| 4,048,255 A | 9/1977 | Hillier et al. | 260/859 R |
| 4,250,611 A | 2/1981 | Wong | 29/460 |
| 4,366,912 A | 1/1983 | Matakura et al. | 215/247 |
| 4,390,111 A | 6/1983 | Robbins et al. | 220/259 |
| 4,444,330 A | 4/1984 | Kasai et al. | 215/247 |
| 4,499,148 A | 2/1985 | Goodale et al. | 428/447 |
| 4,664,275 A | 5/1987 | Kasai et al. | 215/247 |
| 4,682,703 A | 7/1987 | Kasai et al. | 215/247 |
| 4,703,781 A | 11/1987 | Meyer et al. | 141/5 |
| 4,815,619 A | 3/1989 | Turner et al. | 215/248 |
| 4,834,152 A | 5/1989 | Howson et al. | 141/268 |
| 4,842,028 A | 6/1989 | Kaufman et al. | 141/114 |
| 4,910,435 A | 3/1990 | Wakalopulos | 315/111.31 |
| 5,009,654 A | 4/1991 | Minshall et al. | 604/410 |
| 5,031,675 A | 7/1991 | Lindgren | 141/291 |
| 5,038,839 A | 8/1991 | Morimoto et al. | 141/83 |
| 5,060,659 A | 10/1991 | Cook et al. | 600/577 |
| 5,085,332 A | 2/1992 | Gettig et al. | 215/249 |
| 5,088,612 A | 2/1992 | Storar et al. | 215/247 |
| 5,088,995 A | 2/1992 | Packard et al. | 604/415 |
| 5,129,212 A | 7/1992 | Duffey et al. | 53/426 |
| 5,341,854 A | 8/1994 | Zezulka et al. | 141/1 |
| 5,390,469 A | 2/1995 | Shimizu et al. | 53/53 |
| 5,411,065 A | 5/1995 | Meador et al. | 141/1 |
| 5,414,267 A | 5/1995 | Wakalopulos | 250/492.3 |
| 5,484,566 A | 1/1996 | Gabbard | 264/250 |
| 5,496,302 A | 3/1996 | Minshall et al. | 604/410 |
| RE35,203 E | 4/1996 | Wakalopulos | 250/492.3 |
| 5,514,339 A | 5/1996 | Leopardi et al. | 422/99 |
| 5,549,141 A | 8/1996 | Meador et al. | 141/1 |
| 5,612,588 A | 3/1997 | Wakalopulos | 313/420 |
| 5,641,004 A | 6/1997 | Py | 141/3 |
| 5,673,535 A | 10/1997 | Jagger | 53/282 |
| 5,702,019 A | 12/1997 | Grimard | 215/301 |
| 5,816,772 A | 10/1998 | Py | 414/786 |
| 5,842,321 A | 12/1998 | Jones | 53/21 |
| 5,909,032 A | 6/1999 | Wakalopulos | 250/492.3 |
| 5,971,181 A | 10/1999 | Niedospial, Jr. et al. | 215/247 |
| 6,021,824 A | 2/2000 | Larsen et al. | 141/329 |
| 6,050,435 A | 4/2000 | Bush et al. | 215/250 |
| 6,068,150 A | 5/2000 | Mitchell et al. | 215/247 |
| 6,140,657 A | 10/2000 | Wakalopulos et al. | 250/492.3 |
| 6,168,037 B1 | 1/2001 | Grimard | 215/301 |
| 6,199,350 B1 | 3/2001 | Brechel et al. | 53/510 |
| 6,308,494 B1 | 10/2001 | Yuyama et al. | 53/131.3 |
| RE37,471 E | 12/2001 | Jagger | 53/282 |
| 6,343,711 B1 | 2/2002 | Coughlin | 221/217 |
| 6,364,864 B1 | 4/2002 | Mohiuddin et al. | 604/410 |
| 6,382,441 B1 | 5/2002 | Carano | 215/247 |
| 6,385,943 B2 | 5/2002 | Yuyama et al. | 53/131.4 |
| 6,604,561 B2 * | 8/2003 | Py | 141/329 |
| 7,032,631 B2 * | 4/2006 | Py | 141/82 |
| 7,243,689 B2 * | 7/2007 | Py | 141/2 |
| 2001/0041872 A1 | 11/2001 | Paul, Jr. | 604/167.04 |
| 2002/0006353 A1 | 1/2002 | Bilstad et al. | 422/22 |
| 2002/0010995 A1 | 1/2002 | Thibault et al. | 29/511 |
| 2002/0018731 A1 | 2/2002 | Bilstad et al. | 422/1 |
| 2002/0029022 A1 | 3/2002 | Naritomi et al. | 604/256 |
| 2002/0131902 A1 | 9/2002 | Levy | 422/99 |
| 2002/0172615 A1 | 11/2002 | Woodsworth et al. | 422/22 |
| 2003/0156973 A1 | 8/2003 | Bilstad et al. | 422/22 |

FOREIGN PATENT DOCUMENTS

| | | |
|---|---|---|
| FR | 2509689 | 7/1981 |
| GB | 500534 | 2/1939 |
| GB | 984149 | 2/1965 |
| GB | 2364700 | 2/2002 |

* cited by examiner

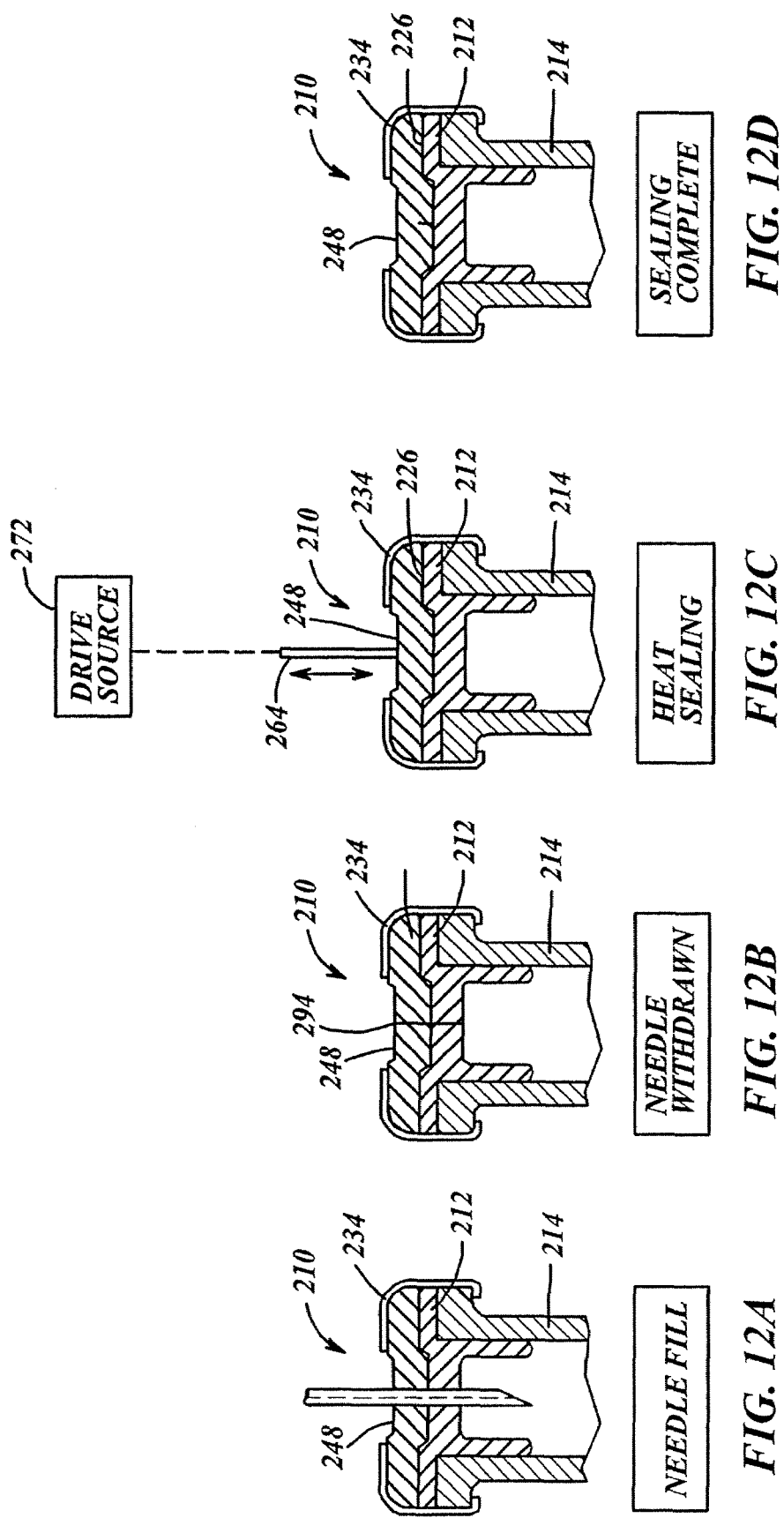

NEEDLE FILL

NEEDLE WITHDRAWN

HEAT SEALING

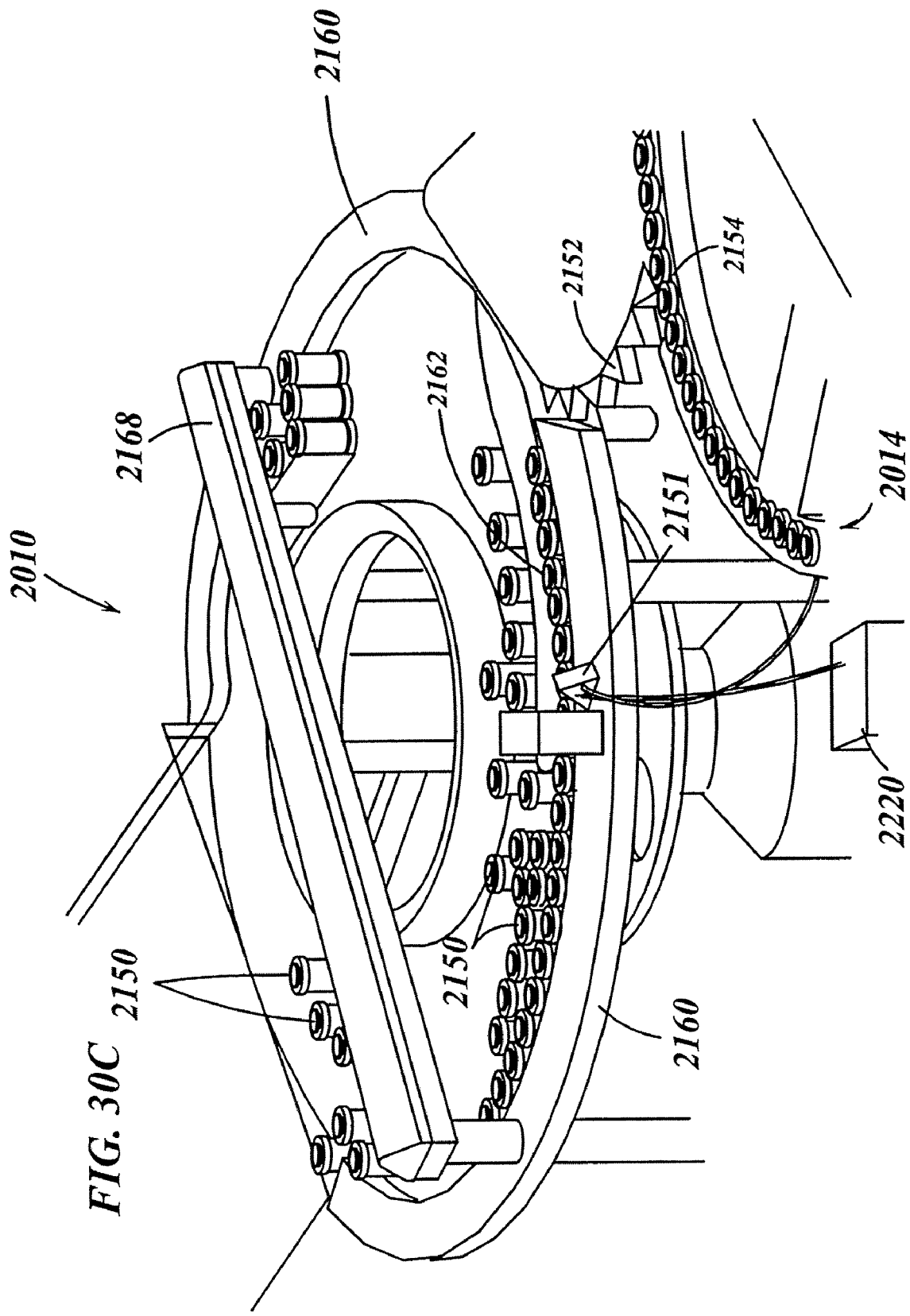

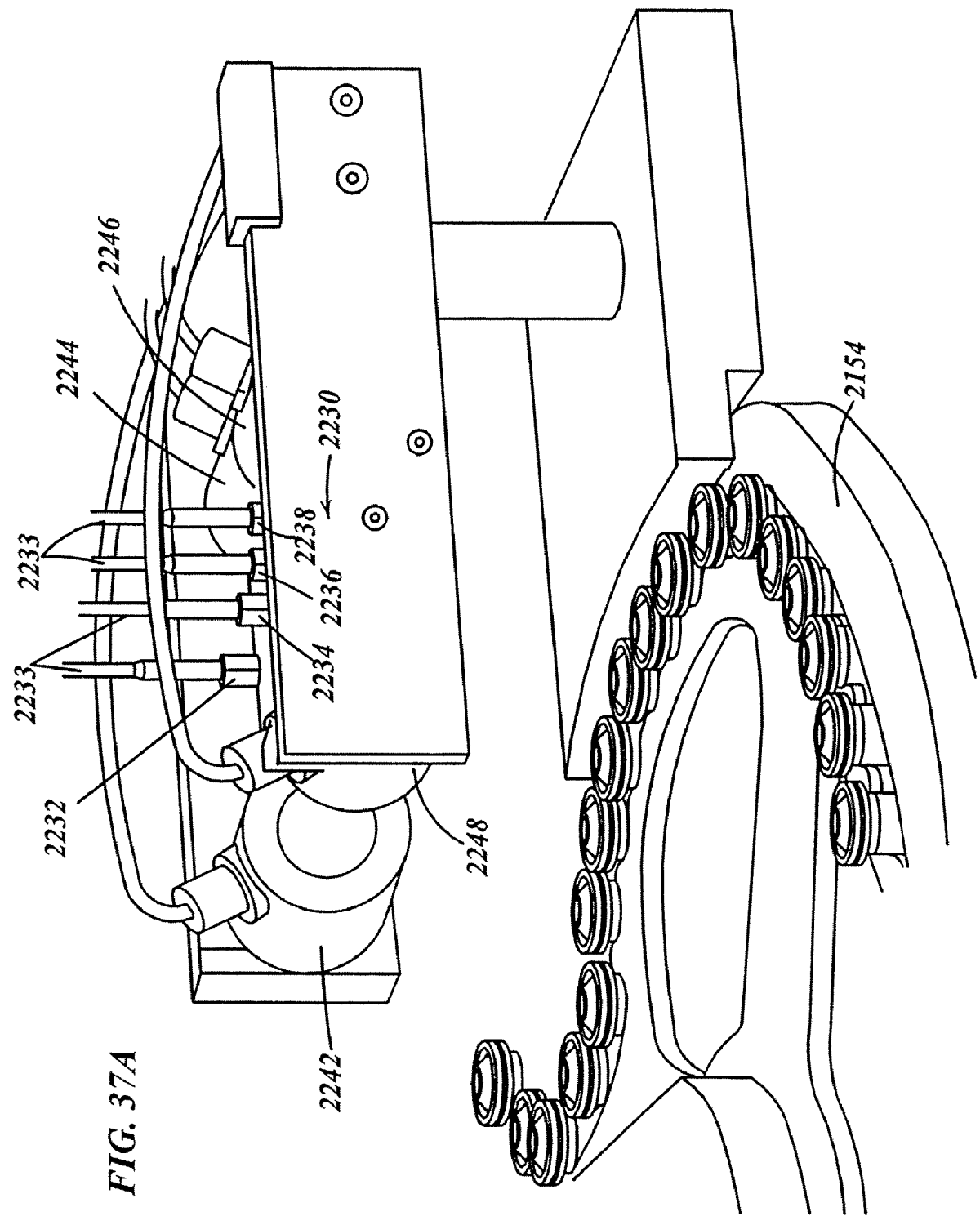

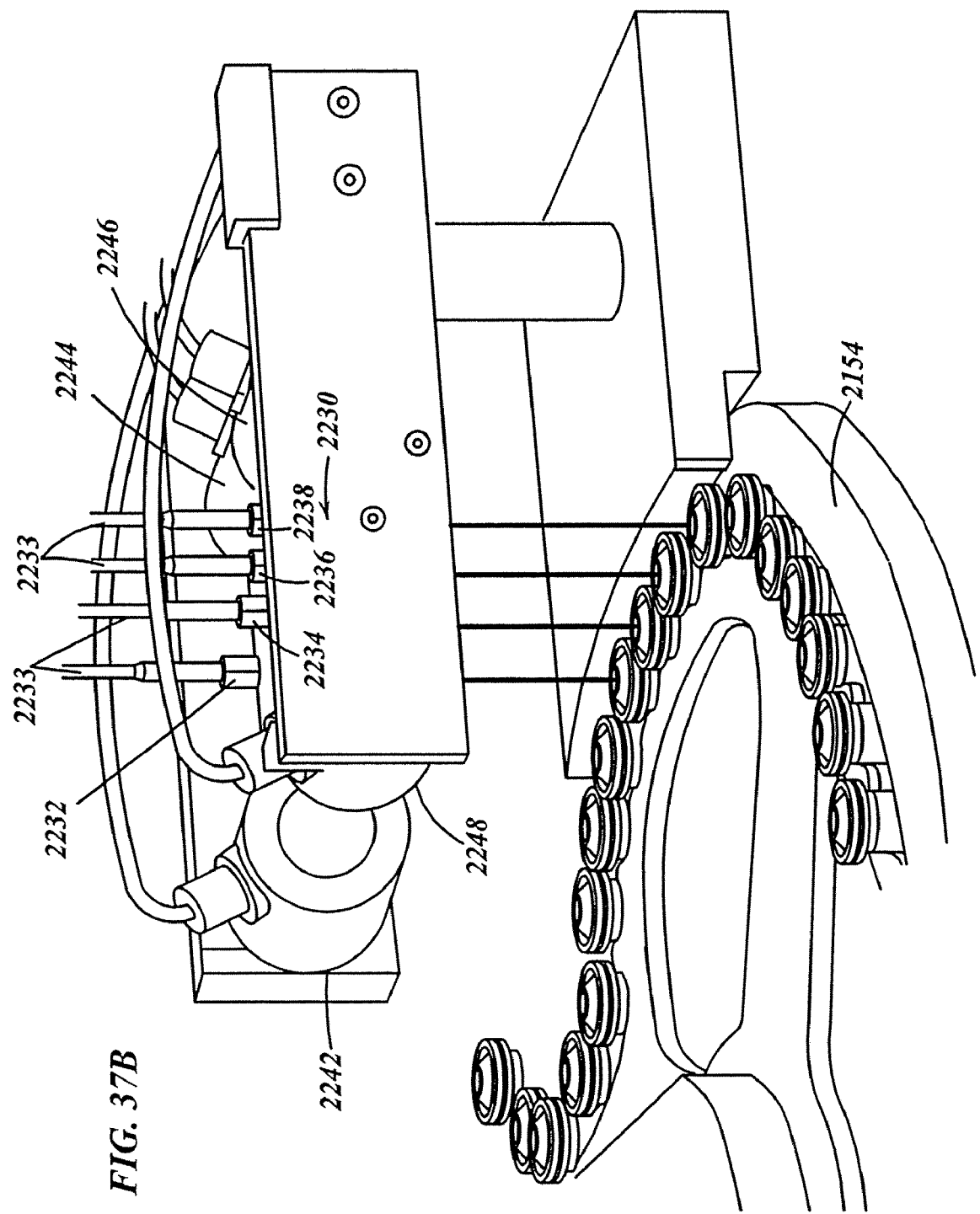

DEVICE WITH NEEDLE PENETRABLE AND LASER RESEALABLE PORTION AND RELATED METHOD

CROSS-REFERENCE TO RELATED APPLICATIONS

This patent application is a continuation of U.S. patent application Ser. No. 11/879,485, filed Jul. 16, 2007, entitled "Device with Needle Penetrable and Laser Resealable Portion and Related Method", which is a continuation of similarly titled U.S. patent application Ser. No. 11/408,704, filed Apr. 21, 2006, now U.S. Pat. No. 7,243,689, which is a continuation of U.S. patent application Ser. No. 10/766,172, filed Jan. 28, 2004, entitled "Medicament Vial Having a Heat-Sealable Cap, and Apparatus and Method for Filling the Vial", now U.S. Pat. No. 7,032,631, which is a continuation-in-part of similarly titled U.S. patent application Ser. No. 10/694,364, filed Oct. 27, 2003, now U.S. Pat. No. 6,805,170, which is a continuation of similarly titled U.S. patent application Ser. No. 10/393,966, filed Mar. 21, 2003, now U.S. Pat. No. 6,684,916, which is a divisional of similarly titled U.S. patent application Ser. No. 09/781,846, filed Feb. 12, 2001, now U.S. Pat. No. 6,604,561, which, in turn, claims the benefit of similarly titled U.S. Provisional Application Ser. No. 60/182,139, filed Feb. 11, 2000. Further, parent application Ser. No. 10/766,172 claims priority on similarly titled U.S. Provisional Patent Application No. 60/442,526, filed Jan. 28, 2003, and similarly titled U.S. Provisional Patent Application No. 60/484,204, filed Jun. 30, 2003. The foregoing applications and patents are hereby expressly incorporated by reference in their entireties as part of the present disclosure.

FIELD OF THE INVENTION

The present invention relates to heat-sealable caps or stoppers for vials or other containers for storing medicaments or other substances for use where a sterile medicament or other substance must be maintained following temporary introduction of a needle through the cap or stopper, and to apparatus and methods for filling such vials or other containers.

BACKGROUND OF THE INVENTION

A typical medicament dispenser includes a body defining a storage chamber, a fill opening in fluid communication with the body, and a stopper or cap for sealing the fill opening after filling the storage chamber to hermetically seal the medicament within the dispenser. In order to fill such prior art dispensers with a sterile fluid or other substance, such as a medicament, it is typically necessary to sterilize the unassembled components of the dispenser, such as by autoclaving the components and/or exposing the components to gamma radiation. The sterilized components then must be filled and assembled in an aseptic isolator of a sterile filling machine. In some cases, the sterilized components are contained within multiple sealed bags or other sterile enclosures for transportation to the sterile filling machine. In other cases, the sterilization equipment is located at the entry to the sterile filling machine. In a filling machine of this type, every component is transferred sterile into the isolator, the storage chamber of the vial is filled with the fluid or other substance, the sterilized stopper is assembled to the vial to plug the fill opening and hermetically seal the fluid or other substance in the vial, and then a crimping ring is assembled to the vial to secure the stopper thereto.

One of the drawbacks associated with such prior art dispensers, and processes and equipment for filling such dispensers, is that the filling process is time consuming, and the processes and equipment are expensive. Further, the relatively complex nature of the filling processes and equipment can lead to more defectively filled dispensers than otherwise desired. For example, typically there are at least as many sources of failure as there are components. In many cases, there are complex assembly machines for assembling the vials or other dispensers that are located within the aseptic area of the filling machine that must be maintained sterile. This type of machinery can be a significant source of unwanted particles. Further, such isolators are required to maintain sterile air within the barrier enclosure. In closed barrier systems, convection flow is inevitable and thus laminar flow, or substantially laminar flow, cannot be achieved. When operation of an isolator is stopped, a media fill test may have to be performed which can last for several, if not many days, and can lead to repeated interruptions and significant reductions in production output for the pharmaceutical or other product manufacturer that is using the equipment. In order to address such production issues, government-imposed regulations are becoming increasingly sophisticated and are further increasing the cost of already-expensive isolators and like filling equipment. On the other hand, governmental price controls for injectables and vaccines, including, for example, preventative medicines, discourage such major financial investments. Accordingly, there is a concern that fewer companies will be able to afford such increasing levels of investment in sterile filling machines, thus further reducing competition in the injectable and vaccine marketplaces.

In order to address these and other concerns, the present inventor has determined that it would be desirable to manufacture and fill vials by first assembling the cap to the vial, sterilizing the assembled cap and vial, such as by irradiation, and then filling the assembled vial by inserting a needle or like injection member through the cap and introducing the medicament through the needle into the sterilized vial. One of the drawbacks associated with this approach, however, is that when the needle or like injection member is inserted through the cap and then withdrawn, it leaves a tiny hole in the cap. The material of the cap is resilient in order to reduce the diameter of the hole, and therefore the hole is usually small enough to keep the medicament from leaking out. However, the hole typically is not small enough to prevent air or other gases from passing through the hole and into the vial, and therefore such holes can allow the medicament to become contaminated or spoiled.

It has been a practice in the pharmaceutical fields to add preservatives to medicaments, such as vaccines, in order to prevent spoilage of the medicaments upon exposure to air or other possible contaminants. Certain preservatives, however, have been determined to cause undesirable effects on patients. Consequently, many medicaments, including vaccines, are preservative free. These preservative-free medicaments, and particularly preservative-free vaccines, are subject to contamination and/or spoilage if contained within a vial wherein the cap has a needle hole as described above.

Accordingly, it is an object of the present invention to overcome one or more of the above-described drawbacks and disadvantages of the prior art.

SUMMARY OF THE INVENTION

In accordance with a first aspect, the present invention is directed to a device including a needle penetrable and laser resealable portion that is pierceable with a needle to form a needle aperture therethrough to fill a chamber of the device with a predetermined substance through the needle, and is laser resealable to hermetically seal the needle aperture by applying laser radiation at a predetermined wavelength and power thereto. The needle penetrable and laser resealable portion defines a predetermined wall thickness in an axial direction thereof, and includes a thermoplastic that substantially prevents the formation of particles released into the chamber from the needle penetrable and laser resealable portion during penetration by and withdrawal of the needle. The thermoplastic includes a predetermined amount of pigment that allows the thermoplastic to substantially absorb laser radiation at the predetermined wavelength, substantially prevent the passage of radiation through the predetermined wall thickness thereof, and hermetically seal a needle aperture formed in the needle penetration region thereof in a predetermined time period of less than approximately 2 seconds.

In one embodiment, the thermoplastic includes an olefin within the range of about 3% to about 20% by weight, a styrene block copolymer within the range of about 80% to about 97% by weight, and a lubricant. In one embodiment, the thermoplastic includes (i) a first polymeric material in an amount within the range of about 80% to about 97% by weight and defining a first elongation, (ii) a second polymeric material in an amount within the range of about 3% to about 20% by weight and defining a second elongation that is less than the first elongation of the first material, and (iii) a lubricant in an amount that reduces friction forces at an interface of the needle and body. In one such embodiment, the first material is a styrene block copolymer and the second material is an olefin. In one embodiment, the predetermined amount of pigment is within the range of about 0.3% to about 0.6% by weight.

In accordance with another aspect, the needle penetrable and laser resealable portion includes (i) an underlying portion formed of a first material compatible with the predetermined substance and defining a substance-exposed surface exposed to the predetermined substance within the device; and (ii) a resealable portion overlying the underlying portion, wherein the resealable portion is penetrable by the needle for introducing the predetermined substance through the stopper and into the device. In one such embodiment, the penetrable region of the underlying portion is substantially infusible in response to the application of radiation from the laser source, and the penetrable region of the resealable portion is fusible in response to the application of radiation from the laser source to form a gas-tight seal between the resealable portion and the predetermined substance in the device after removing the needle therefrom. In one embodiment, the device is a vial. In another embodiment, the device is a syringe.

In accordance with another aspect, the present invention is directed to the device in combination with a needle for penetrating the needle penetrable and laser resealable portion. The needle includes a non-coring, conically-pointed tip defining an included angle within the range of about 15 degrees to about 25 degrees.

In accordance with another aspect, the present invention is directed to a device including a needle penetrable and laser resealable portion that is pierceable with a needle to form a needle aperture therethrough to fill a chamber of the device with a predetermined substance through the needle, and is laser resealable to hermetically seal the needle aperture by applying laser radiation at a predetermined wavelength and power thereto. The needle penetrable and laser resealable portion includes a thermoplastic and defines a predetermined wall thickness in an axial direction thereof. The needle penetrable and laser resealable portion further includes (i) first means for substantially preventing the formation of particles released into the chamber from the stopper upon penetrating the stopper with the needle and withdrawing the needle from the stopper, and (ii) second means for allowing the thermoplastic to substantially absorb laser radiation at the predetermined wavelength and substantially prevent the passage of radiation through the predetermined wall thickness thereof, and hermetically seal a needle aperture formed in the needle penetration region thereof in a predetermined time period of less than approximately 2 seconds.

In one embodiment, the first means is defined by the thermoplastic including a styrene block copolymer, an olefin, and a lubricant. In one such embodiment, the thermoplastic includes an olefin within the range of about 3% to about 20% by weight, and a styrene block copolymer within the range of about 80% to about 97% by weight.

In one embodiment, the first means is defined by the thermoplastic including (i) a first polymeric material in an amount within the range of about 80% to about 97% by weight and defining a first elongation, (ii) a second polymeric material in an amount within the range of about 3% to about 20% by weight and defining a second elongation that is less than the first elongation of the first material, and (iii) a lubricant in an amount that reduces friction forces at an interface of the needle and body.

In accordance with another aspect, the present invention is directed to a method of providing and filling a device with a predetermined substance. The method comprises the following steps: (i) providing a needle penetrable and laser resealable portion including a thermoplastic that is pierceable with a needle to form a needle aperture therethrough, and is laser resealable to hermetically seal the needle aperture by applying laser radiation at a predetermined wavelength and power thereto, wherein the needle penetrable and laser resealable portion defines a predetermined wall thickness in an axial direction thereof; (ii) providing the thermoplastic with a predetermined amount of pigment that allows the needle penetrable and laser resealable portion to substantially absorb laser radiation at the predetermined wavelength and substantially prevent the passage of radiation through the predetermined wall thickness; (iii) connecting the needle penetrable and laser resealable portion to a device defining a chamber; (iv) providing a needle defining a non-coring, conically-pointed tip and at least one flow aperture located adjacent to the tip and connectable in fluid communication with a source of the predetermined substance; (v) configuring at least one of the needle penetrable and laser resealable portion and needle to substantially prevent the formation of particles released into the chamber from the thermoplastic upon penetrating same with the needle and withdrawing the needle therefrom; (vi) penetrating the needle penetrable and laser resealable portion with the conically-pointed tip of the needle such that the flow aperture of the needle is in fluid communication with the chamber of the device, and substantially preventing the formation of particles released into chamber from the thermoplastic during penetration by the needle; (vii) introducing the predetermined substance through the needle and into the chamber of the device, withdrawing the needle from the needle penetrable and laser resealable portion, and substantially preventing the formation of particles released into the chamber from the thermoplastic during withdrawal of the needle; and (viii) transmitting laser radiation at the predetermined wavelength and power onto the needle penetrated region of the needle penetrable and laser resealable portion, and hermetically sealing the needle aperture formed in the needle penetrable and laser resealable portion and the predetermined substance within the chamber.

In one embodiment, the step of configuring at least one of the needle penetrable and laser resealable portion and needle to substantially prevent the formation of particles released into the chamber includes providing a thermoplastic including a styrene block copolymer and an olefin, and providing a lubricant at an interface of the needle and needle penetrable and laser resealable portion. In one such embodiment, the method further comprises providing a thermoplastic including an olefin within the range of about 3% to about 20% by weight, and a styrene block copolymer within the range of about 80% to about 97% by weight. In one such embodiment, the step of providing a lubricant includes providing within the thermoplastic a predetermined amount of lubricant that reduces friction forces at the interface of the needle and thermoplastic. In one such embodiment, the step of providing a lubricant includes providing a lubricant selected from the group including silicone, mineral oil and silicone oil.

In one embodiment, the step of configuring at least one of the needle penetrable and laser resealable portion and needle to substantially prevent the formation of particles released into the chamber includes providing a low-friction coating on the needle. In one such embodiment, the low-friction coating is selected from the group including tungsten carbide and titanium.

In one embodiment, the step of configuring at least one of the needle penetrable and laser resealable portion and needle to substantially prevent the formation of particles released into the chamber includes providing a thermoplastic including (i) a first polymeric material in an amount within the range of about 80% to about 97% by weight and defining a first elongation, (ii) a second polymeric material in an amount within the range of about 3% to about 20% by weight and defining a second elongation that is less than the first elongation of the first material, and (iii) a lubricant in an amount that reduces friction-forces at an interface of the needle and needle penetrable and laser resealable portion.

In accordance with another aspect, the method further comprises the steps of molding the needle penetrable and laser resealable portion and device; and prior to allowing the needle penetrable and laser resealable portion and device to cool to an ambient temperature, assembling the needle penetrable and laser resealable portion and device and forming a sealed, sterile chamber therebetween.

The method preferably further comprises the step of sterilizing the sealed, empty needle penetrable and laser resealable portion and device assembly prior to the step of needle penetrating the needle penetrable and laser resealable portion. In some such embodiments, the sterilizing step is selected from the group including (i) applying gamma radiation, (ii) applying e-beam radiation, and (iii) applying laser radiation, to the sealed, empty needle penetrable and laser resealable portion and device assembly.

In accordance with another aspect, the step of providing a needle penetrable and laser resealable portion includes providing a needle penetrable and laser resealable portion defining an underlying portion formed of a first material compatible with the predetermined substance and defining a substance-exposed surface exposed to the predetermined substance within the device, and a resealable portion overlying the underlying portion. The resealable portion and underlying portion are penetrable by the needle for introducing the predetermined substance through the needle penetrable and laser resealable portion and into the chamber. In one such embodiment, the step of providing a needle penetrable and laser resealable portion further includes providing a penetrable region of the underlying portion that is substantially infusible in response to the application of thermal energy from the laser source, and providing a penetrable region of the resealable portion that is fusible in response to the application of thermal energy from the laser source to form a gas-tight seal between the resealable portion and the predetermined substance in the device upon removing the needle therefrom.

In accordance with another aspect, the step of introducing the predetermined substance through the needle and into the chamber of the device includes introducing the predetermined substance through a first fluid passageway of the needle, and allowing fluid to flow out of the chamber through a second fluid passageway upon introducing predetermined substance from the first fluid passageway into the chamber.

One advantage of the apparatus and method of the present disclosure, is that the caps and locking members are secured to the vials prior to filling, thus enhancing the ability to maintain sterile conditions throughout the filling process and avoiding the need to assemble the vials in a sterile environment. As a result, the apparatus and method of the present disclosure significantly reduce processing time and cost in comparison to prior art vials and filling systems, and moreover, significantly increase the assurance of sterility throughout the assembly and filling processes.

Other advantages of the present invention will become readily apparent in view of the following detailed description and accompanying drawings.

BRIEF DESCRIPTION OF THE DRAWINGS

FIGS. 12A through 12D are somewhat schematic, cross-sectional, sequential views illustrating an apparatus and method for hermetically sealing the penetrated region of the resealable portion of the cap by direct heat sealing after withdrawing the filling needle therefrom.

FIGS. 30A-30F are enlarged perspective views of the filling unit of the filling machine of FIGS. 18-20 including one embodiment of a laser sealing and IR sensing manifold used therein.

FIGS. 37A-37D are perspective views of one embodiment of the laser optic and IR sensor assembly used in the laser sealing and IR sense manifold of FIGS. 30A-30F.

DETAILED DESCRIPTION OF THE PREFERRED EMBODIMENTS

Figure 1:
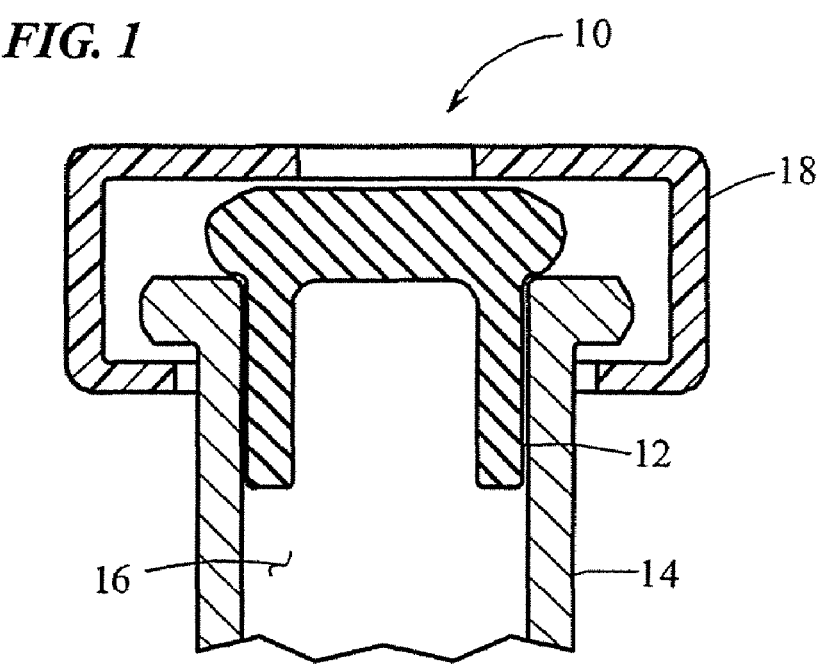
FIG. 1 is a somewhat schematic, partly-exploded, cross-sectional view of a prior art end cap for a medicament vial.

As shown in FIG. 1, a prior art cap for a medicament vial is generally designated by the reference numeral 10. The cap 10 includes a vulcanized rubber base 12, which is slidably received within the open end of a vial 14. The vial 14 is made of glass or like material, and it defines a chamber 16 for receiving medicament. An aluminum locking ring 18 surrounds the periphery of the cap 12 and vial 14, and it is crimped in place to lockably connect and seal the cap to the vial.

In operation, a hypodermic needle (not shown) is inserted through the vulcanized rubber base in order to deposit medicament within the chamber 16. Once the medicament has been deposited, the needle is withdrawn from the cap 10. Although the hole resulting from insertion of the needle will shrink somewhat from its maximum diameter due to the resiliency of the vulcanized rubber, the resultant hole is typically still large enough to pass gas or vapor and thereby compromise any preservative-free medicament contained within the chamber 16.

Figure 2:
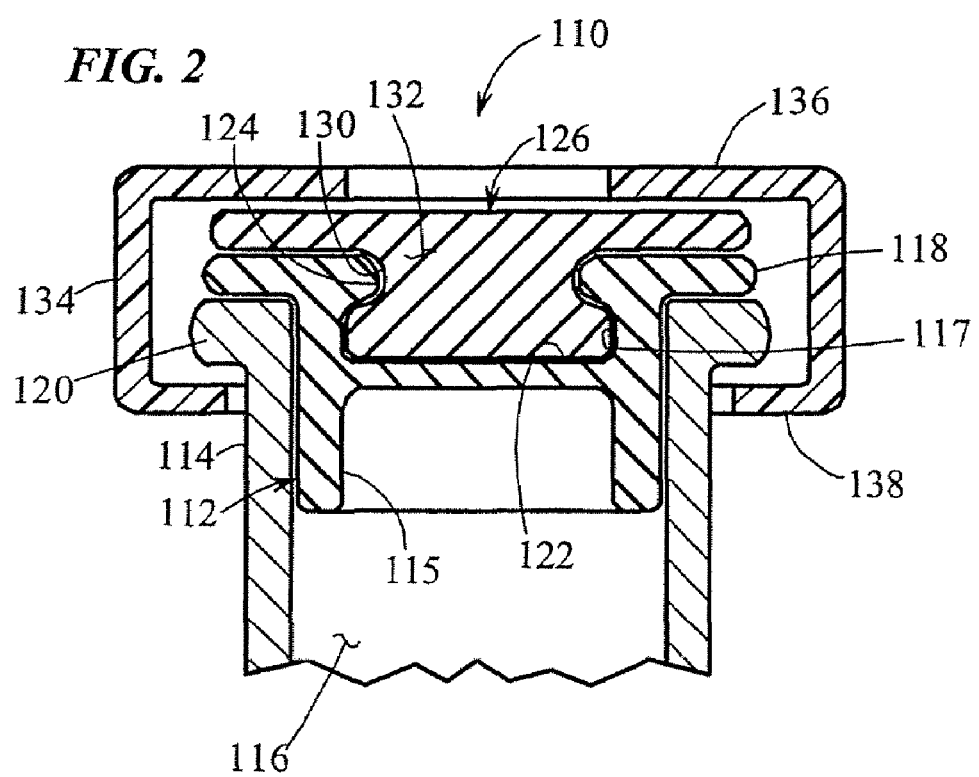
FIG. 2 is a cross-sectional, partly-exploded view of a resealable cap embodying the present invention.

Turning to FIG. 2, a heat-resealable cap or stopper is indicated generally by the reference numeral 110. The cap 110 includes a resilient base 112 made of vulcanized rubber or like material which is known to those of ordinary skill in the pertinent art, and acceptable for use in the manufacture of end caps or the portions thereof placed in contact with, or otherwise exposed to medicaments, such as vaccines. The base 112 defines a lower peripheral wall 115 shaped and dimensioned to be slidably received within the open end of a vial 114. The vial 114 is made of glass or like material, and it defines a chamber 116 for receiving medicament. The base 112 of the cap 110 further defines an upper peripheral wall 117 also shaped and dimensioned to be slidably received within the open end of the vial 114, and a peripheral sealing flange 118 projecting outwardly from the upper end of the peripheral wall 117. The vial 114 is made of glass or other suitable material, and defines at its open end a peripheral flange 120. As shown partly exploded in FIGS. 2 and 3, the peripheral flange 118 of the base 112 sealingly engages the peripheral flange 120 of the vial 114 to seal the interface between the cap and vial. The base 112 further defines an upper recess 122 formed within the upper peripheral wall 117, and an annular rim 124 projecting inwardly from the upper end of the peripheral wall.

Figure 3:
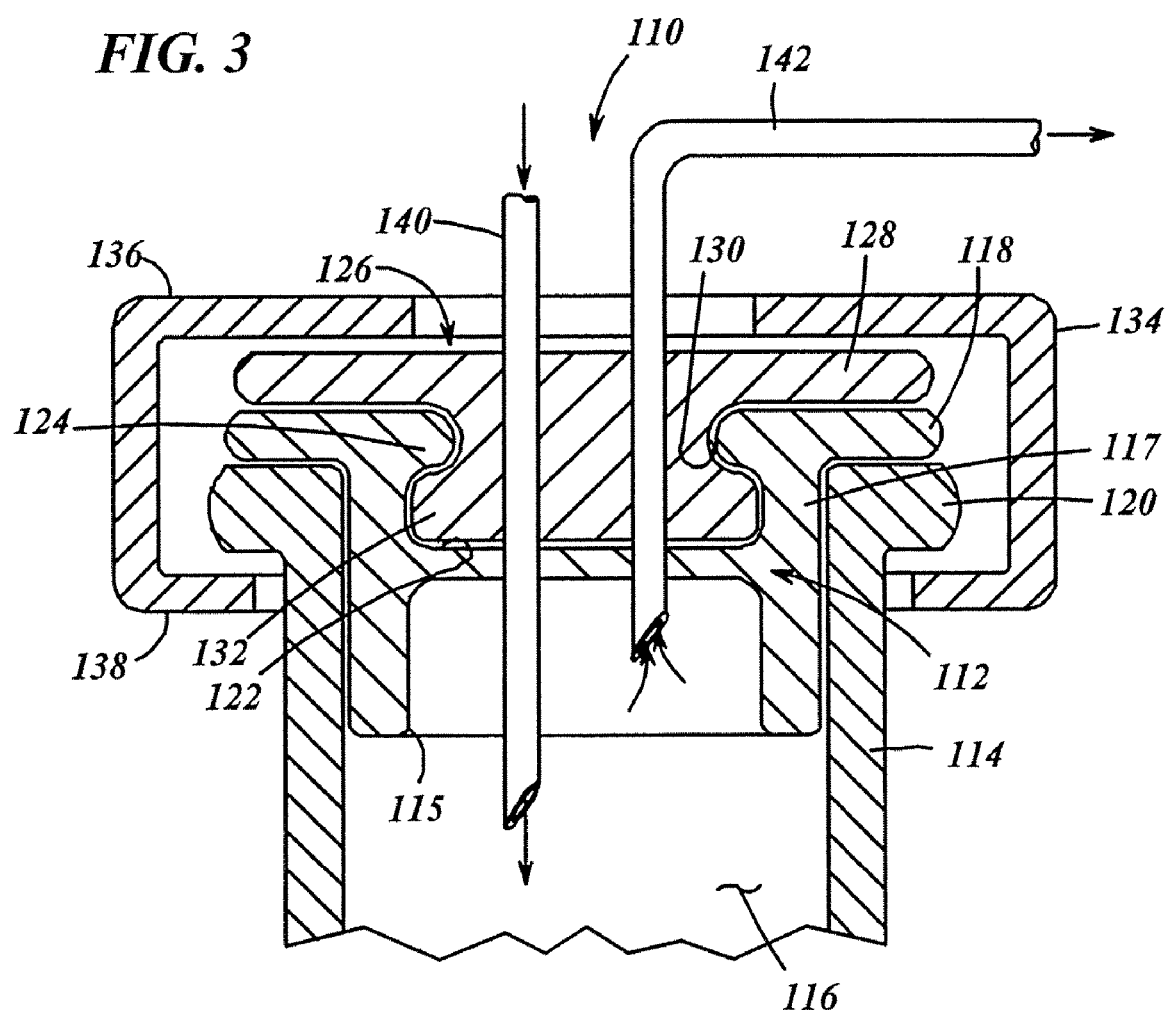
FIG. 3 is a cross-sectional, partly-exploded view of the resealable cap of FIG. 2 shown with an injection needle or syringe inserted through the end cap for introducing medicament into the vial, and a venting needle or syringe inserted through the end cap for venting the vial during filling of the medicament.
Figure 4:
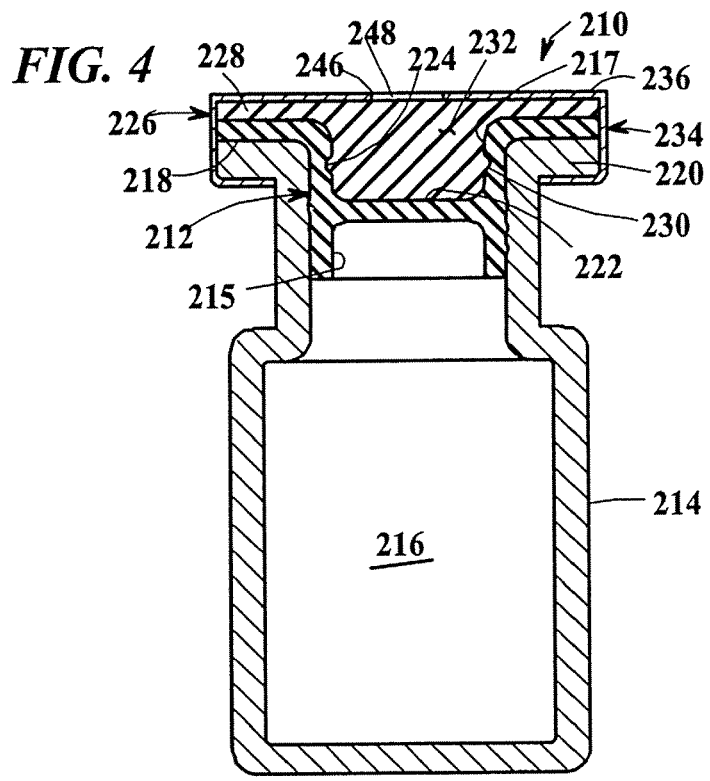
FIG. 4 is a cross-sectional view of another embodiment of the resealable cap and vial.

A resealable member 126 is fixedly received within the upper recess 122 of the base 112 to form the assembled cap 110. The resealable member 126 defines an upper peripheral flange 128, an annular recessed portion or recess 130, and a base 132 located on the opposite side of the annular recess 130 relative to the flange, and projecting outwardly from the recess. As can be seen in FIGS. 2 and 3, the annular recess 130 and base 132 of the resealable member 126 are dimensioned and shaped complementary to (or define the mirror image of) the interior surfaces of the upper recess 122 and annular rim 124 of the base 112. Accordingly, the resealable member 126 is pressed, snapped or otherwise received within the upper recess 122 such that the annular rim 124 is received within the annular recess 130 to thereby fixedly secure the resealable member within the base.

In one embodiment, the resealable member 126 is made of a resilient polymeric material, such as a blend of the polymeric material sold by Kraton Polymers and GLS Corporation under the registered trademark KRATON® and a low-density polyethylene, such as the polyethylene sold by Dow Chemical Co. under the trademarks ENGAGE™ or EXACT™, or can be made of other resilient polymeric materials as described in connection with alternative embodiments of the resealable stopper below. An important feature of the resealable member 126 is that it be resealable to form a gas-tight seal after inserting a needle, syringe or like injection member through the resealable member. Preferably, the resealable member can be sealed by heating the area punctured by the needle in a manner known to those skilled in the pertinent art and described further below. One advantage of the blended polymer described above is that it is known to minimize the degree to which the medicament can be absorbed into the polymer in comparison to KRATON® itself.

An aluminum locking or crimping ring 134 defining an upper peripheral flange 136 and a lower peripheral flange 138 is mounted over the end cap 110 and vial 114. The locking ring 134 is of a type known to those of ordinary skill in the pertinent art for fixedly securing end caps to vials, and may take the shape or form of any of numerous different locking rings which are currently or later become known for performing the functions of the locking ring described herein. The upper and lower flanges 136 and 138, respectively, of the locking ring are crimped or otherwise pressed against the adjacent surfaces of the cap and vial to press the sealing flanges of the cap against the vial and thereby maintain a fluid-tight and/or gas-tight seal between the cap and vial.

As shown in FIG. 3, the heat-resealable cap 110 is shown with a hypodermic or other type of needle 140 inserted through the resealable member 126 and the resilient base 112 in order to dispense medicament into the chamber 116 of the vial. A venting needle 142 is likewise inserted through the resealable member 126 and the resilient base 112 in order to allow gas to escape from the vial 114 as the medicament is deposited into the vial.

In operation, the resealable member 126 is inserted into the base 112, and the assembled end cap 110 is slidably inserted into the open end of the vial 114. The locking ring 134 is then crimped in place to lock the cap 110 to the vial and maintain the gas-tight seal at the interface of the cap and vial. The assembled cap 110 and vial 114 preferably are then sterilized, such as by exposing the assembly to beta and/or gamma radiation in a manner known to those of ordinary skill in the pertinent art. The medicament-dispensing needle 140 is then inserted through the resealable member 126 and the resilient base 112 until the free end of the needle is received into the chamber 116 of the vial to, in turn, dispense medicament into the chamber. The venting needle 142 is likewise inserted through the resealable member 126 and the resilient base 112 in order to draw gas from the sealed vial as the liquid medicament is deposited within the chamber of the vial. Once the medicament has been deposited within the chamber of the vial, the needles 140 and 142 are withdrawn from the cap 110, and as described further below, a heat or other energy source is applied to the portions of the resealable member 126 punctured by the needles 140 and 142 to, in turn, seal the punctured areas and hermetically seal the medicament within the vial.

Figure 5:
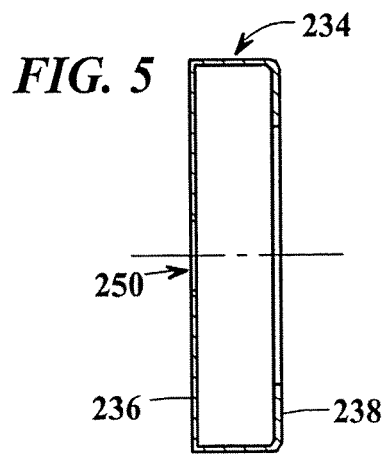
FIG. 5 is a cross-sectional view of the crimpable locking member of FIG. 4 for securing the resealable cap to the vial.
Figure 6:
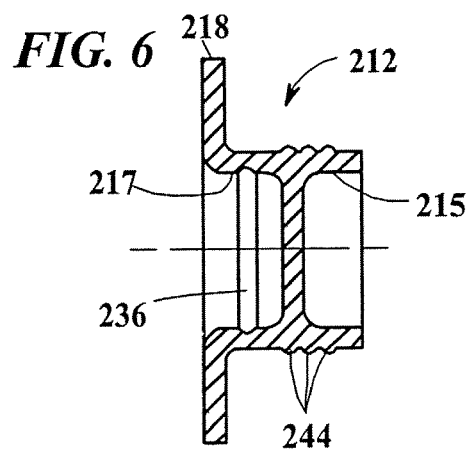
FIG. 6 is a cross-sectional view of the base portion of the resealable cap of FIG. 4 made of a material compatible with the predetermined medicament to be sealed within the vial, such as vulcanized rubber.

In FIGS. 4 through 8 another embodiment of a resealable cap is indicated generally by the reference numeral 210. The resealable cap or stopper 210 is essentially the same as the cap 110 described above, and therefore like reference numerals preceded by the numeral "2" instead of the numeral "1" are used to indicate like elements. As shown best in FIGS. 4 and 6, the base 212 of the cap defines on the interior side of its upper peripheral wall 217 an annular groove 230. As shown best in FIGS. 4 and 7, the resealable member 226 defines on the peripheral surface of its base 232 an annular raised portion or protuberance 224 dimensioned to be frictionally received within the corresponding annular groove 230 of the base 212 to thereby secure the resealable member to the base. As shown in FIG. 6, the base 212 further defines on the exterior side of its lower peripheral wall 215 a plurality of raised annular portions or protuberances 244 axially spaced relative to each other for frictionally engaging the interior wall of the vial 214 to thereby secure the cap within the vial and facilitate maintaining a hermetic seal between the cap and vial. As shown best in FIGS. 7 and 8, the resealable member 226 defines on its top surface an annular raised portion or protuberance 246 defining a circular surface portion 248 therein for receiving a filling needle or like instrument, as described further below. As shown in FIG. 5, the locking or crimping ring 234 defines a central aperture 250 in its upper side for receiving therethrough the annular raised portion 246 of the resealable member 226.

Preferably, the resealable cap 210 and vial 214 are assembled and the locking ring 234 is crimped in place as described above and shown in FIG. 4 prior to introducing any medicament or other fluid into the vial. Then, one or more of the empty cap/vial assemblies herein described may be enclosed, sterilized, and transported in accordance with the teachings of the present inventor's commonly owned U.S. Pat. No. 5,186,772, entitled "Method Of Transferring Articles, Transfer Pocket And Enclosure", and/or U.S. patent application Ser. No. 10/421,249, entitled "Transfer Port and Method For Transferring Sterile Items", filed Sep. 10, 2002, each of which is hereby expressly incorporated by reference as part of the present disclosure. The empty cap/vial assemblies are placed in an internal bag or "pocket" which is closed and, if desired, provided with a sterilization indicator. Then, the internal pocket is placed within a transfer pocket including a sealing frame defining an annular groove on a peripheral surface thereof. The transfer pocket is stretched over the surface of the frame and closed by an elastic band overlying the transfer pocket and received within the peripheral groove. The transfer pocket likewise may include therein a sterilization indicator. Preferably, the assembled transfer and internal pockets are sealed within an "external" pocket and the assembled pockets are subject to sterilization, such as by exposure to gamma radiation, to sterilize the pockets and the empty cap/vial assemblies within the pockets. The transfer pockets can then be used to store and/or transport the sterilized assemblies to a filling system without contaminating the sterilized assemblies.

As further described in the above-mentioned patent and patent application, the filling system is located within a sterile enclosure, and the empty vials are introduced into the enclosure by removing and discarding the external pocket, and connecting the sealing frame of the transfer pocket to a window or transfer port of the enclosure. As further disclosed in the above-mentioned patent and patent application, an adhesive material is preferably superimposed on the sealing frame for securing the transfer pocket to the transfer port of the filling system enclosure. Prior to releasing the cap/vial assemblies into the filling system enclosure, the sterilization indicators are preferably checked in order to ensure that the sterile condition of the vial/cap assemblies were maintained throughout storage and transfer. As described in the above-mentioned patent and patent application, the portion of the transfer pocket overlying the frame is then cut away and simultaneously sterilized along the trimmed surfaces to destroy any microorganisms or germs thereon, and to allow the internal pocket to be received through the transfer port and into the enclosure.

Once received within the enclosure, the internal pocket is opened and the empty cap/vial assemblies are removed and loaded into a filling machine located within the sterile enclosure. Once loaded into the filling machine, the resealable member 226 of each empty cap/vial assembly may be sterilized again in order to further ensure that no contaminates enter the vial during the filling process. In accordance with some embodiments, the resealable members 226 are sterilized at this stage by either direct heat cauterization or laser or other radiation cauterization.

Figure 9:
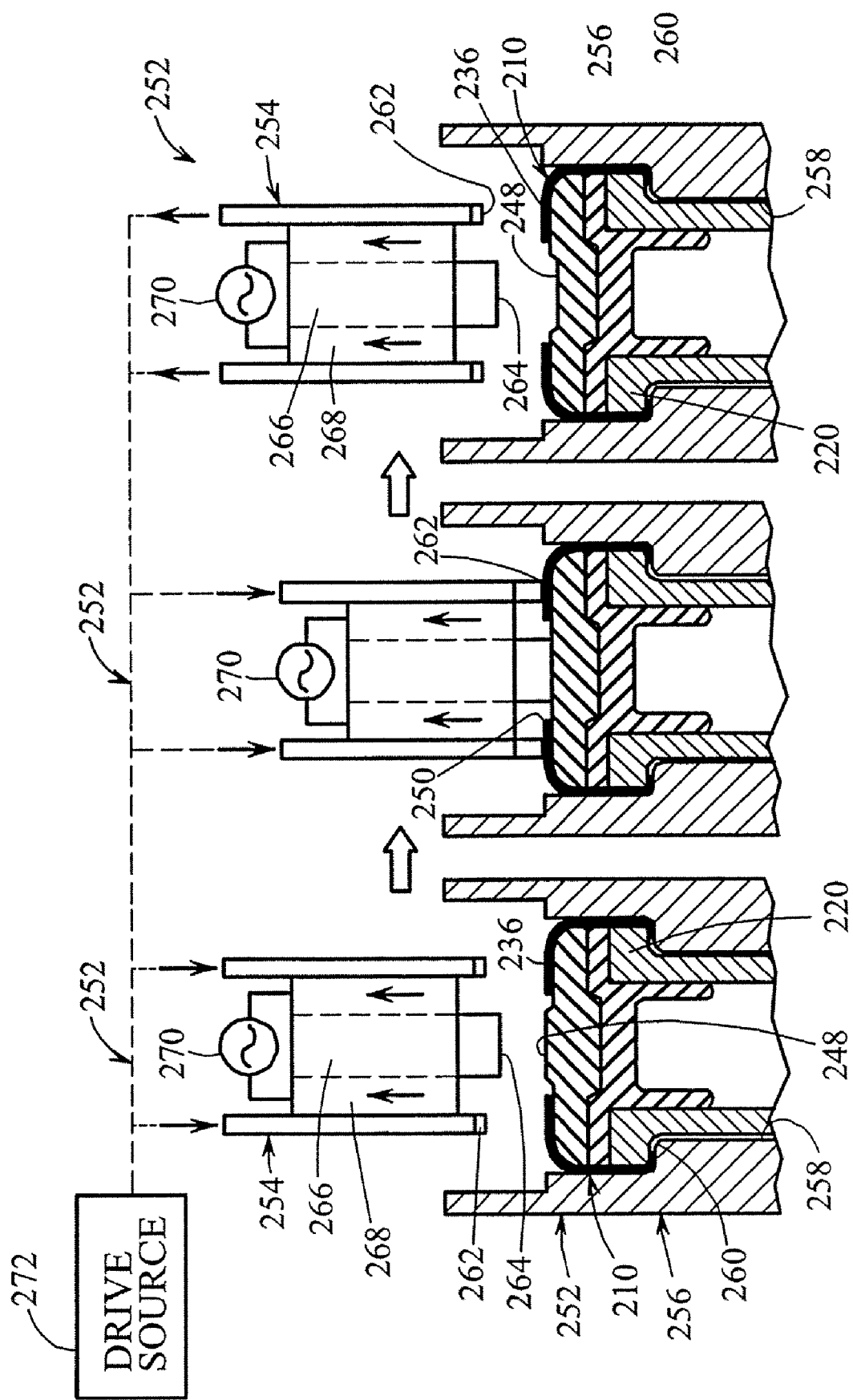
FIGS. 9A through 9C are somewhat schematic, cross-sectional, sequential views illustrating an apparatus and method for sterilizing the resealable portion of the cap by direct heat cauterization prior to introducing the filling needle or like instrument therethrough.

As shown in FIGS. 9A through 9C, an apparatus for cauterizing the resealable caps by application of heat thereto is indicated generally by the reference numeral 252. The apparatus 252 comprises a housing 254 mounted over a vial support 256. The vial support 256 may be adapted to hold a single vial, or preferably, is adapted hold a plurality of vials. The embodiment of the support adapted to hold a plurality of vials defines a channel 258 for receiving therein the vials, and a pair of opposing shoulders 260 formed at the upper edge of the channel for supporting thereon the flange 220 of the vial. If desired, a vibratory drive (not shown) may be drivingly connected to the support 256 to vibrate the support and, in turn, move the vials through the channel at a predetermined rate. However, as may be recognized by those skilled in the pertinent art based on the teachings herein, any of numerous different drive systems that are currently, or later become known, may be equally employed to move the vials through the filling machine.

The housing 254 defines a peripheral sealing surface 262 formed on the free end of the housing for sealingly engaging the upper flange surface 236 of each locking member 234. As shown best in FIG. 9B, the peripheral sealing surface surrounds the aperture 250 formed through the locking member and exposing the penetrable region 248 of the resealable member 226 of the cap. Preferably, the peripheral sealing surface 262 forms a substantially fluid-tight seal between the housing and the cap. A heating surface 264 projects outwardly from the free end of a central support 266 of the housing for contacting the penetrable surface 248 of the resealable member and cauterizing the surface. An annular conduit 268 extends about the periphery of the heating surface 264 and is coupled in fluid communication to a vacuum source 270 for drawing air through the conduit and away from the cauterized surface 248, as indicated by the arrows in the Figures. The housing 254 is drivingly connected to a drive source 272 for moving the housing and thus the heating surface 264 into and out of engagement with the exposed penetrable surface portion 248 for cauterizing the surface, as indicated by the arrows in the Figures. As may be recognized by those skilled in the pertinent art based on the teachings herein, the drive source 272 may take the form of any of numerous different types of drive sources that are currently, or later become known, for performing the function of the drive source as described herein, such as a pneumatic drive, or a solenoid-actuated or other type of electric drive. Similarly, the heating surface 264 may take any of numerous different shapes and configurations, and may be heated in any of numerous different ways that are currently or later become known, such as by an electric resistance heater (or "hot wire"). Preferably, however, the heating surface 264 defines a surface shape and contour corresponding to the desired shape and contour of the penetrable surface region 248 of the cap.

Figure 7:
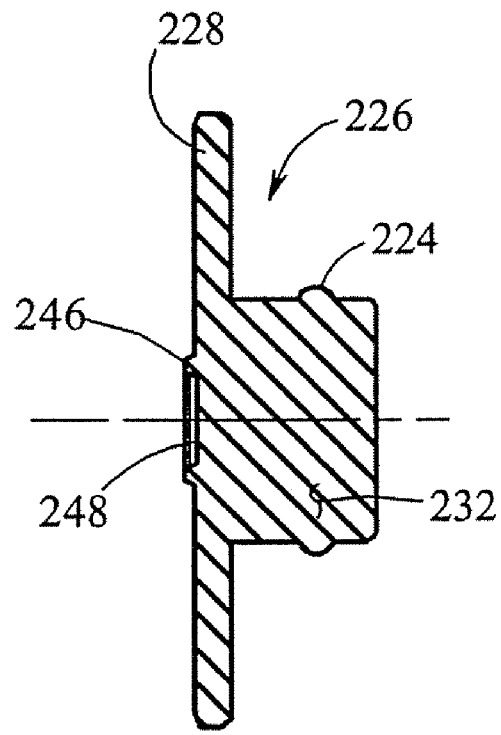
FIG. 7 is a cross-sectional view of the resealable portion of the cap of FIG. 4 formed of a material that is fusible in response to the application of thermal energy thereto in order to hermetically seal the cap after inserting and removing a filling needle or like instrument therethrough.
Figure 8:
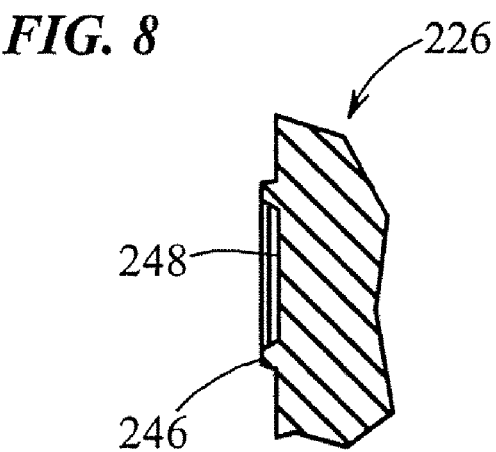
FIG. 8 is an enlarged, partial, cross-sectional view of the resealable portion of FIG. 7 and showing the penetrable portion thereof for receiving a needle or like instrument therethrough.

In the operation of the apparatus 252, and as shown typically in FIG. 9A, each vial is first introduced into the cauterizing station with the penetrable surface region 248 of the resealable member 226 aligned with the heating surface 264. Then, the drive source 272 is actuated to drive the housing 254 downwardly until the peripheral sealing surfaces 262 sealingly engage the upper flange surface 236 of the respective locking member 234, and the heating surface 264 simultaneously engages the exposed penetrable surface portion 248 of the resealable member 226. The heated surface 264 is maintained at a predetermined temperature, and is held in contact with the exposed surface portion 248 for a predetermined time period, sufficient to cauterize the exposed surface portion. One advantage of the construction of the resealable member 226 as shown in FIGS. 7 and 8, is that the cauterization process deforms the annular protuberance 246 into a contour conforming to that of the heated surface, thus allowing an operator (or optical or other automatic sensing system) to visually determine whether each cap has been properly cauterized prior to filling. As shown in FIG. 9C, after cauterizing the exposed surface, the drive source 272 is actuated to drive the housing 254 upwardly and out of engagement with the cap, another vial is moved under the housing, and the process is repeated until all desired vials are cauterized. As described further below, upon exiting the cauterizing station of FIGS. 9A through 9C, the vials are preferably then moved into a filling station to promptly fill the sterilized vials. The cauterization and filling stations are preferably mounted within a sterile enclosure with a laminar gas flow through the enclosure to facilitate maintaining the sterile conditions, such as described in U.S. Pat. No. 5,641,004 to Daniel Py, issued Jun. 24, 1997, which is hereby expressly incorporated by reference as part of the present disclosure, or described in connection with the embodiments below.

In one embodiment, the temperature of the heating surface is within the range of approximately 250° C. to 300° C., and the cycle times (i.e., the time period during which the heating surface is maintained in contact with the exposed surface 248 of the resealable member) are within the range of approximately 1.0 to 3.0 seconds. The present inventor has determined that these temperatures and cycle times may achieve at least approximately a 6 log reduction in bio-burden testing to thereby effectively sterilize the surface.

Figure 10:
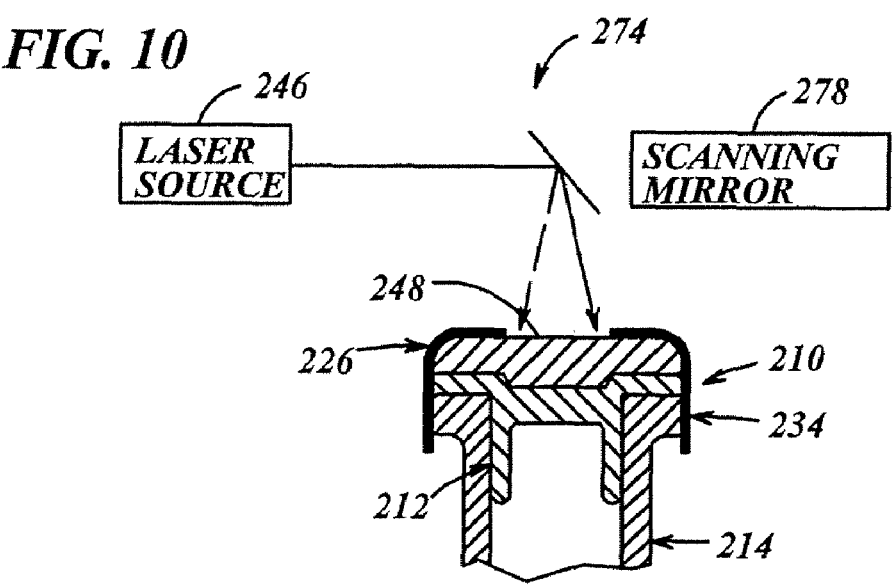
FIG. 10 is a somewhat schematic, partial cross-sectional view of an apparatus for sterilizing the resealable portion of the cap by laser cauterization prior to introducing the filling needle or like instrument therethrough.

In FIG. 10, an alternative apparatus for cauterizing the resealable caps is indicated generally by the reference numeral 274. The apparatus 274 differs from the apparatus 252 of FIGS. 9A through 9C in that the thermal energy required for sterilizing the filling area of the resealable member is supplied by a laser (referred to herein as "laser cauterization"). The laser cauterization apparatus 274 comprises a laser or other suitable radiation source 276 optically coupled to a scanning mirror 278 mounted over the vial/cap assembly. Although not shown in FIG. 10, the vials are preferably mounted within the same type of support as shown in FIGS. 9A through 9C in order to allow the resealable caps to be rapidly cauterized in succession prior to filling each vial with medicament, as described further below.

In one embodiment, the laser 276 is a commercially available $CO_2$ or YAG laser. The $CO_2$ laser operates at a wavelength of approximately 10.6 μm. At this wavelength, absorption of the laser energy is governed by the electrical conductivity of the material. Therefore, an insulating material, such as the elastomeric material of the resealable member 226, absorbs and converts most of the incident energy into thermal energy to cauterize the receiving surface 248. The YAG laser operates at wavelength of approximately 1.06 μm. At this frequency, absorption is governed by the lattice atoms. Thus, a clear or transparent polymer with little ionization would be permeable to the laser beam. Accordingly, when employing a YAG laser, it is desirable to add a colorant to the elastomeric material of the resealable member in a manner known to those of ordinary skill in the pertinent art in order to enhance its absorption of the laser energy. A significant advantage of the YAG laser is that the superficial layer of the penetrable region of the resealable member, and any germs, bacteria or other contaminants thereon, are transformed into plasma to rapidly and thoroughly sterilize the effected surface. If necessary, a UV-filtration coating may be applied to the surfaces of the enclosure for the apparatus to prevent the operators from receiving any unnecessary UV exposure.

The present inventor has demonstrated that beam energies in the range of approximately 15 to 30 W are sufficient to effectively cauterize the surface 248 of the elastomeric resealable member. In addition, bio-burden testing has demonstrated that laser energies of approximately 20 W or greater may achieve about a 6.0 log reduction. At these energies, the apparatus may effectively sterilize the surface 248 within a cycle time of approximately 0.5 seconds. Accordingly, a significant advantage of the laser cauterization apparatus and method is that they may involve significantly shorter cycle times than various direct heat methods. Yet another advantage of the laser cauterization, is that it involves both a non-contact method and apparatus, and therefore there is no need to be concerned with the cleaning of a contact head or like heating surface.

Figure 11:
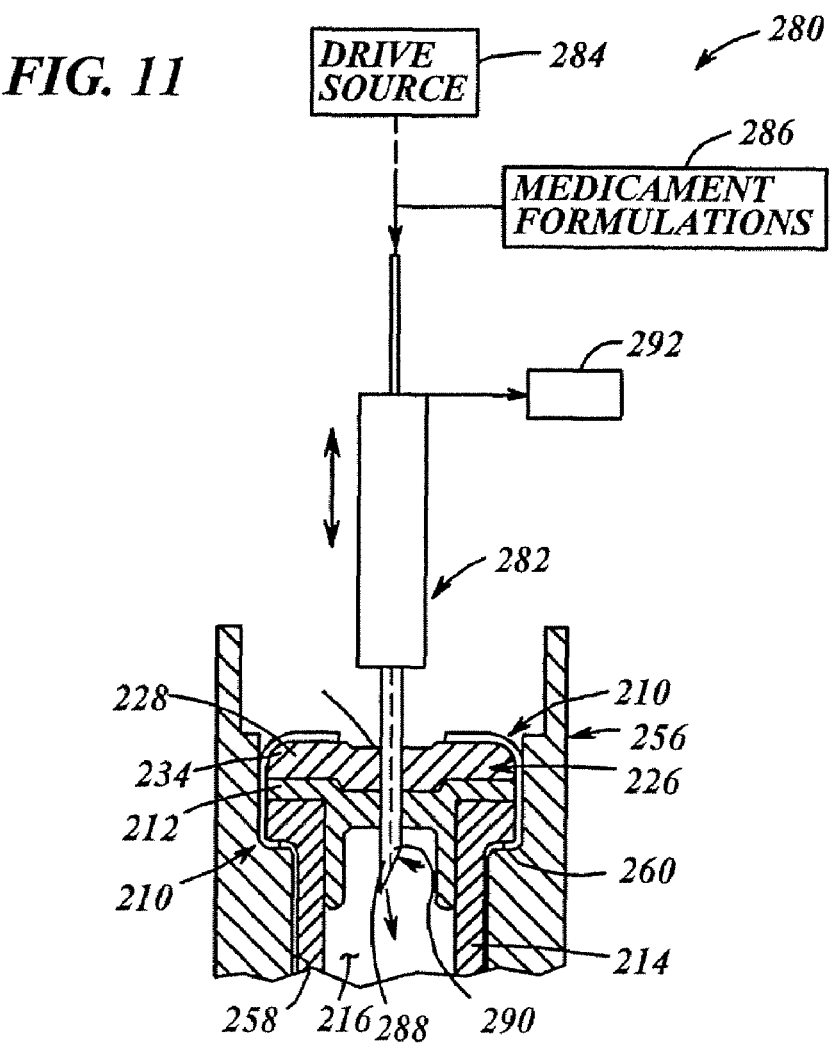
FIG. 11 is a somewhat schematic, partial cross-sectional view of an apparatus for needle filling the assembled cap, vial and locking member with a predetermined medicament.

Turning to FIG. 11, after direct heat or laser cauterization of the resealable member 226 of each vial, the vial is moved within the support 256 (such as by vibratory drive) into a filling station 280. The filling station 280 includes a needle or like injection member 282 reciprocally mounted over the support 256, as indicated by the arrows in FIG. 11, and axially aligned with the penetrable region 248 of the resealable member 226 of each vial/cap assembly passing therethrough. A drive source 284 is drivingly connected to the needle 280 for reciprocally driving the needle 282 into and out of engagement with each cap 210. A medicament or other formulation reservoir 286 is coupled in fluid communication with the needle 282 for introducing a predetermined medicament or other formulation through the needle and into the vial. In one embodiment, the needle 282 defines a plurality of fluid conduits therein, including a first fluid conduit 288 for injecting the predetermined medicament or other formulation into the vial, as indicated by the arrow in FIG. 11, and a second fluid conduit 290 coupled in fluid communication with a vacuum source 292 for withdrawing air or other gases from the interior cavity 216 of the vial prior to and/or during the filling of the cavity with the medicament or other formulation. In the illustrated embodiment, the needle 282 is a "double lumen" needle, defining a central fluid conduit 288 for injecting the predetermined medicament or other formulation into the vial, and an outer annular fluid conduit 290 for drawing the displaced air or other gases out of the interior cavity of the vial.

As shown in FIGS. 12A through 12D, after filling the vial with the medicament or other formulation and withdrawing the needle 282 from the cap 210, the penetrated region of the cap defines a needle hole 294 along the path of the withdrawn needle (FIG. 12B). Upon withdrawing the needle, the vulcanized rubber and/or thermoplastic material of the cap is sufficiently resilient to close upon itself in the penetrated region and thereby maintain the vial in a sealed condition. However, as described above, vapors, gases and/or liquid may be allowed over time to pass through the needle hole, and therefore each vial/cap assembly is passed through a sealing station, as shown typically in FIG. 12C, to heat seal the resealable portion 226 of the cap promptly after withdrawing the needle therefrom. As shown typically in FIG. 12C, a heated member or surface 264 is reciprocally mounted over, and axially aligned with the penetrable region 248 of the vial/cap assembly received within the filling station. A drive source 272 is drivingly connected to the heated member 264 to reciprocally drive the heated member into and out of engagement with the resealable member of each cap. As shown typically in FIG. 12C, the heated member 264 is maintained at a sufficient temperature, and maintained in engagement with the penetrated region of the resealable member 226 to fuse the elastomeric material and hermetically seal the needle hole 294. As a result, and as shown typically in FIG. 12D, the needle hole is eliminated from the exterior region of the resealable member to thereby maintain a hermetic seal between the cap and vial.

As may be recognized by those skilled in the pertinent art based on the teachings herein, the drive source and heating member/surface of FIGS. 12A through 12D may take the form of any of numerous different drive sources and heating members as described above. As indicated typically in FIG. 12C, however, the heating member 264 may define a smaller width than the heating member/surface described above for cauterizing the penetrable region of the cap prior to filling. In addition, the temperature of the heating member 264 for sealing may be higher than that of the heating member described above in order to rapidly melt and seal the penetrated region. One advantage of the resealable cap, is that the base thermally insulates the heated region from the medicament in the vial to thereby maintain the medicament in the vial within an appropriate temperature range throughout the cauterization and heat sealing processes and thereby avoid any thermal damage to the medicament.

Figure 13A:
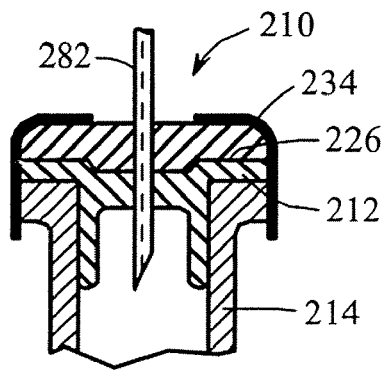
FIGS. 13A through 13C are somewhat schematic, cross-sectional, sequential views illustrating an apparatus and method for hermetically sealing the penetrated region of the resealable portion of the cap by laser sealing after withdrawing the filling needle therefrom.
Figure 13B:
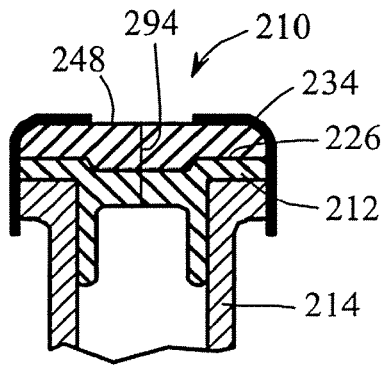
Figure 13C:
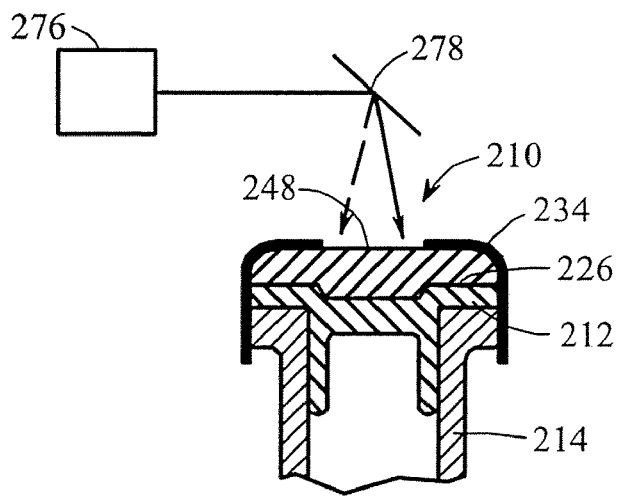

Alternatively, and as shown in FIGS. 13A through 13C, the laser source 276 and scanning mirror 278 may be employed to heat seal the penetrated region 294/248 of the resealable member. Accordingly, the same type of laser source 276 and scanning mirror 278 as described above may be employed in the heat sealing station to perform this function, or alternatively, and as described further below, a different type of laser system may be employed. In one embodiment, a $CO_2$ laser of approximately 50 W is employed to seal a region approximately 0.10 inch in diameter in the resealable cap.

Figure 14:
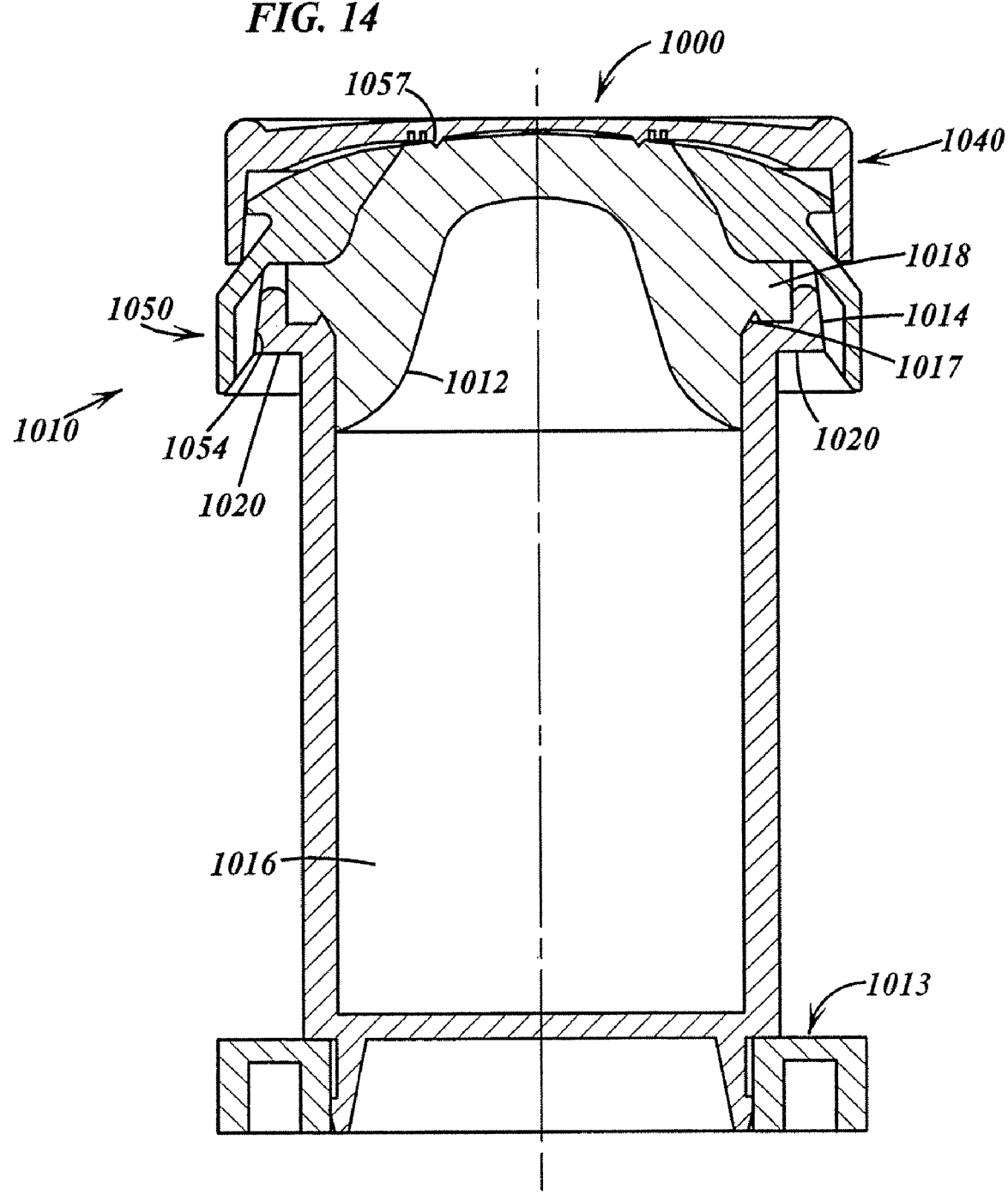
FIG. 14 is a cross-sectional view of another embodiment of a vial assembly including a rescalable stopper.

FIG. 14 shows a vial assembly according to another embodiment of the present disclosure. The vial assembly is designated generally by reference numeral 1000, with resealable cap assembly 1010. Vial assembly 1000 has a cylindrical body defining a chamber 1016 for storing a predetermined medicament, a snap-on base 1013, and a neck 1014. The cap 1010 comprises a cap or stopper member 1012, a cap or locking ring or member 1050 and a snap-off, tamper-proof cover 1040. The stopper member 1012 of the cap defines a peripheral flange 1018 which is adapted and configured for engagement with the neck 1014 of the storage vial. Stopper member 1012 provides a first primary seal for containing the predetermined medicament within the interior chamber of vial body. As can be seen, the neck 1014 of the vial defines a pointed annular protuberance 1017 that projects axially into the overlying stopper material to thereby further effectuate a hermetic seal between the stopper and vial.

Cap or locking member 1050 has an outer peripheral flange 1052 that defines a shoulder 1054 on an inner surface thereof. Shoulder 1054 is adapted and configured for interlocking engagement with lower surface 1020 of neck 1014. Cap 1050 is made from a relatively flexible, non-metallic material, such as plastic. Cap or locking member 1050 defines a central aperture that allows stopper member 1012 to be accessed therethrough by a needle or like device. Cover 1040 is configured to overlie the central aperture of locking member 1050 and engage with locking member 1050, thereby protecting the exposed stopper material. In the embodiment shown herein, cover 1040 is engaged with locking member 1050 by means of a press-fit. Cover 1040 further defines on its underside a pointed annular protuberance 1057 that is pressed into engagement with the adjacent stopper material to thereby effectuate a hermetic seal between the cover 1040 and stopper 1012. Preferably, cover 1040 cannot be removed from the vial without breaking the cover, thus providing a further tamper-resistant feature. Alternatively, the tamper resistant feature can be created by using ultrasonic welding, adhesion, or any other connection technique to engage cover 1040 with locking member 1050 so that once removed, cover 1040 can not be re-engaged with locking member 1050.

Figure 15:
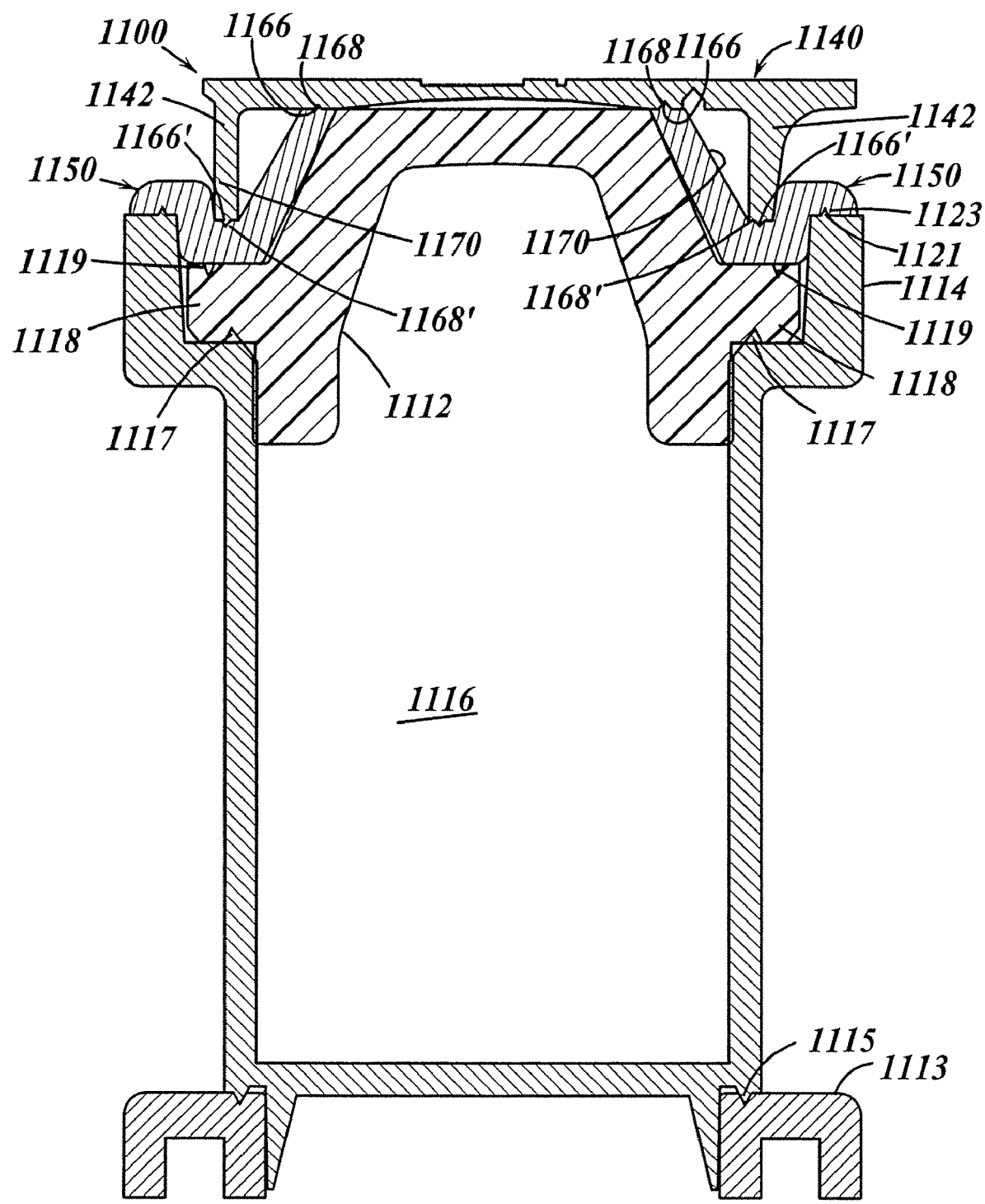
FIG. 15 is a cross-sectional view of another embodiment of a vial assembly including a rescalable stopper.

FIG. 15 shows another embodiment of a vial assembly indicated generally by the reference numeral 1100. The vial 1100 is similar in many respects to the vial described above with reference to FIG. 14, and therefore like reference numerals preceded by the numeral "11" instead of numeral "10" are used to indicate like elements. The primary difference of the vial 1100 in comparison to the vials described above is that the locking member 1110 is welded, such as by ultrasonic welding, to the neck 1114 of the vial body. In addition, the flip-top or cover 1140 is tack welded, such as by ultrasonic welding, to the locking member 1150. The stopper 1112 defines an annular flange 1118, the neck 1114 of the vial body defines a pointed annular protuberance 1117 that projects into one side of the stopper flange 1118, and the locking member 1150 defines another annular protuberance 1119 that projects into the opposite side of the stopper flange 1118. Thus, the annular protuberances 1117 and 1119 define continuous, annular sealing surfaces that facilitate in effectuating a gas-tight or hermetic seal between the stopper and vial body. The neck 1114 defines on its axial face a pointed annular protuberance 1121 that is received within a corresponding annular recess 1123 defined in the underside of the locking member 1150.

The annular protuberance 1121 is fused to the locking member 1150 within the annular recess 1123 by ultrasonic welding, for example, to thereby fixedly secure the locking member to the vial body. In addition, the annular weld preferably defines a hermetic or gas-tight seal between the locking member and vial body to further effectuate a gas-tight or hermetic seal between the interior of the vial and the ambient atmosphere.

The locking member 1150 further defines on its distal end a plurality of discrete radially-extending protuberances 1166 received within corresponding recesses 1168 formed within the underside of the locking member 1140. The protuberances 1166 are fused to the cover 1140 within the recesses 1168 by, for example, ultrasonic welding, to thereby define a plurality of frangible connections between the cover 1140 and locking member 1150. Alternatively, protuberances 1166' may be formed at the base of the flange 1142 of the cover and may be fused within corresponding recesses 1168' formed within the annular recess 1170 of the locking member. The base of the vial body may define a pointed annular protuberance 1115 that is received within a corresponding annular recess formed in the base 1113 for fixedly securing the base to the body, such as, for example, by ultrasonic welding.

Vial assemblies of the type illustrated in FIGS. 14 and 15 are disclosed in further detail in U.S. patent application Ser. No. 10/655,455, entitled: "Sealed Containers and Methods of Making and Filling Same", filed Sep. 3, 2003, which is hereby expressly incorporated by reference in its entirety as part of the present disclosure.

One advantage of the resealable stopper and vial assemblies of FIGS. 14 and 15 is that the covers 1040, 1140 may be hermetically sealed to the underlying locking members 1050, 1150 to thereby seal the stoppers 1012, 1112 within the locking members 1050, 1150 and covers 1040, 1140 and with respect to the ambient atmosphere. In accordance with one aspect of a preferred embodiment, the overlying locking members and covers can be formed of relatively rigid materials and/or of materials having relatively high resistances to moisture and vapor transmission in comparison to the material of the resealable stopper itself, in order to facilitate preventing the loss of any medicament or other substance contained within the vial or other container therethrough, or the ingress of moisture or vapor into the vial or other container, during, for example, storage, transportation and/or product shelf life.

Thus, in the currently-preferred embodiments described in the present disclosure, each sealable cap or stopper 110, 210, 1012, 1112 is formed of a thermoplastic material defining a needle penetration region that is pierceable with a needle to form a needle aperture therethrough, and is heat resealable to hermetically seal the needle aperture by applying laser radiation at a predetermined wavelength and power thereto. Each cap or stopper 110, 210, 1012, 1112 includes a thermoplastic body 126, 226, 1012, 1112 defining (i) a predetermined wall thickness in an axial direction thereof, (ii) a predetermined color and opacity that substantially absorbs the laser radiation at the predetermined wavelength and substantially prevents the passage of the radiation through the predetermined wall thickness thereof, and (iii) a predetermined color and opacity that causes the laser radiation at the predetermined wavelength and power to hermetically seal the needle aperture formed in the needle penetration region thereof in a predetermined time period and substantially without burning the needle penetration region and/or the cover portion of the cap (i.e., without creating an irreversible change in molecular structure or chemical properties of the material). In some embodiments, the predetermined time period is approximately 2 seconds, is preferably less than or equal to about 1.5 seconds, and most preferably is less than or equal to about 1 second. In some of these embodiments, the predetermined wavelength of the laser radiation is about 980 nm, and the predetermined power of each laser is preferably less than about 30 Watts, and preferably less than or equal to about 10 Watts, or within the range of about 8 to about 10 Watts. Also in some of these embodiments, the predetermined color of the material is gray, and the predetermined opacity is defined by a dark gray colorant (or pigment) added to the stopper material in an amount within the range of about 0.3% to about 0.6% by weight.

In addition to the thermoplastic materials described above, the thermoplastic material may be a blend of a first material that is preferably a styrene block copolymer, such as the materials sold under either the trademarks KRATON or DYNAFLEX, such as DYNAFLEX G2706-10000-00, or GLS 230-174 (Shore A=30), and a second material that is preferably an olefin, such as the materials sold under either the trademarks ENGACE or EXACT, such as EXACT 8203, or GLS 230-176 (Shore A=42). In some embodiments, the first and second materials are blended within the range of about 50:50 by weight to preferably about 90:10 by weight, and most preferably about 90:5 by weight (i.e., first material: second material). The benefits of the preferred blend over the first material by itself are improved water or vapor barrier properties, and thus improved product shelf life; improved heat sealability; a reduced coefficient of friction; improved moldability or mold flow rates; and a reduction in hystereses losses.

Alternatively, the thermoplastic material of the resealable stoppers may take the form of a styrene block copolymer sold by GLS Corporation of McHenry, Ill. under the designation LC 254-071. This type of styrene block copolymer compound exhibits approximately the following physical properties: (i) Shore A Hardness: about 28-29; (ii) Specific Gravity: about 0.89 g/cm$^3$; (iii) Color: approximately grey to dark grey; (iv) 300% Modulus, flow direction: about 181-211 psi. (v) Tensile Strength at Break, flow direction: about 429-498 psi; (vi) Elongation at Break, flow direction: about 675%-708%; and (vii) Tear Strength, flow direction: about 78-81 lbf/in.

In each of these embodiments, the predetermined color and opacity of the thermoplastic is defined by a grey colorant that is provided in an approximately 3% color concentrate (i.e., there is an approximately 33:1 ratio of the concentrate to the natural resin or TPE). The color concentrate contains about 88.83% carrier or base resin, the remainder is pigment, and the pigment is grey carbon black. Thus, the pigment is about 0.34% by weight of the resulting thermoplastic.

In addition, if desired, a lubricant of a type known to those of ordinary skill in the pertinent art may be added to or included within each of the above-mentioned thermoplastic compounds, in order to prevent or otherwise reduce the formation of particles upon penetrating the needle penetration region of the thermoplastic portion with a needle or other filling member. In one embodiment, the lubricant is a mineral oil that is added to the styrene block copolymer or other thermoplastic compound in an amount sufficient to prevent, or substantially prevent, the formation of particles upon penetrating same with the needle or other filling member. In another embodiment, the lubricant is a silicone, such as the liquid silicone sold by Dow Corning Corporation under the designation "360 Medical Fluid, 350 CST", or a silicone oil, that is added to the styrene block copolymer or other thermoplastic compound in an amount sufficient to prevent, or substantially prevent, the formation of particles upon penetrating same with the needle or other filling member. In one such embodiment, the silicone oil is included in an amount within the range of about 0.4% to about 1% by weight, and preferably within the range of about 0.4 to about 0.6% by weight, and most preferably within the range of about 0.51 or about 0.5% by weight.

As described further below, the configuration of the needle that is penetrating the stopper, the friction forces created at the needle/stopper interface, and/or the needle stroke through the stopper also can be controlled to further reduce or substantially prevent the formation of particles upon penetrating the stoppers with the needles.

In accordance with a further aspect, the needle penetrable and laser resealable stopper comprises: (i) a styrene block copolymer, such as any such styrene block copolymers described above, within the range of about 80% to about 97% by weight (e.g., 95% by weight as described above); (ii) an olefin, such as any of the ethylene alpha-olefins, polyolefins or olefins described above, within the range of about 3% to about 20% by weight (e.g., about 5% as described above); (iii) a pigment or colorant added in an amount sufficient to absorb the laser energy, convert the radiation to heat, and melt the stopper material, preferably to a depth equal to at least about ⅓ to about ½ of the depth of the needle hole, within a time period of less than about 2 seconds, more preferably less than about 1.5 seconds, and most preferably less than about 1 second; and (iv) a lubricant, such as a mineral oil, liquid silicone, or silicone oil as described above, added in an amount sufficient to substantially reduce friction forces at the needle/stopper interface during needle penetration of the stopper to, in turn, substantially prevent particle formation.

In accordance with a further aspect, in addition controlling one or more of the above-mentioned parameters to reduce and/or eliminate the formation of particles (i.e., including the silicone oil or other lubricant in the thermoplastic compound, and controlling the configuration of the needle, the degree of friction at the needle/stopper interface, and/or the needle stroke through the stopper), the differential elongation of the thermoplastic components of the resealable stopper is selected to reduce and/or eliminate the formation of particles.

Thus, in accordance with a further aspect, the needle penetrable and laser resealable stopper comprises: (i) a first thermoplastic material within the range of about 80% to about 97% be weight and defining a first elongation; (ii) a second thermoplastic material within the range of about 3% to about 20% by weight and defining a second elongation less than the elongation of the first material; (iii) a pigment or colorant added in an amount sufficient to absorb the laser energy, convert the radiation to heat, and melt the stopper material, preferably to a depth equal to at least about ⅓ to about ½ of the depth of the needle hole, within a time period of less than about 2 seconds, more preferably less than about 1.5 seconds, and most preferably less than about 1 second; and (iv) a lubricant, such as a mineral oil, liquid silicone, or silicone oil as described above, added in an amount sufficient to substantially reduce friction forces at the needle/stopper interface during needle penetration of the stopper to, in turn, substantially prevent particle formation.

In accordance with a further aspect, the first material defines a lower melting point (or Vicat softening temperature) than does the second material. In some of the embodiments described herein, the first material is a styrene block copolymer, such as any of the styrene block copolymers described above, and the second material is an olefin, such as any of the ethylene alpha-olefins, polyolefins or olefins described above. Also in accordance with the currently preferred embodiments, the first material defines an elongation of at least about 75% at 10 lbs force (i.e., the length increases by 70% when subjected to a 10 lb force), preferably at least about 85%, and most preferably at least about 90%; and the second material defines an elongation of at least about 5% at 10 lbs force, preferably at least about 10%, and most preferably at least about 15%, or within the range of about 15% and about 25%. With respect to the above-mentioned materials, the elongation of each at 10 lbs force is approximately as follows: (1) GLS 230-176 (Shore A-42)-14.35% to 16.42%; (2) Exact 8203 (Shore A=40)-17.87 to 19.43%; (3) GLS 230-174 (Shore A=30)-81.67% to 83% (about 9 to 9.5 lbs force); and (4) Dynaflex G2706 (Shore A=30)-76.85 to 104.95%. In addition, the Vicat softening point or temperature for Engage 8400 is about 41° C., and for Exact 8203 is about 51° C.

As described further below, the currently preferred embodiment of the needle employed to penetrate the stoppers preferably defines a conically-pointed, non-coring tip (i.e., a "pencil point" tip), wherein the included angle of the tip in cross-section is within the range of about 15° to about 25°, preferably about 18° to about 22°, and most preferably about 20°. The smooth, sharply-pointed, gradually increasing angle of the needle tip allows for a relative smooth, and gradual expansion of the needle hole upon penetrating the stopper. Further, the memory of the preferred thermoplastic blends cause the needle hole to substantially close on itself upon withdrawing the needle therefrom, thus reducing the requisite area of impingement by the laser beam for resealing, and reducing cycle time. In addition, this further reduces the possibility of contaminating the interior of the vial between needle filling and laser resealing. If desired, the stopper surface may be Teflon coated or otherwise coated with a low-friction material to further reduce friction, and thus the formation of particles, at the needle/stopper interface. The needle tip further defines axially oblong flow apertures on opposite sides of the needle relative to each other. In the currently preferred embodiment, the needle is about 15 gage (i.e., 0.072 inch diameter).

Preferably the needle/stopper interface is treated to reduce the degree of friction therebetween to further reduce the formation of particles during the needle stroke. In one embodiment, the needle is tungsten carbide carbon coated. In another embodiment, the needle is electro-polished stainless steel. In another embodiment, the needle is Teflon coated (although this embodiment gave rise to greater friction forces at the needle/stopper interface than did the tungsten carbide carbon coated embodiment). In yet another embodiment, the needle is titanium coated to reduce friction at the needle/stopper interface. Further, in some embodiments, the depth of stroke of the needle is set to further reduce the formation of particles. In one such embodiment, at the bottom of the needle stroke, the needle flow apertures are spaced below the bottom wall of the stopper and adjacent or contiguous thereto (i.e., the upstream end of each hole is adjacent to the inside surface of the bottom wall of the stopper). In one such embodiment, the needle tip penetrates beyond the inside surface of the bottom wall of the stopper to a depth within the range of about 1 to about 5 cm, preferably within the range of about 1 to about 3 cm, and most preferably about 1.5 centimeters.

Each of the vials may be made of any of numerous different materials that are currently, or later become known for making vials or other dispensers employing the resealable stoppers herein described. For example, in some embodiments, the vials are made of glass. In other currently-preferred embodiments, the vials are made of a thermoplastic material, such as the thermoplastic material sold under the trademark TOPAS by Ticona Corp. of Summit, N.J. In some embodiments, the TOPAS material is sold under any of the following product codes: 5013, 5513, 6013, 6015, and 8007, and is a cyclic olefin copolymer and/or cyclic polyolefin.

As may be recognized by those skilled in the pertinent art based on the teachings herein, the specific formulations of the polymeric compounds used to form the stoppers and the vials or other containers of the present disclosure can be changed as desired to achieve the desired physical characteristics, including sorption (both absorption and adsorption), and moisture-vapor transmission ("MVT"). For example, the wall thicknesses of the vials and/or stoppers can be increased or otherwise adjusted in order to provide an improved or otherwise adjusted MVT barrier. Alternatively, or in conjunction with such measures, the blend of components forming the thermoplastic compounds may be changed as desired to meet desired sorption levels with the particular product(s) to be contained within the vial, and/or to achieve desired MVT characteristics. Still further, in those embodiments of the resealable stopper employing multiple layers of fusible and infusible materials, the relative thickness of the different materials can be adjusted to, in turn, adjust the MVT characteristics of the stopper. As also may be recognized by those of ordinary skill in the pertinent art based on the teachings herein, the above-mentioned numbers and materials are only exemplary, and may be changed as desired or otherwise required in a particular system.

One advantage of the preferred embodiments herein described is that the resealable portion 126, 226, 1012, 1112 of the cap or stopper may be resealed following the deposit of medicament into the chamber, thereby rendering the end cap of the invention particularly suitable for use with preservative-free medicaments, such as preservative-free vaccines. Accordingly, a further advantage is that the medicament need not contain a preservative, and therefore the above-described drawbacks and disadvantages of such preservatives can be avoided.

Another advantage of the preferred embodiments is that the medicament within the resealed chamber is not contaminated or otherwise affected by impurities or other agents in the atmosphere where the vial is stored or transported.

Another advantage is that all components of the vial may be molded from thermoplastics or other plastic materials, thus facilitating the manufacture of significantly safer, sterile, pyrogen free vials in comparison to the prior art. For example, the stoppers and vials can be molded in machines located side-by-side (or otherwise in close proximity to each other), wherein each molding machine is located tinder a laminar flow hood (or both machines are located under the same laminar flow hood), Then, the stoppers are assembled and sealed to the respective vials (or vice versa) promptly after molding (and while still hot or at a bactericidal temperature) under the laminar flow hood by, for example, a suitable assembly fixture wherein a plurality of stoppers are brought into engagement with a plurality of vial bodies (or vice versa), or by a pick-and-place robot. As a result, the interiors of the sealed vials are sterile and pyrogen free promptly upon being molded substantially without risk of contamination. The locking members also can be assembled to the vial bodies and stoppers at this time under the laminar flow hood, or can be assembled at a later time, if desired.

Figure 16:
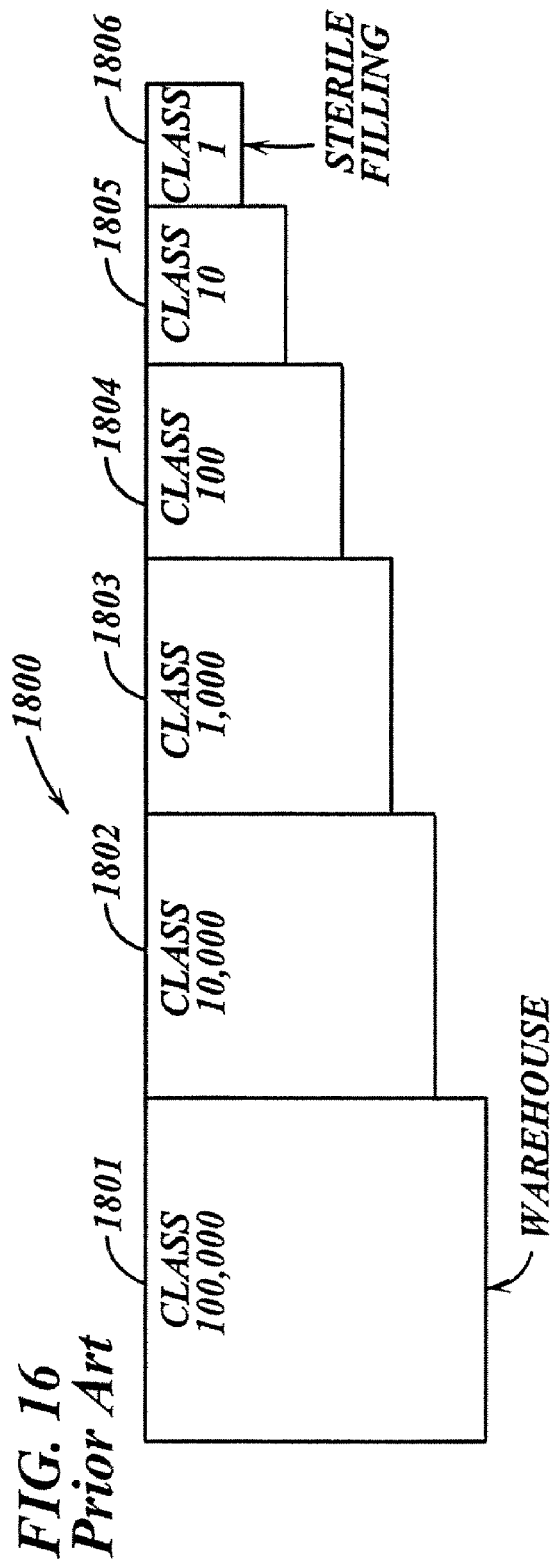
FIG. 16 is representation of a conventional facility and method for sterile filling of medicaments intended for intravenous injection or other sterile substances.

FIG. 16 is representation of a conventional facility and method 1800 for sterile filling of medicaments intended for intravenous injection or other sterile substances. The conventional facility and method employs a first area (e.g., a warehouse of class 100,000) for receiving medicament and containers (e.g., vials and caps) to be filled. The facility and method further employs a series of progressively "cleaner" areas 1802-1806, including an area 1806 (e.g., a class I area) where the containers are sterilized, filled, and sealed.

Figure 17:
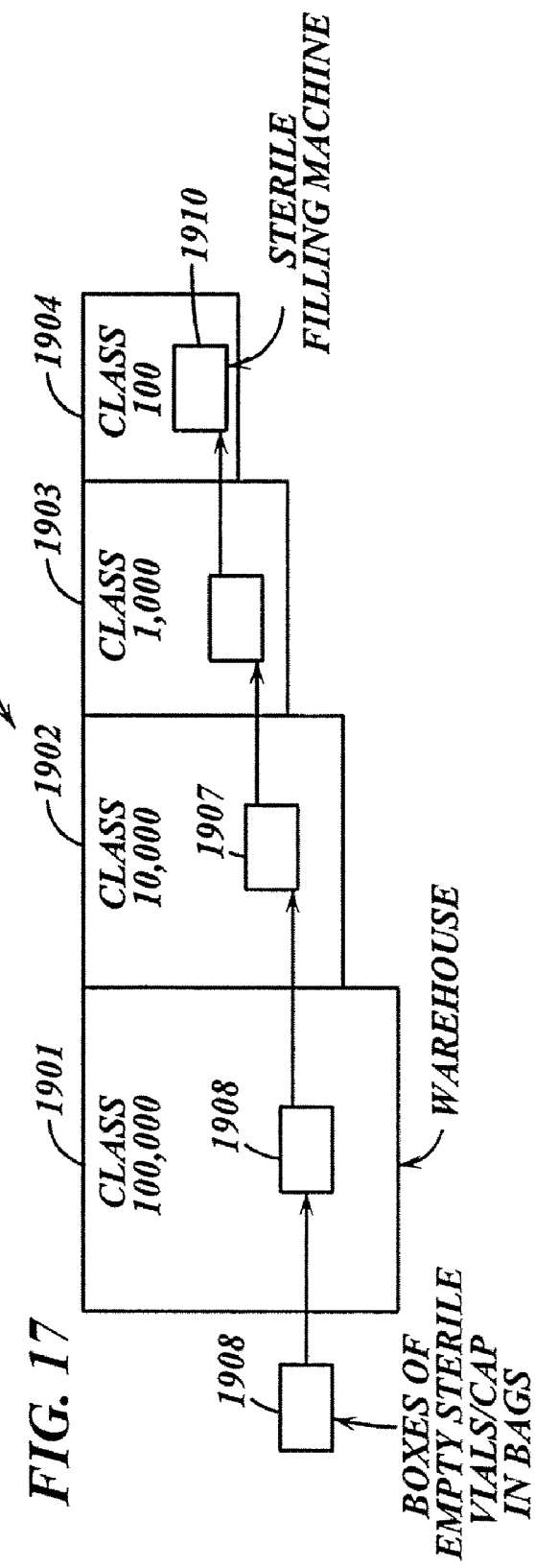
FIG. 17 is representation of a facility and method for sterile filling of medicaments or other sterile substances.

FIG. 17 is representation of a facility and method 1900 for sterile filling of medicaments. The facility and method 1900 includes a first area (e.g., a warehouse of class 100,000) for receiving medicament and bags 1907 containing trays of sealed, sterile containers (e.g., vials and caps) to be filled with medicament. Various tray-container arrangements are shown in FIGS. 29A-C. The facility and method further employs a series of progressively "cleaner" areas 1902-1904, including an area 1904 (e.g., a class 100 area) where a filling machine 1910 for sterile filling (of the sterile sealed containers) is located, sometimes referred to hereinafter as a "sterile filling machine". The bags 1907 containing the trays of containers may arrive packed in boxes 1908 to help keep the sealed bags 1907 clean and undamaged.

In some embodiments, each tray of containers arrives double or triple bagged rather than single bagged. The bagged trays of containers may, for example, be removed from the boxes in the area 1901. The bagged trays of containers are thereafter transported through progressively "cleaner" areas 1902-1904 until reaching the sterile filling machine 1910. If the trays of containers are double or triple bagged, one or two of the bags may be removed prior to reaching the sterile filling machine 1910. The tray of sealed sterile containers is thereafter transferred from the remaining bag to the sterile filling machine 1910 to be filled with medicament and resealed.

In another embodiment, containers arrive prior to being sterilized and are thereafter sterilized, sealed, and bagged within the facility 1900 and then transported to the sterile filling machine 1910 for filling and resealing. Either of the two above embodiments may employ one or more of the methods described above for transporting sealed sterile containers. In addition, the sterile filling machine may employ an e-beam, laser sterilization, and/or other type of pre-sterilization unit to sterilize at least the penetrable surfaces of the resealable stoppers prior to needle penetration, filling and laser resealing, as otherwise described herein.

One advantage of the facility and method 1900 shown in FIG. 17 as compared to the facility and method 1800 shown in FIG. 16 is that the facility and method 1900 shown in FIG. 17 allow sterile filling without the need for the class 10 area 1805 and the class 1 area 1806.

Figure 18:
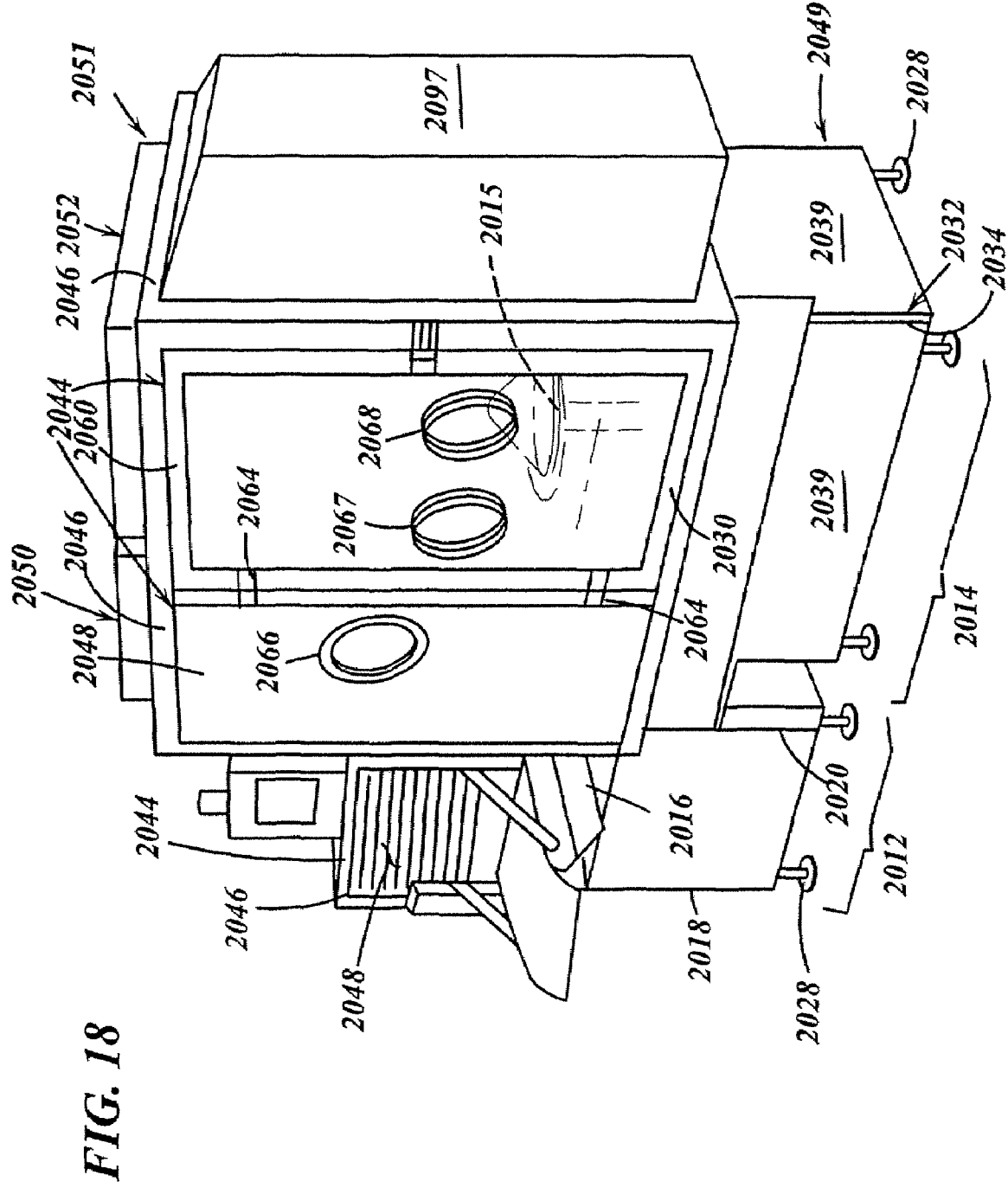
FIG. 18 is a perspective view of a filling machine.
Figure 19:
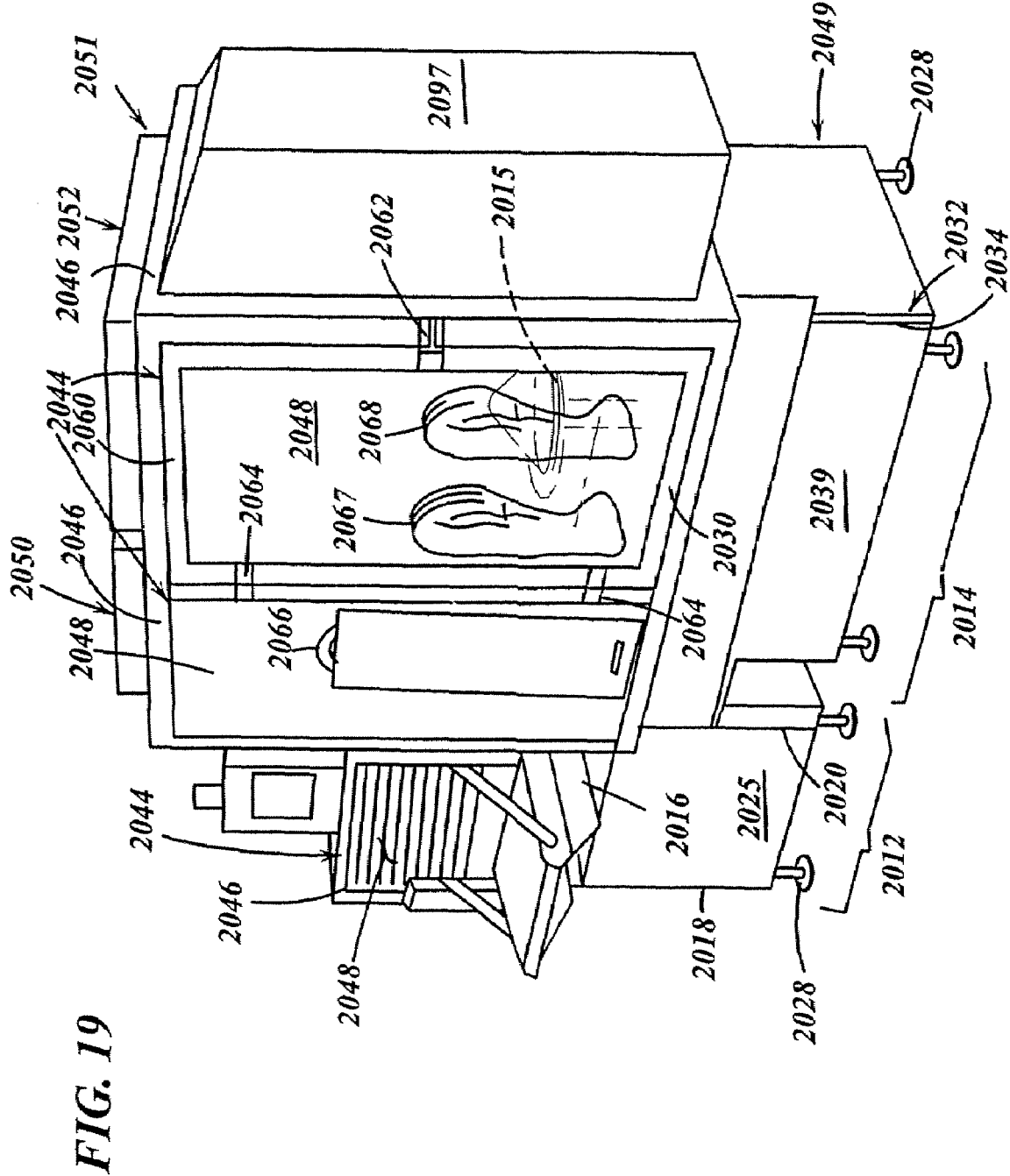
FIG. 19 is a perspective view of the filling machine of FIG. 18 including a pair of gloves mounted to the glove ports for allowing a user to access the interior of the filling machine, and a bag defining a sterile enclosure mounted to the sterile transfer port for transferring articles into and out of the sterile or aseptic interior of the filling machine.
Figure 20:
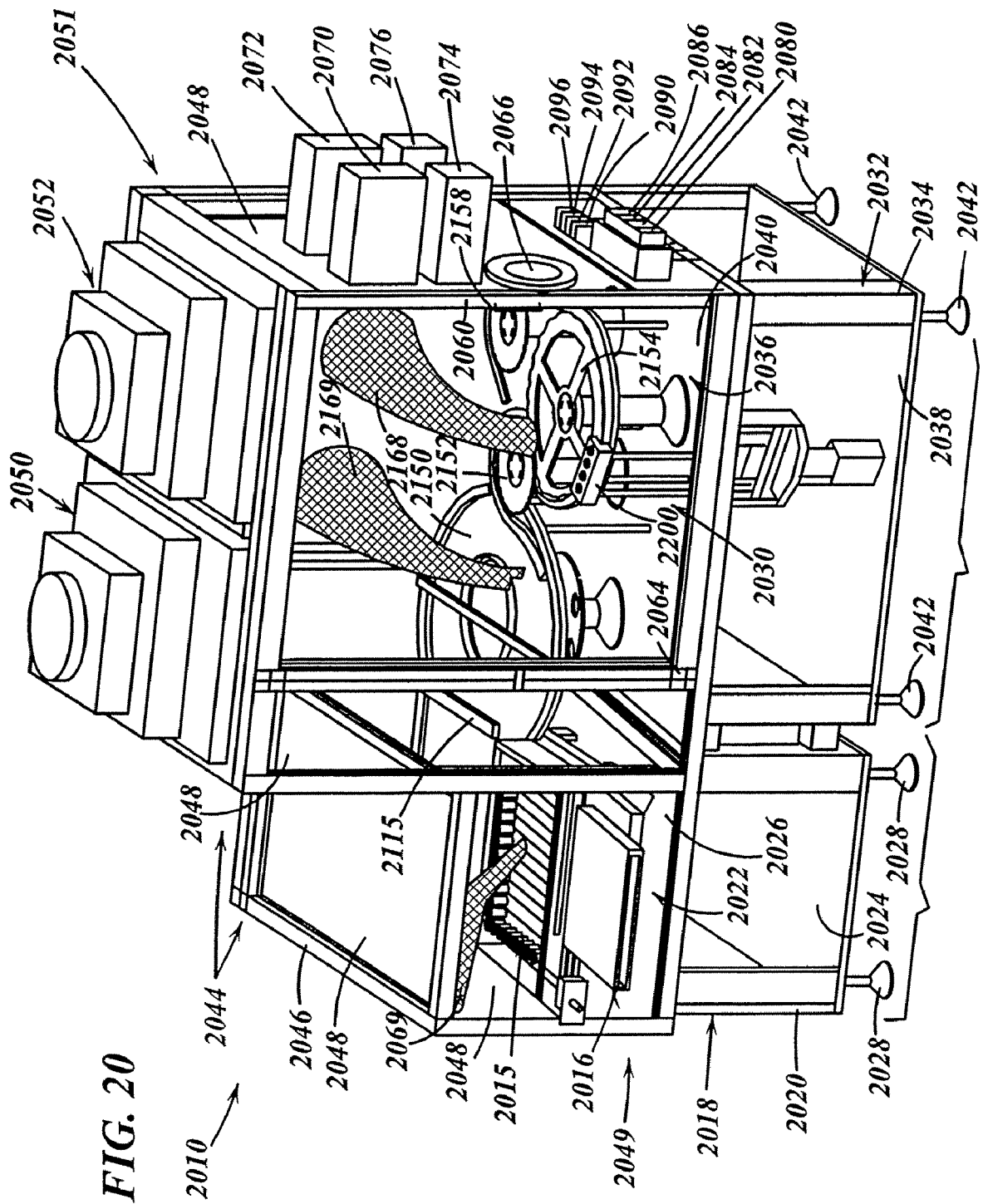
FIG. 20 is a perspective, somewhat schematic view of the filling machine of FIGS. 18 and 19.
Figure 21:
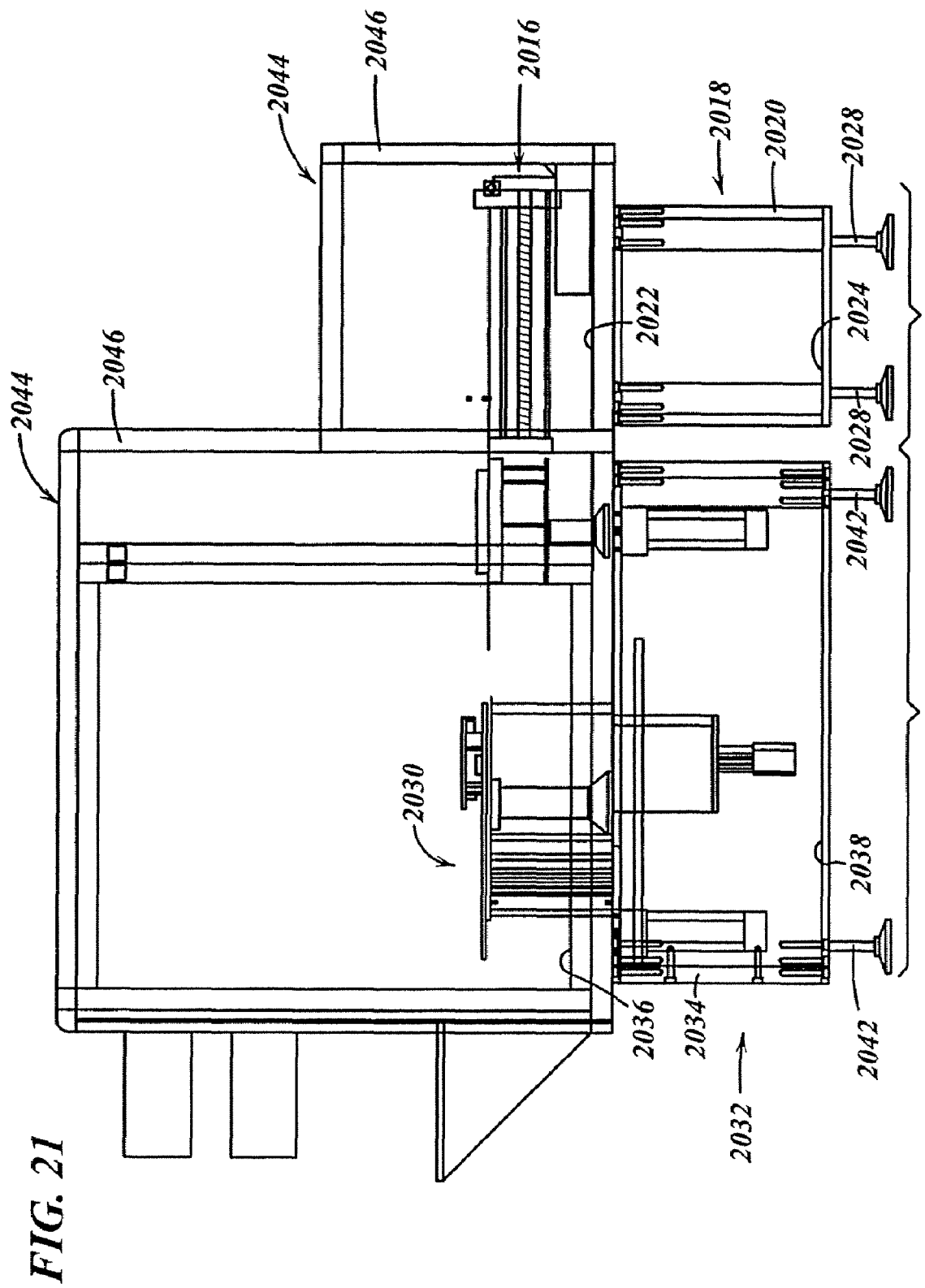
FIG. 21 is a somewhat schematic, partial, cross-sectional view of the filling machine of FIGS. 18-20 with some parts removed for clarity.

FIGS. 18-20 are perspective views of a sterile filling machine 2010. The filling machine 2010 may, for example, be used to introduce medicament though a resealable cap on a cap/vial assembly, and to thereafter reseal the cap. Other embodiments of the filling machine 2010 may be used to fill and seal other types of containers (including but not limited to other types of vials or syringes), that may have resealable caps or stoppers that are the same as or different than those described above, with medicament or other substance(s) such as, for example, but not limited to, cosmetics or food products.

In this embodiment, the filling machine 2010 has an infeed unit 2012 and a fill unit 2014. As will be further described hereinafter, the infeed unit 2012 receives the containers (e.g., the vials, syringes or other containers) that are to be filled, and thereafter supplies the containers to the fill unit 2014, which in turn fills the containers. An example of a plurality of containers to be filled and sealed by the filling machine 2010 are shown at 2015 (FIG. 20).

The infeed unit 2012 includes an infeed assembly 2016 and an infeed support structure 2018. Further details of the infeed assembly 2016 are described hereinafter with respect to FIGS. 24, 25, 26A-26B, 27 and 28A-28I. As shown in FIG. 20, the infeed support structure 2018 includes a frame 2020, two plates 2022, 2024 joined thereto, and side panels 2025 connectable to the frame to enclose the interior thereof (FIGS. 18 and 19). More particularly, as shown in FIG. 20, the upper plate 2022 is joined to an upper portion of the frame 2020. The lower plate 2024 is joined to a lower portion of the frame 2020. The upper plate 2022 has an outwardly facing surface 2026 that supports the infeed assembly 2016. The lower plate 2024 has feet 2028 mounted thereto. The feet 2028 may have any form including but not limited to casters (as shown), wheels, or any combination thereof.

The fill unit 2014 includes a fill assembly 2030 and a fill support structure 2032. Further details of the fill assembly 2030 are described hereinafter with respect to FIGS. 21-25, 26A-26B, 30A-30F, and 31A-31H. As with the support structure of the infeed unit, and as shown in FIG. 20, the support structure of the fill assembly includes a frame 2034, two plates 2036, 2038, and side panels 2039 connected thereto (FIGS. 18 and 19). As shown in FIG. 20, the upper plate 2036 is joined to an upper portion of the frame 2034. The lower plates 2038 is joined to a lower portion of the frame 2034. The upper plate 2036 has an outwardly facing surface 2040 that supports the fill assembly 2030. The lower plate 2038 has feet 2042 mounted thereto. The feet 2042 may have any form including but not limited to casters (as shown), wheels, or any combination thereof.

Figure 28:
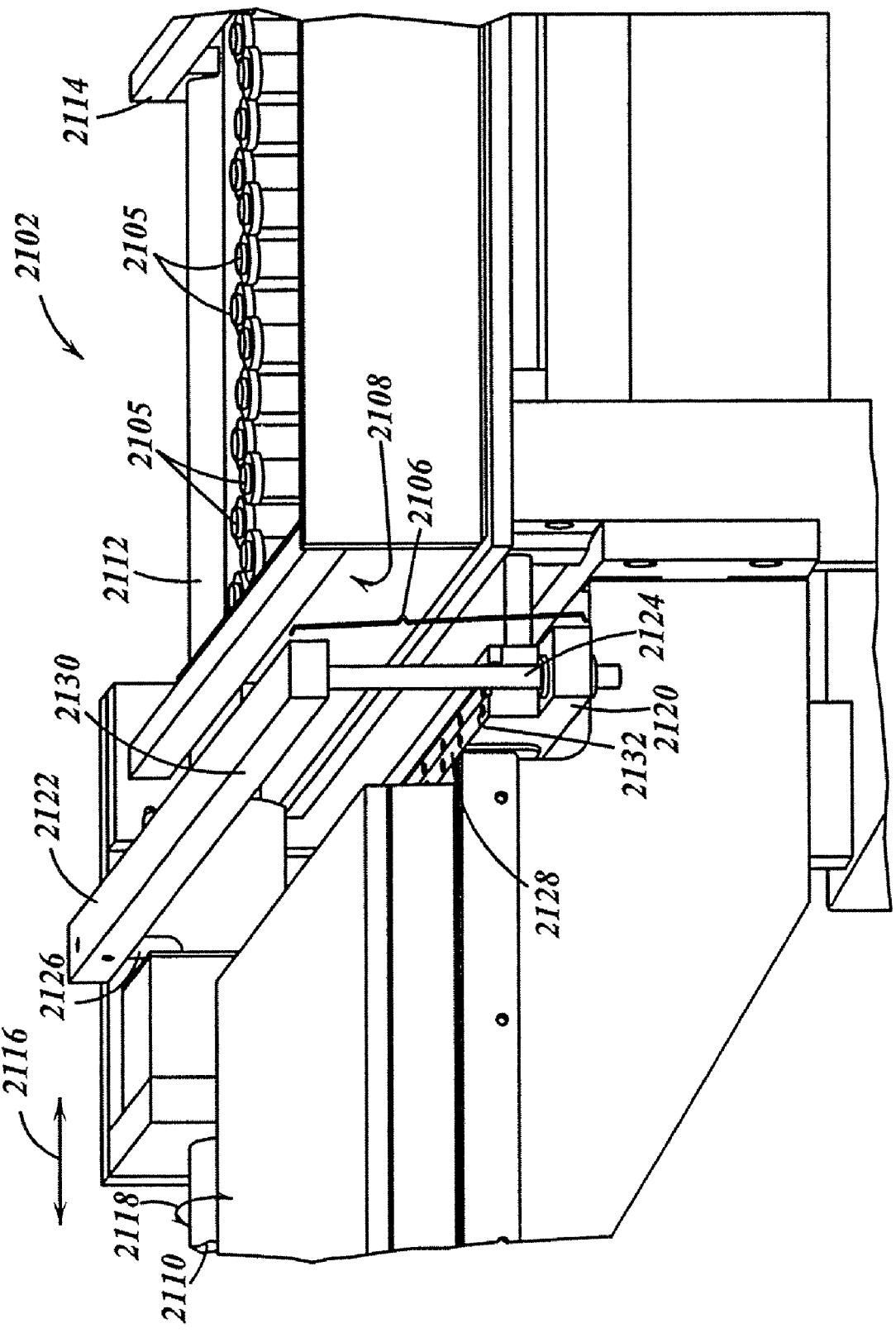
FIG. 28 is a further enlarged, partial, perspective view of a portion of the infeed unit of FIG. 27.
Figure 28A:
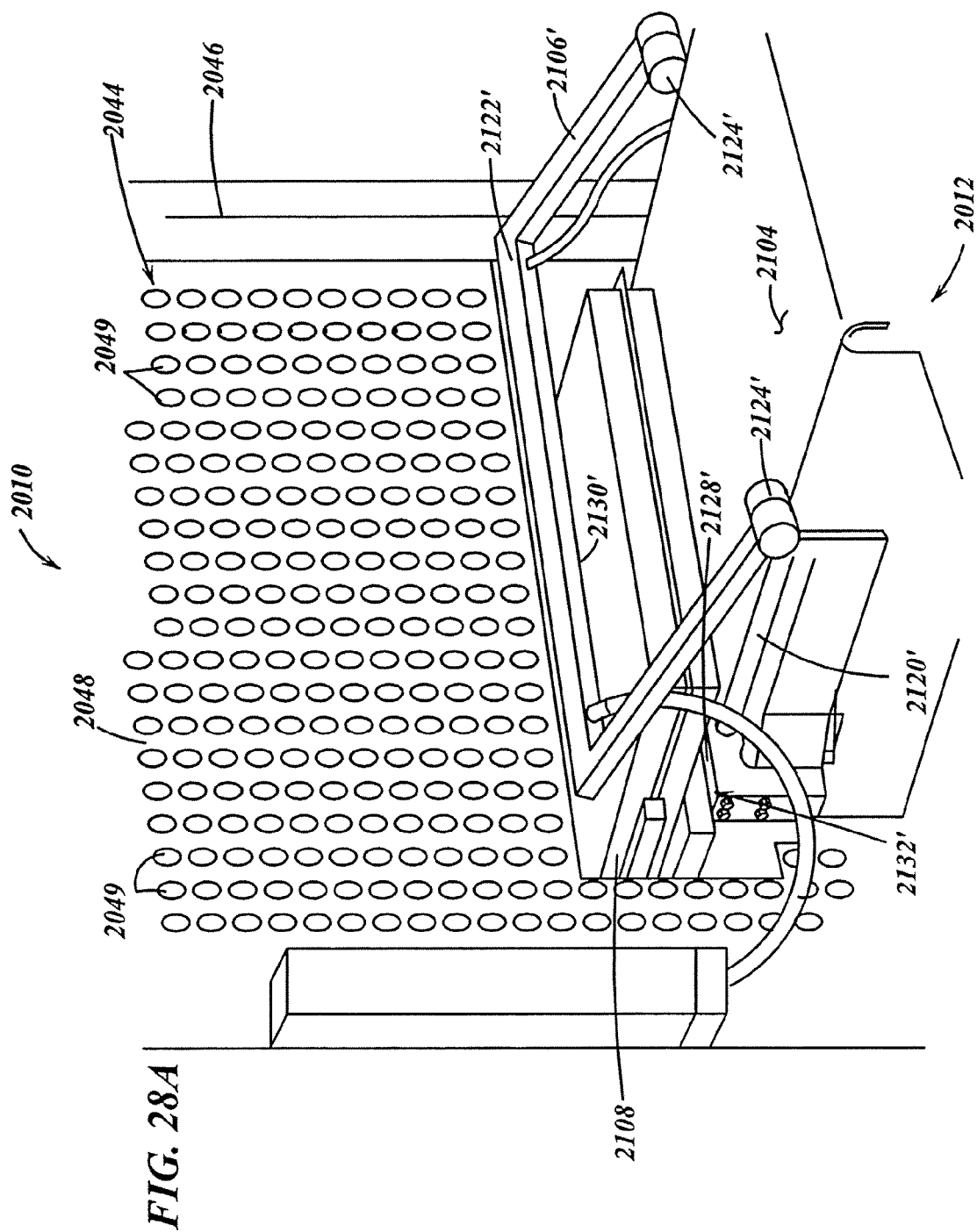
FIGS. 28A-28I are partial, perspective views of an alternative embodiment of the infeed unit of the filling machine of FIGS. 18-20 showing progressively the infeeding of a tray of vials into the infeed unit and, in turn, onto the turntable of the filling unit of the sterile filling machine.

The filling machine 2010 further includes a barrier 2044 that restricts movement into and out of the filling machine. In this embodiment, the barrier 2044 includes a frame 2046 and walls 2048 (or panels) supported thereby. One or more of the walls 2048 may be transparent, or at least somewhat transparent, to provide visibility into the filling machine. In such instance, the transparent wall(s) may be adapted to limit the transmissibility of particular wavelengths, so as to reduce the possibility that emissions from any lasers within the filling machine could accidentally cause harm to people in the vicinity of the filling machine. This may be carried out, for example, by tinting. As shown in FIGS. 18 and 28A, the infeed unit barrier 2048 may includes a plurality of apertures 2049 spaced relative to each other throughout the respective panel of the barrier in order to allow the laterally or horizontally directed laminar flow to exit the aseptic enclosure of the infeed unit therethrough.

The barrier 2044 can be viewed as having a base portion 2049 and an upper portion 2051. The base 2049 is connected to the support structures 2018, 2032 by way of support members (not shown). The upper portion 2051 supports blower assemblies 2050, 2052. Each of these blower assemblies 2050, 2052 includes a filter and a fan to produce a filtered airflow into the filling machine. This filtered airflow causes the air pressure within the barrier 2044 to be somewhat greater than the air pressure outside the barrier 2044. This pressure differential helps minimize the possibility of airflow into the filling machine 2010, which in turn helps prevent (or at least limit) the possibility that contaminants will get into the filling machine 2010. In some embodiments, the filter is a high efficiency filter such as, for example, a HEPA filter.

The base 2049 of the barrier 2044 and the support structures 2018, 2032 are shaped and dimensioned so as to define clearances therebetween. For example, in the illustrated embodiment, the clearances are in the form of an approximately three inch gap between the periphery of the base and the perimeter of the support structures 2018, 2032. These clearances, or vents, define a flow path through which the filtered airflow provided by the blower assemblies 2050, 2052 exits the filling machine 2010. The barrier 2044, blower assemblies 2050, 2052, vents, and structures located within the barrier 2044 are preferably designed so as to help ensure that the filtered airflow has laminar flow characteristics, or at least generally laminar flow characteristics (as opposed to turbulent flow characteristics), until exiting the filling machine 2010. The laminar flow characteristics help keep contaminants from entering the filling machine through the vents and help clear out any dust or contaminants that happen to get into the filling machine 2010, and thereby help maintain a "clean" environment within the filling machine 2010.

The barrier 2044 is provided with one or more doors, e.g. door 2060, which can be opened to access the area within the barrier 2044. In this embodiment, the door 2060 includes a lock and handle 2062 and is affixed to the frame of the barrier via hinges 2064. Notwithstanding, it should be recognized that opening the door 2060 creates an opportunity for contaminants to enter the filling machine 2010 from outside the barrier 2044. Thus, it is generally undesirable to open the door 2060 after the initial set up of the filling machine 2010. For this reason, the barrier 2044 is provided with a transfer port 2066 and glove ports 2067-2069. The transfer port 2066 is of a type known to those of ordinary skill in the pertinent art and allows materials to be introduced into the filling station without the need to open the door 2060 of the barrier 2044. For example, the transfer port can be used to remove old tubing and install fresh, sterile tubing between the pumps and needles between filling operations. Glove ports 2067-2069 allow an operator to perform operations within the filling machine 2010, without the need to open the door 2060. For example, the glove ports may be used to open and close the interior door of the transfer port 2066, and to remove the old tubing and install fresh tubing between the pumps and needles between fill operations. The glove ports 2067-2069 may be provided with sensors that produce a signal when an operator has his or her hands in the glove ports. Alternatively, a light or other radiation beam or curtain can be provided between the glove ports and interior portions of the filling machine to sense movement of the gloves and produce a signal in response thereto that can either warn the operator or terminate operation of the machine. In order to prevent injury to the operator, the signal may be used to initiate a shut down of the filling machine 2010 until the sensor determines that the operator's hands are removed from the glove ports 2067-2069. In sonic embodiments, the barrier 2044 includes a wall 2071 (FIG. 28A) that limits airflow between the infeed unit 2012 and the fill unit 2014.

The filling machine 2010 further includes a plurality of pumps 2070, 2072, 2074, 2076 (FIGS. 20 and 30F), a bank of laser sources 2080, 2082, 2084, 2086 (FIG. 20), and a bank of IR sensor detector modules 2242, 2244, 2246, 2248 (FIGS. 36 and 37A-37D), which are further discussed hereinafter. As shown in FIGS. 18 and 19, a cabinet 2097 is mounted on one side of the barrier 2044 and encloses the pump, laser sources and other electronic components or devices mounted therein.

In some embodiments, it may be desirable to provide means for fogging the interior of the filling machine 2010 with a chemical to help eliminate contaminants when the filling machine is initially set up, at some selected points in time thereafter, and/or after some types of events that would require such fogging.

Figure 24:
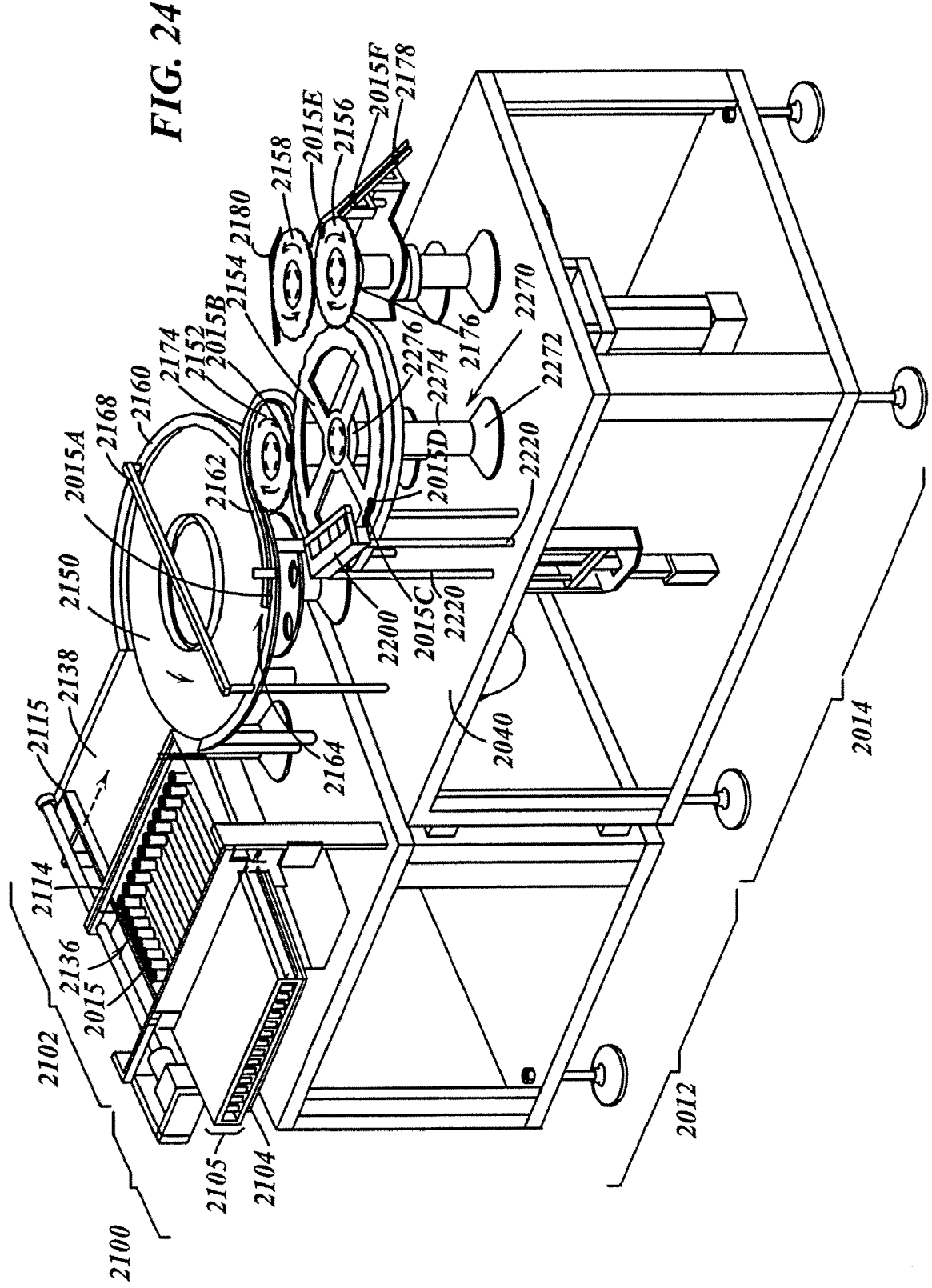
FIGS. 24, 25, 26A and 26B are enlarged perspective views of the infeed unit and the fill unit of the filling machine of FIGS. 18-20, shown without the barrier portion.
Figure 25:
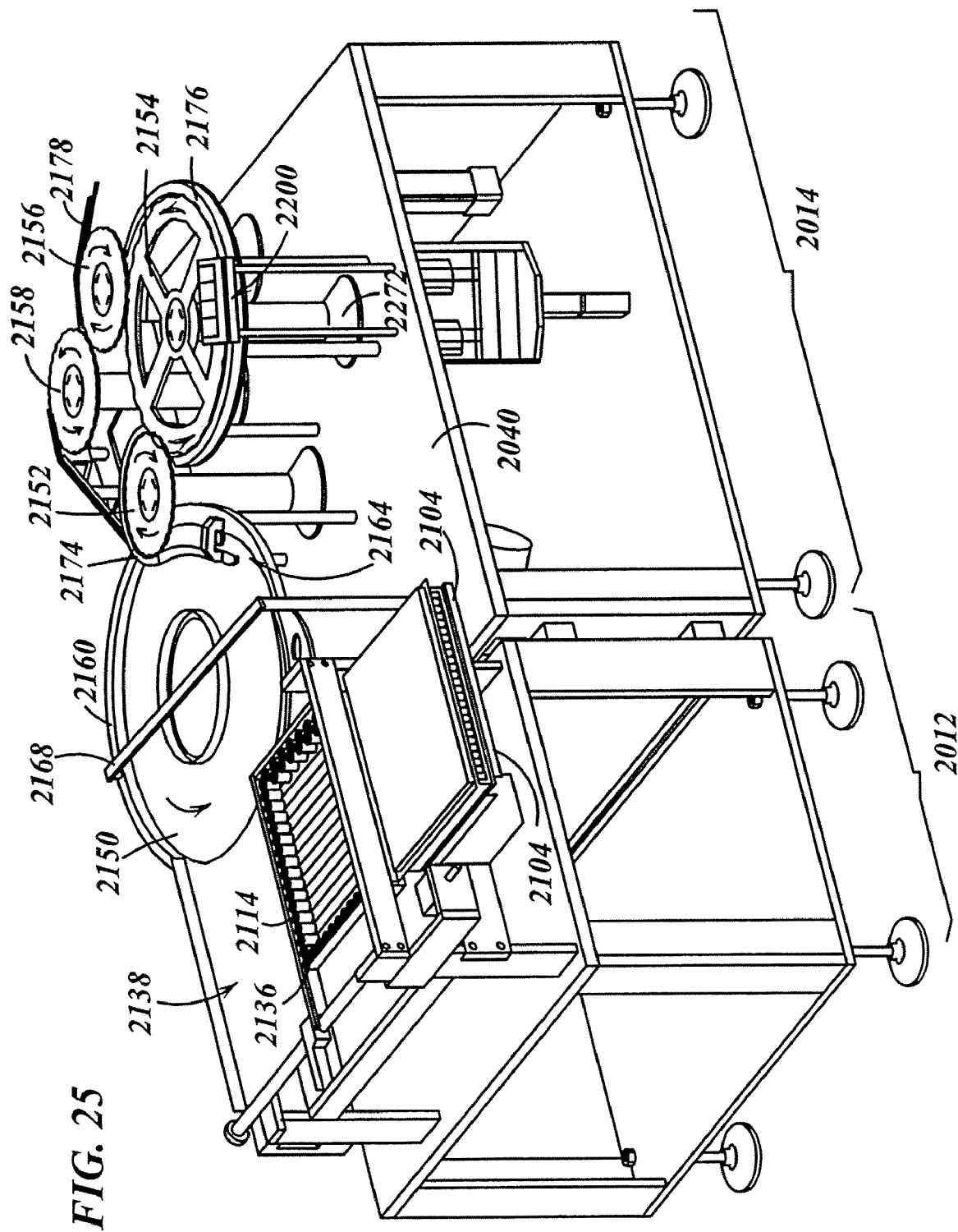
Figure 26A:
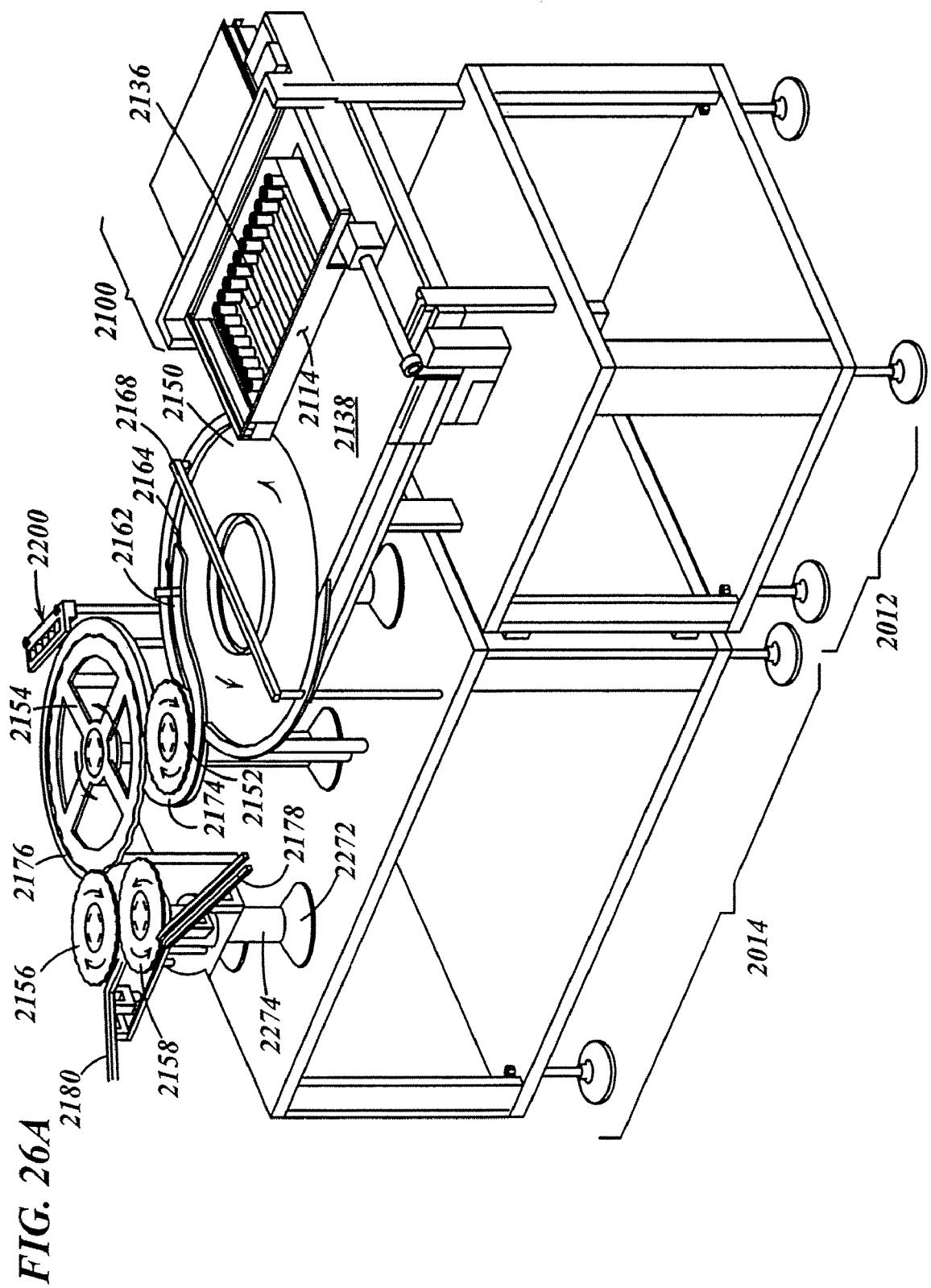
Figure 26B:
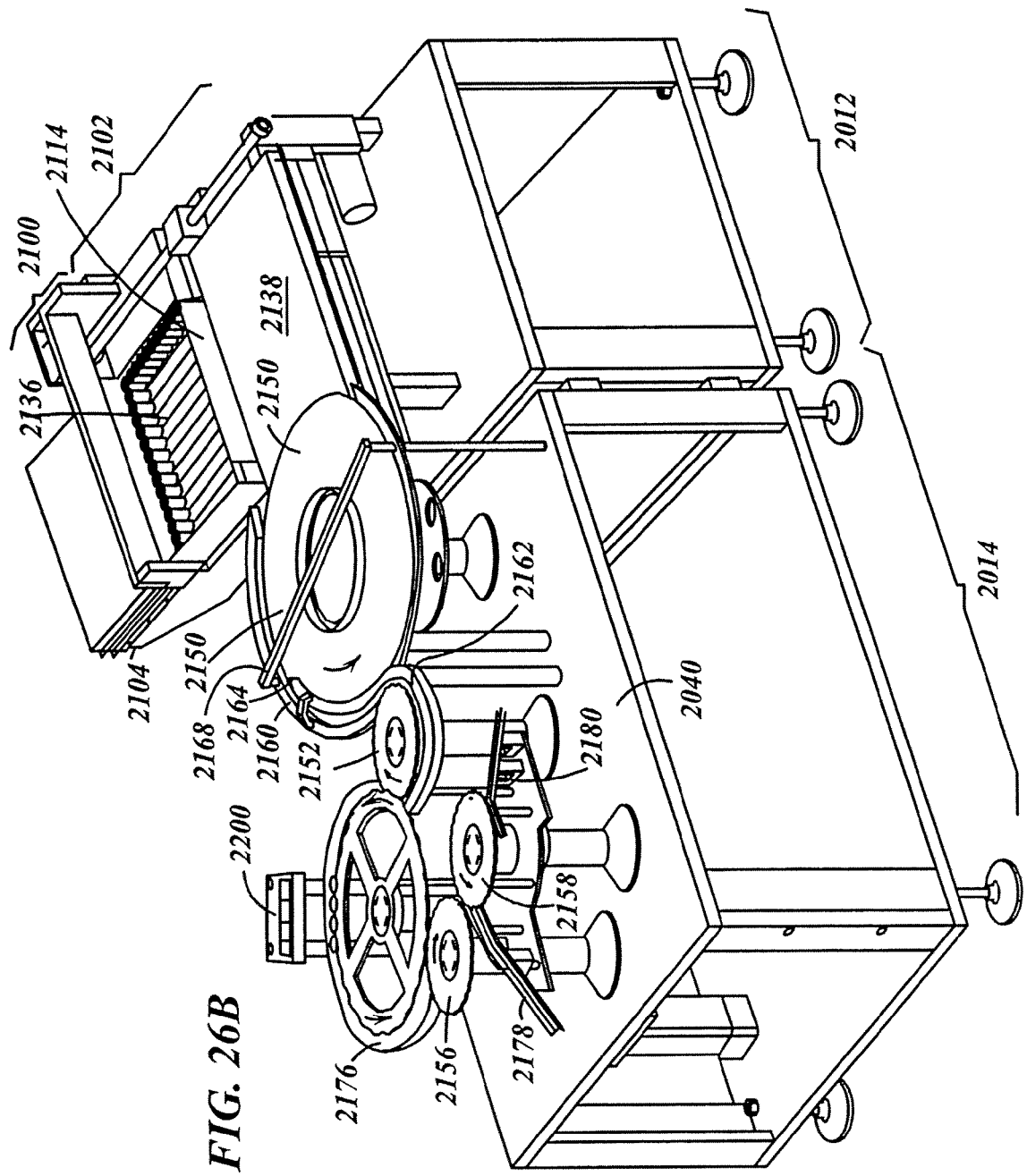
Figure 27:
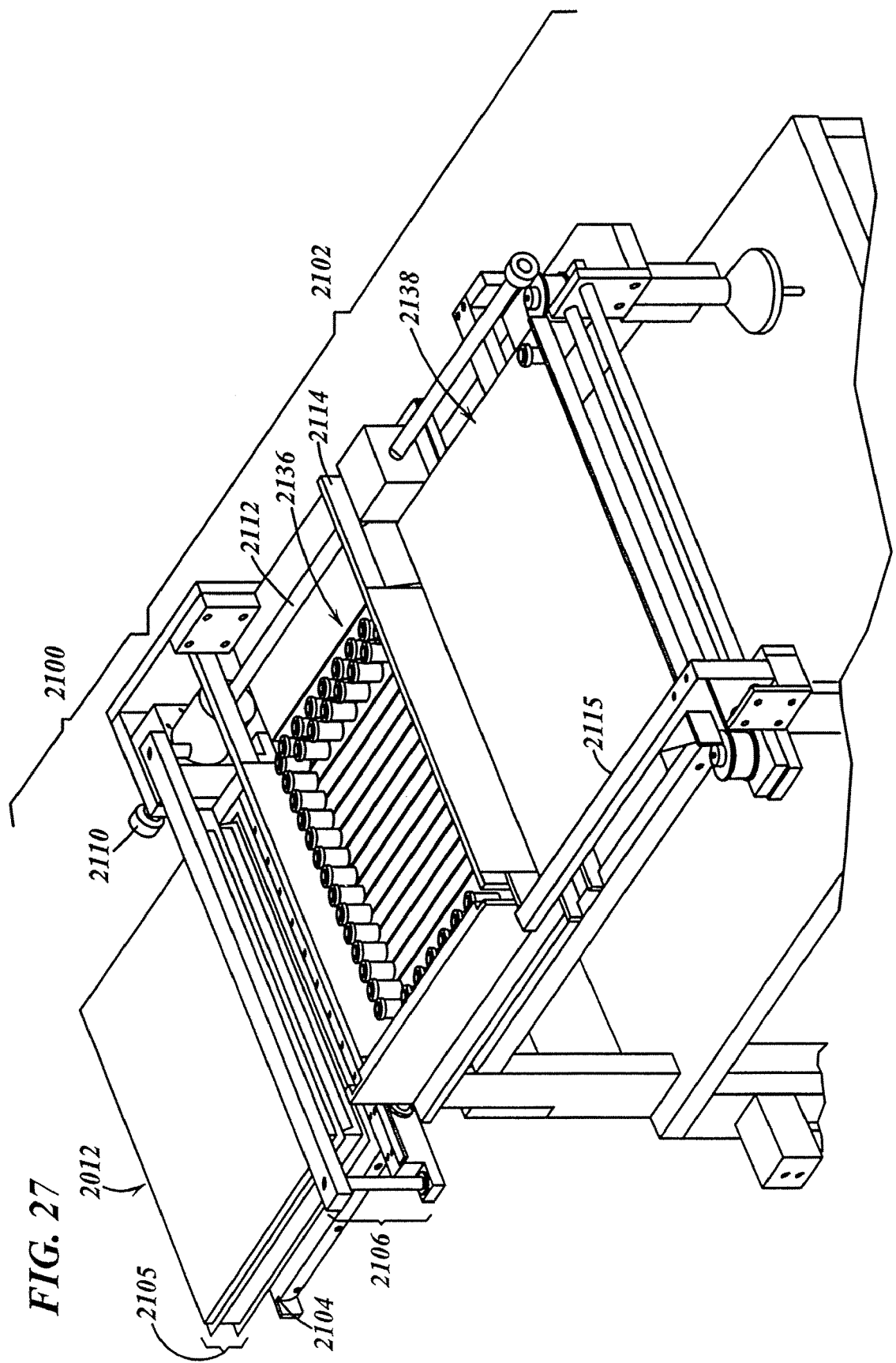
FIG. 27 is a further enlarged, partial, perspective view of the infeed unit of FIG. 26.
Figure 29:
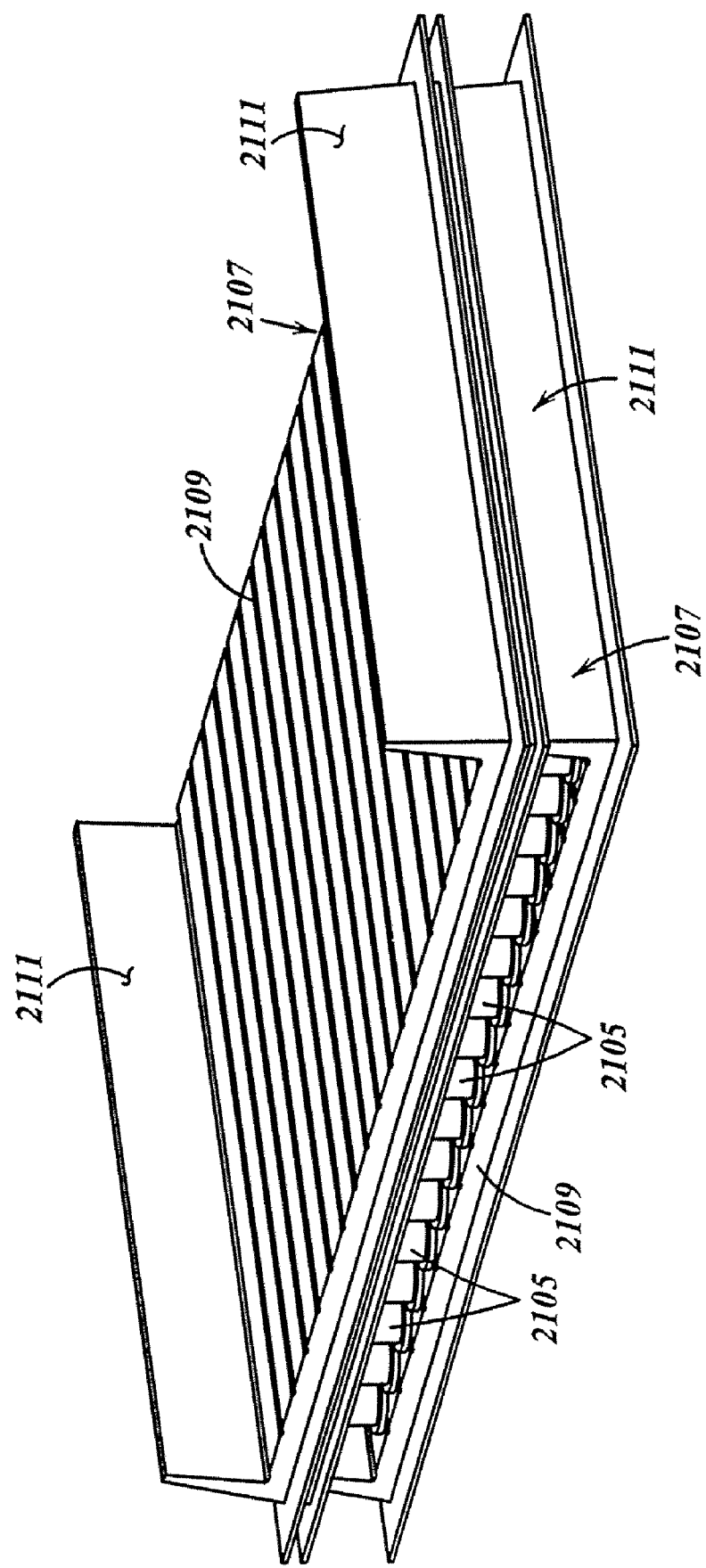
FIG. 29 illustrates another embodiment of a tray arrangement that may be used to load vials or other containers into the infeed unit.

Referring to FIG. 24, the infeed unit 2012 includes a first portion 2100 that resides outside of the barrier 2044 and a second portion 2102 that resides inside the barrier 2044. Referring to FIGS. 27 and 28, the first portion 2100 includes a shelf 2104, a clamp 2106, an infeed port 2108 and handle 2110. The shelf 2104 is adapted to support a bagged tray of containers prior to feeding the tray into the infeed unit. An example of a tray of a containers 2105 is shown on the surface of the shelf 2104. A lid is shown on the tray of containers 2105; however, this is not required. Another embodiment of a tray arrangement that may be used to load vials or other containers into the infeed unit 2012 is shown in FIG. 29. As can be seen, the trays 2107 are stackable, and each tray includes a base wall 2109 for supporting thereon the rows of vials, and vertically-extending end walls 2111 on opposite ends of the base wall relative to each other. The end walls 2111 are hollow such that the upper ends of the end walls of one tray may be received within the hollow base of the end walls of another tray to stack the trays of vials.

For clarity, the bag around the tray of containers is not shown in FIG. 24. The clamp 2106 (FIGS. 27-28) is adapted to help transfer the tray of containers 2105 from the first portion 2100 of the infeed unit to the second portion 2102 of the infeed unit without exposing the containers to unfiltered air from outside of the barrier. The infeed port 2108 may be shaped and dimensioned to receive the tray of containers. The handle 2110 is connected to a rod 2112, which is, in turn, connected to a first sweeper arm 2114 provided on the second portion 2102 of the infeed unit. The handle can be moved in and out (as indicated by arrows 2116 in FIG. 28) and can be turned (as indicated by arrows 2118 in FIG. 28). In some embodiments, the clamp 2106 opens by having one side of the second portion 2122 rotate upwards, rather than sliding up and down.

As shown in FIG. 28, the clamp 2106 includes two clamp portions 2120, 2122. Slidable connecting members 2124, 2126 connect the first portion 2120 to the second portion 2122. Each portion 2120, 2122 has a clamping surface 2128, 2130, respectively. Each clamping surface 2128, 2130 defines one or more vacuum ports, e.g., vacuum port 2132. The vacuum of the ports are selectively connected to one or more vacuum source(s) (not shown).

As shown in FIG. 27, the second portion 2102 of the infeed unit 2012 includes a first staging area 2136, a second staging area 2138, the first sweeper arm 2114 and a second sweeper arm 2115. As stated above, the first sweeper arm 2114 is connected to the rod 2112 which is connected to the handle 2110. This, turning the handle 2110 counter-clockwise causes the sweeper arm 2114 to rotate to a vertical position. Turning the handle 2110 clockwise causes the sweeper arm 2114 to rotate from the vertical position to the horizontal position. Moving the handle 2110 in and out in the direction of the arrows 2116 (FIG. 28) causes the sweeper arm 2114 to move back and forth between the first staging area 2136 and the second staging area 2138. More particularly, pushing the handle 2110 inward (toward the infeed unit 2012) causes the sweeper arm 2114 to move from the first staging area 2136 to the second staging area 2138. Pulling the handle 2110 outward (away from the infeed unit 2012) causes the sweeper arm 2114 to move from the second staging area 2138 to the first staging area 2136. In this embodiment, the containers are "diabolo" shaped vial/cap assemblies, as illustrated for example in FIGS. 14 and 15. One advantage of this shape is that once the vial is upright, it is fairly stable and therefore tends to remain in an upright condition and not tip over.

Figure 22:
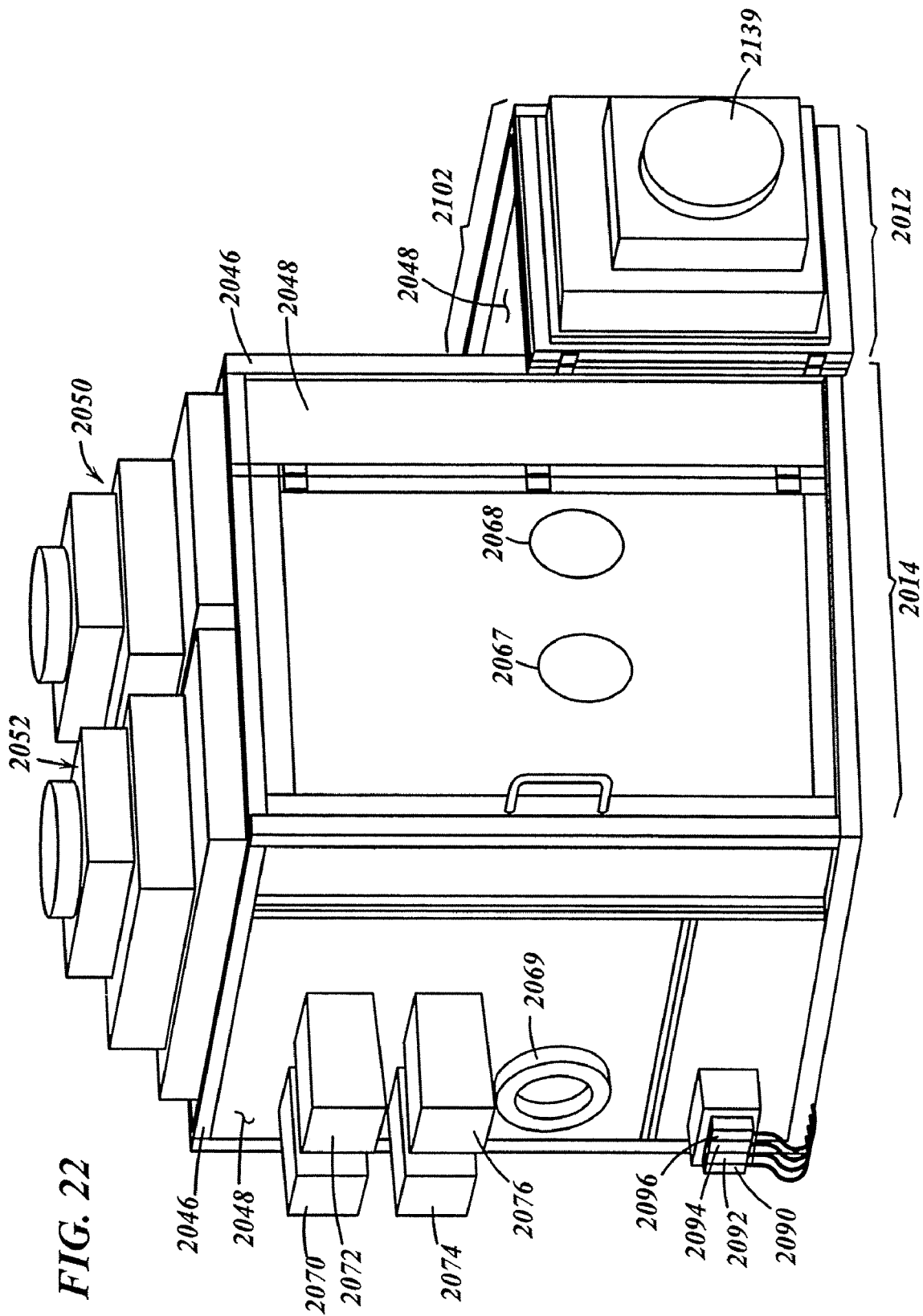
FIG. 22 is a perspective view of the barrier of the filling machine of FIGS. 18-20.
Figure 23:
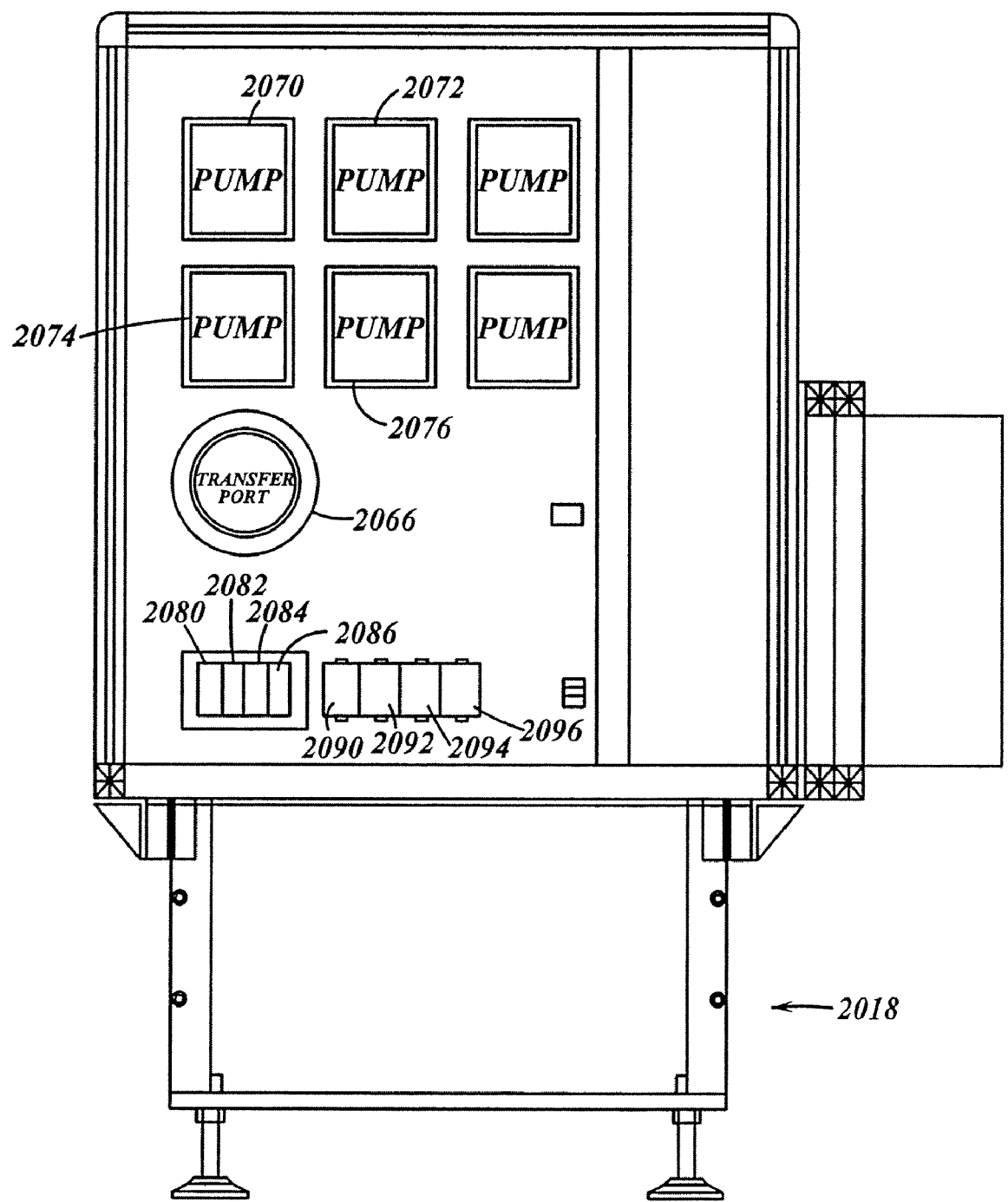
FIG. 23 is a side elevational view of the filling machine of FIGS. 18-20 with some parts removed for clarity.

The second portion 2012 of the infeed unit 2012 further includes a blower assembly 2139 (FIG. 22). The blower assembly 2139 provides a filtered airflow that exits through the infeed port 2108. The infeed unit 2102 is preferably designed so as to help ensure that the filtered airflow has laminar flow characteristics, or at least generally laminar flow characteristics (as opposed to turbulent flow characteristics), until exiting the infeed port 2108. As described above, and shown in FIG. 28A, the barrier panel 2048 on the inlet side of the infeed unit defines a plurality of apertures 2049 spaced relative to each other throughout the respective panel to allow the laminar flow to exit the infeed unit therethrough. The laminar flow characteristics help keep contaminants from entering the filling machine through the infeed port 2108 and help clear out any dust or contaminants that happen to get into the filling machine 2010, and thereby help maintain a "clean" environment within the filling machine 2010.

In an alternative embodiment of the infeed unit 2012' shown best in FIGS. 28A-28I, the upper portion 2030' of the clamp 2106' is pivotally mounted by a pair of hinges 2124' to the frame 2046. Each clamping surface 2128', 2130' includes a longitudinally extending vacuum slit 2132' (only one shown) that is coupled in fluid communication with a vacuum source for releasably securing a respective wall of the tray containing bag thereto. Thus, the second portion 2122' of the clamp 2106' is pivotable toward and away from the first portion 2120' to close and open the clamp.

Figure 28B:
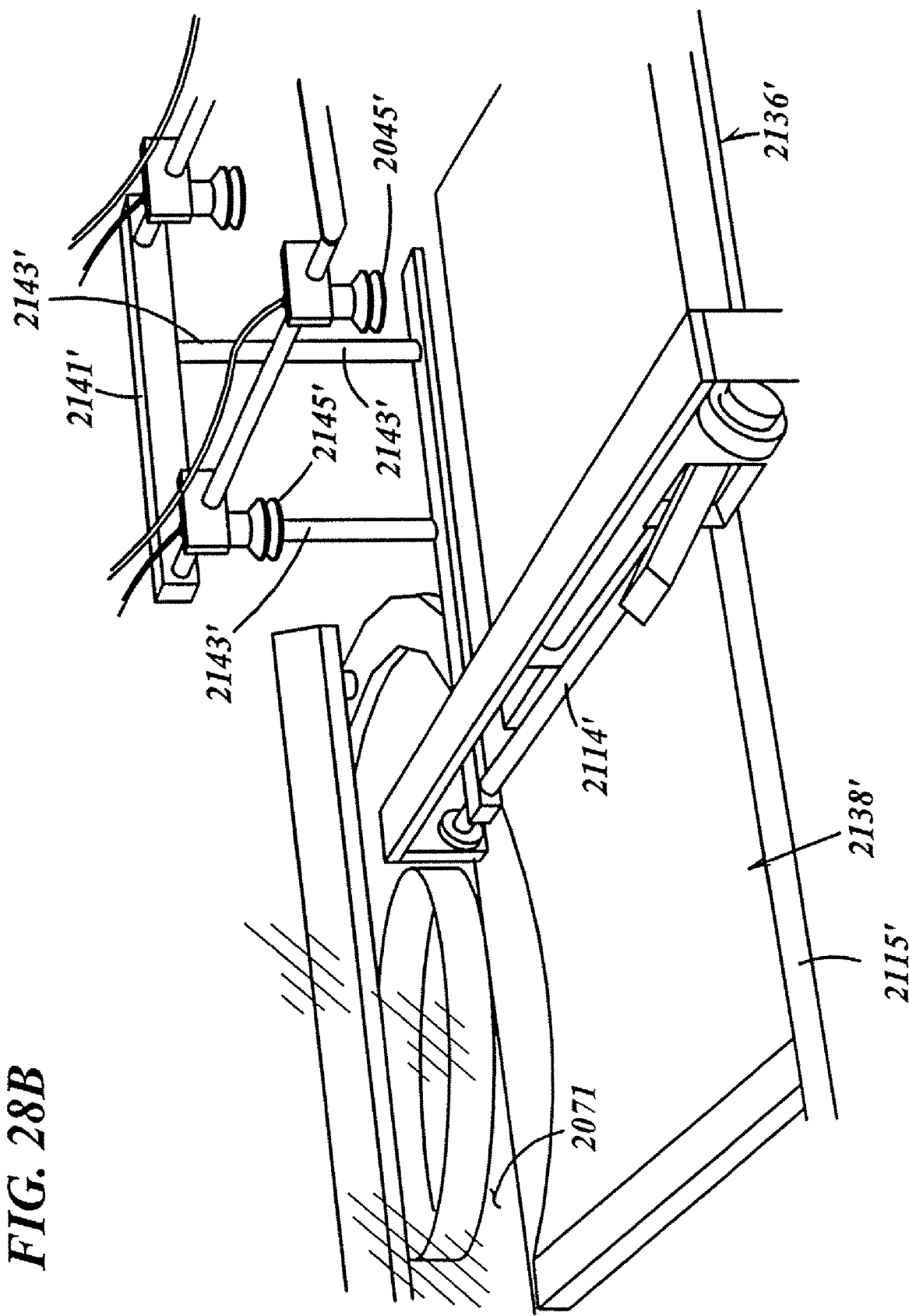
Figure 28C:
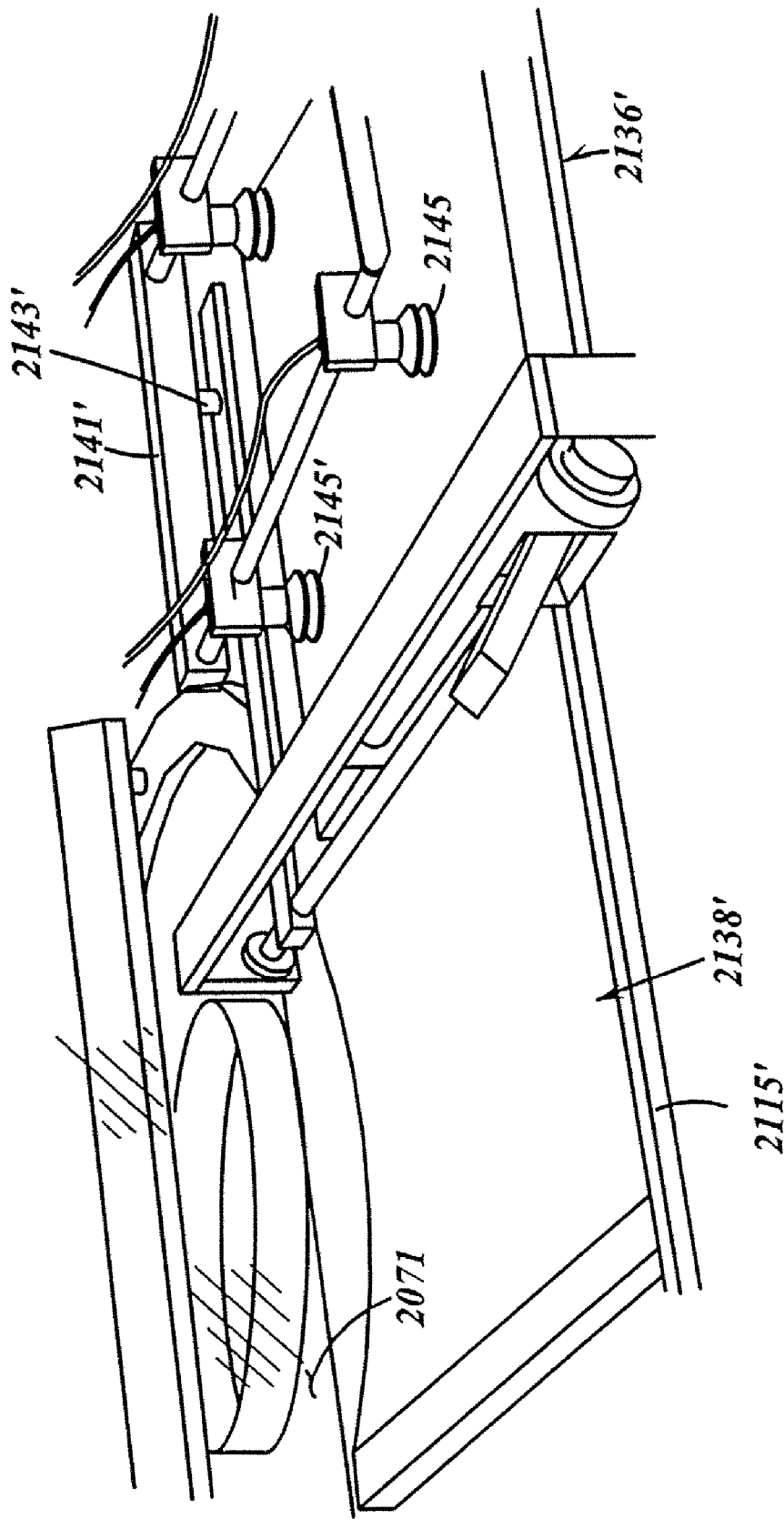

As shown in FIGS. 28B-28I, the infeed unit 2012' includes a tray lifter 2141' that is mounted on pairs of opposing drive shafts 2143' located on opposite sides of the first staging area 2136' relative to each other. The drive shafts 2143' are drivingly connected to a drive source (not shown), such as a servo-drive to move the lifter between raised and lowered positions. The lifter 2141' includes a plurality of suction cups 2145' that are coupled in fluid communication to a vacuum source and face downwardly to releasably engage the cover of the tray located within the first staging area 2136'. As shown in FIGS. 28B and 28C, the tray lifter 2141' is movable between a raised position (FIG. 28B) spaced above the tray located within the first staging area 2136' and a lowered position (FIG. 28C) with the suction cups 2145' engaging the upper surface of the tray cover and releasably securing the tray cover thereto. As shown in FIG. 28, the lifter 2141' is driven upwardly to the raised position to lift the tray cover away from the tray and vials and thereby expose the vials for removal from the tray into the second staging area 2138'.

Figure 28D:
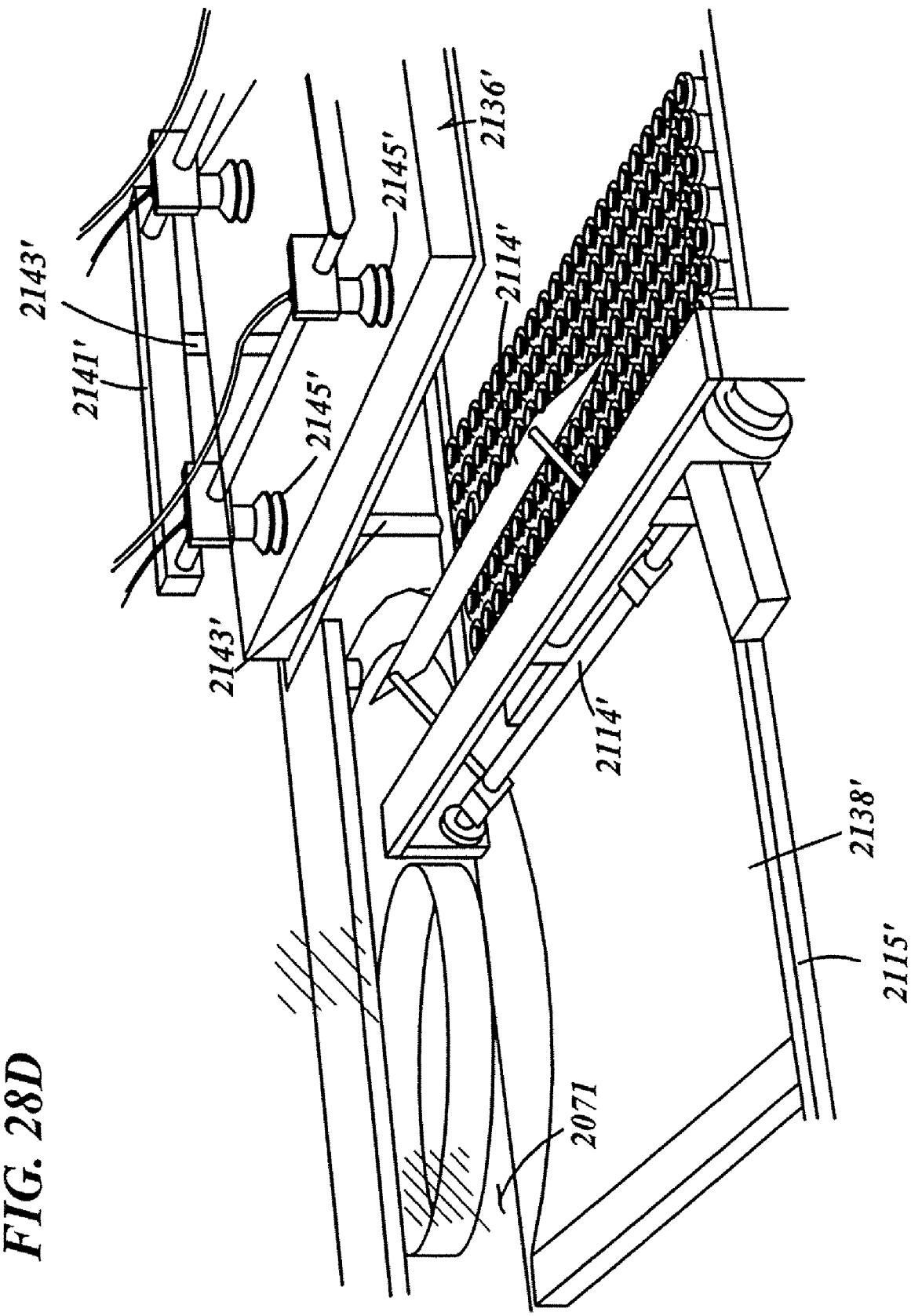
Figure 28E:
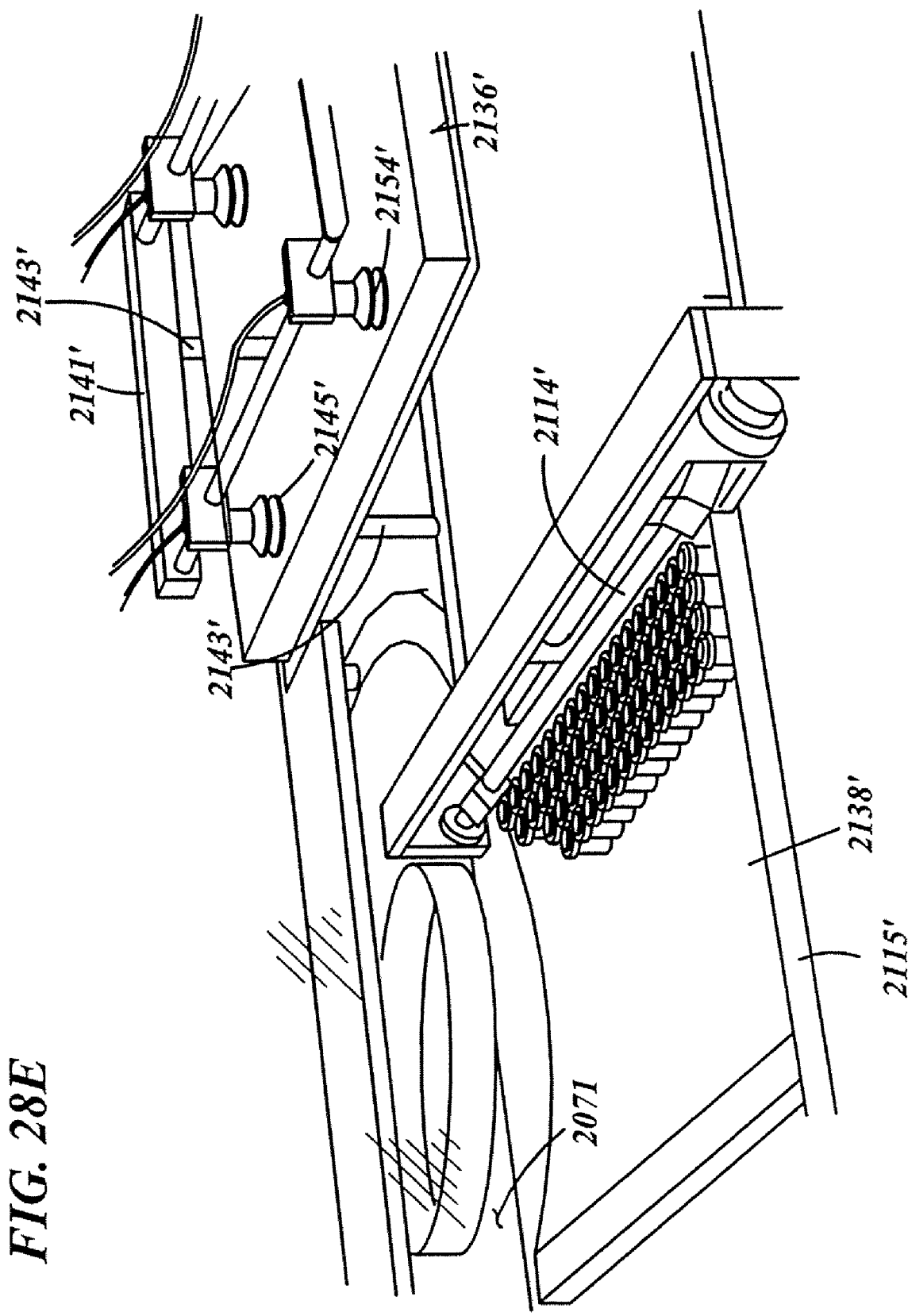
Figure 28F:
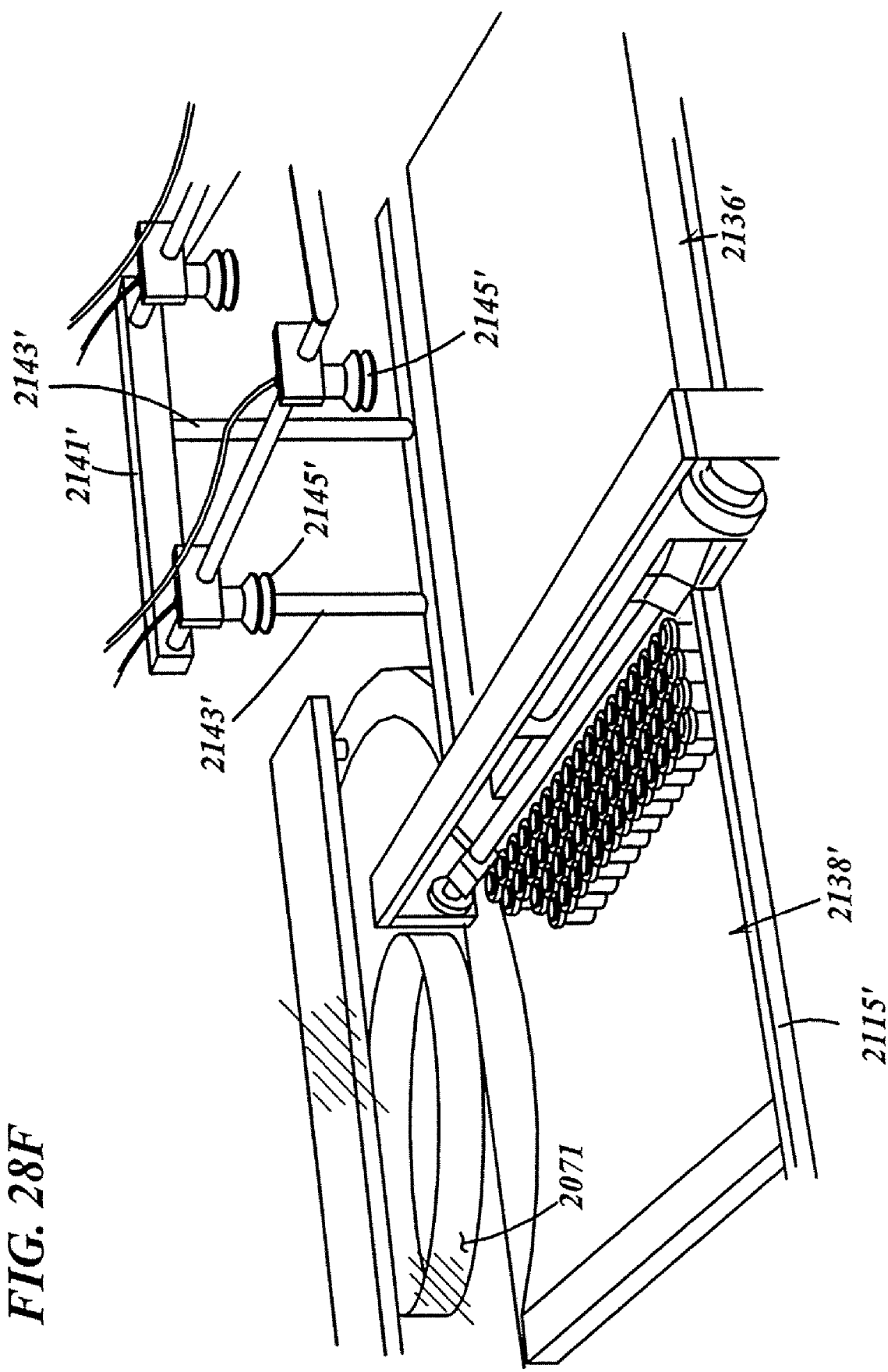
Figure 28G:
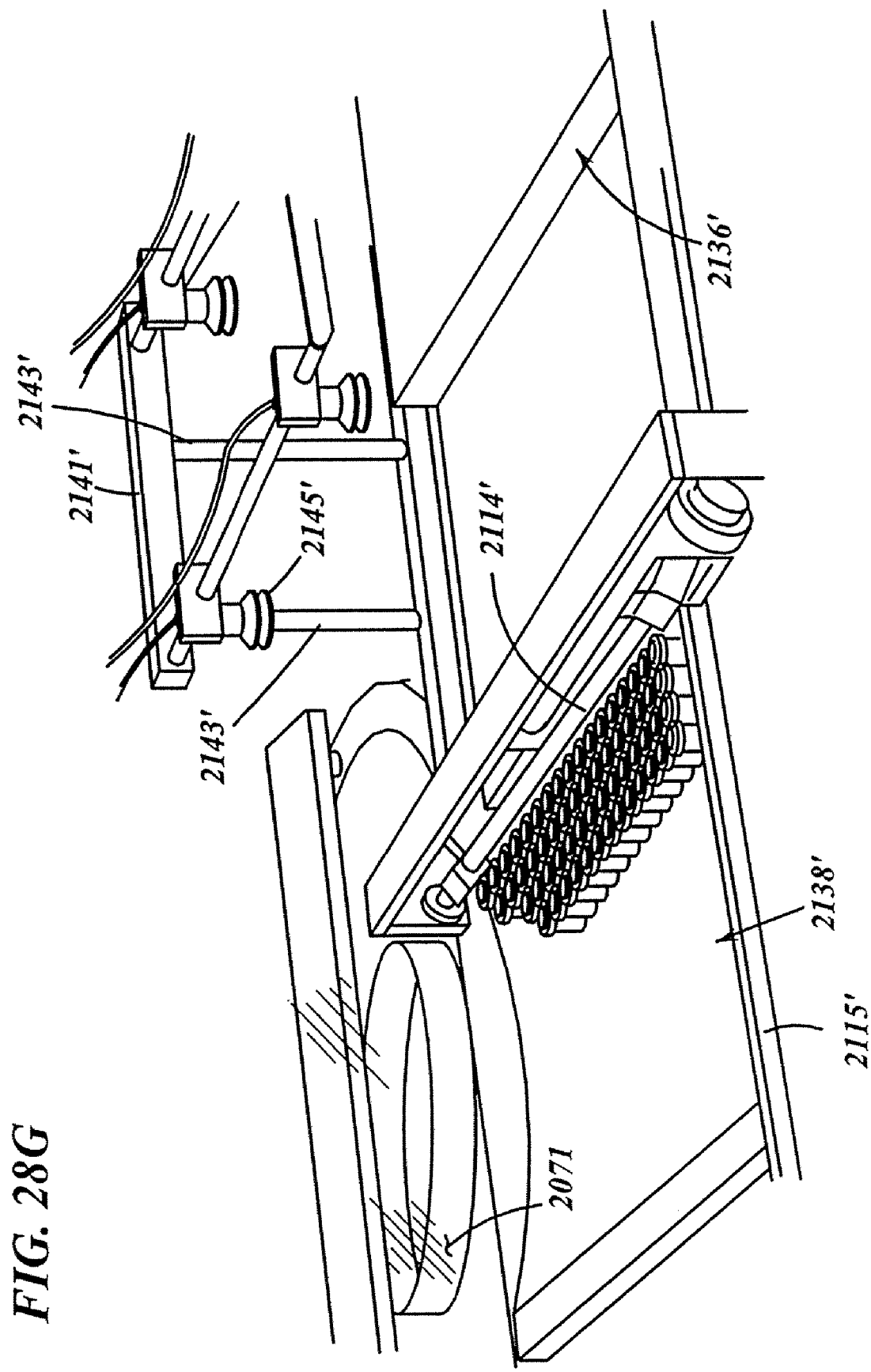
Figure 28H:
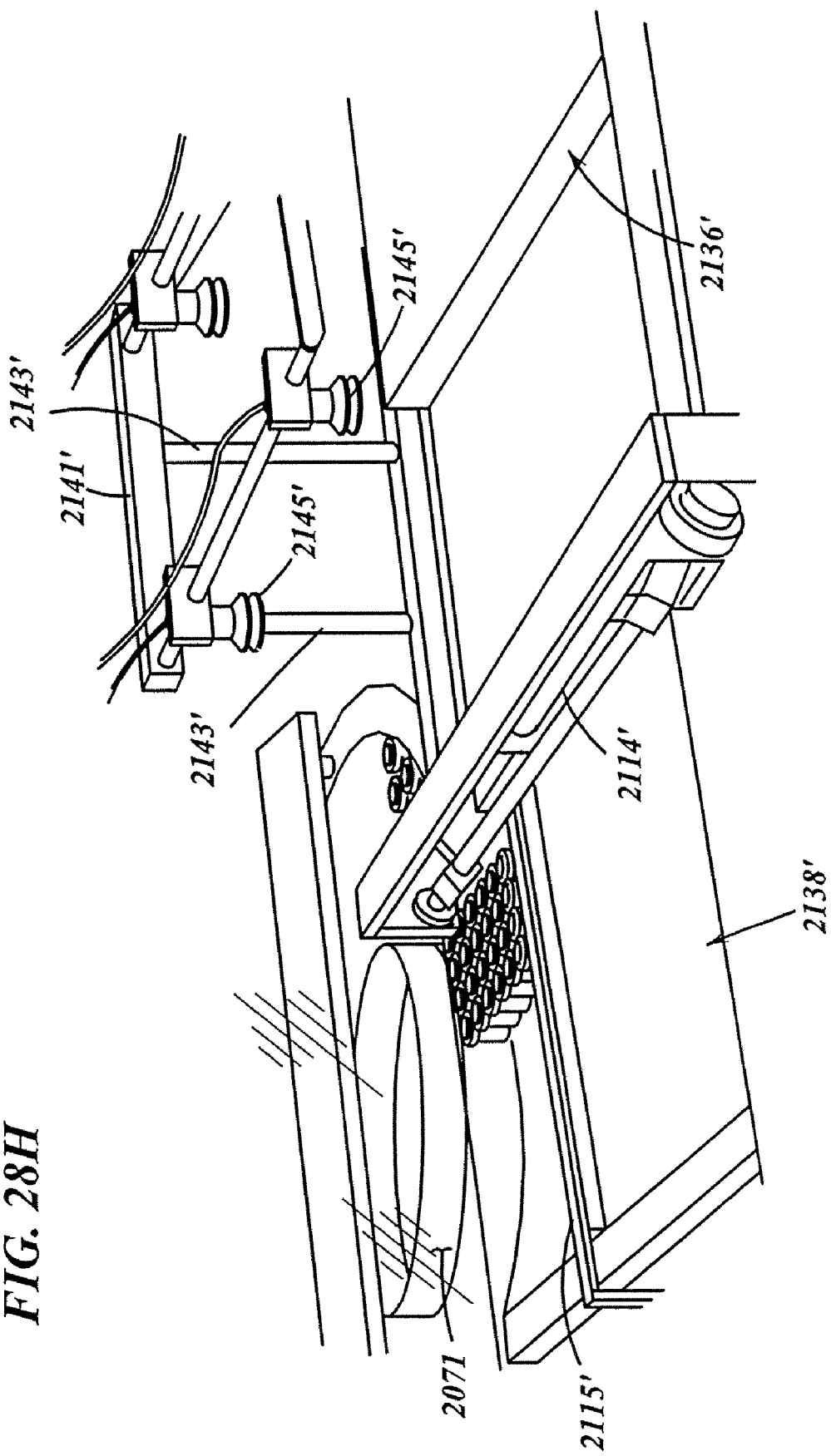
Figure 28I:
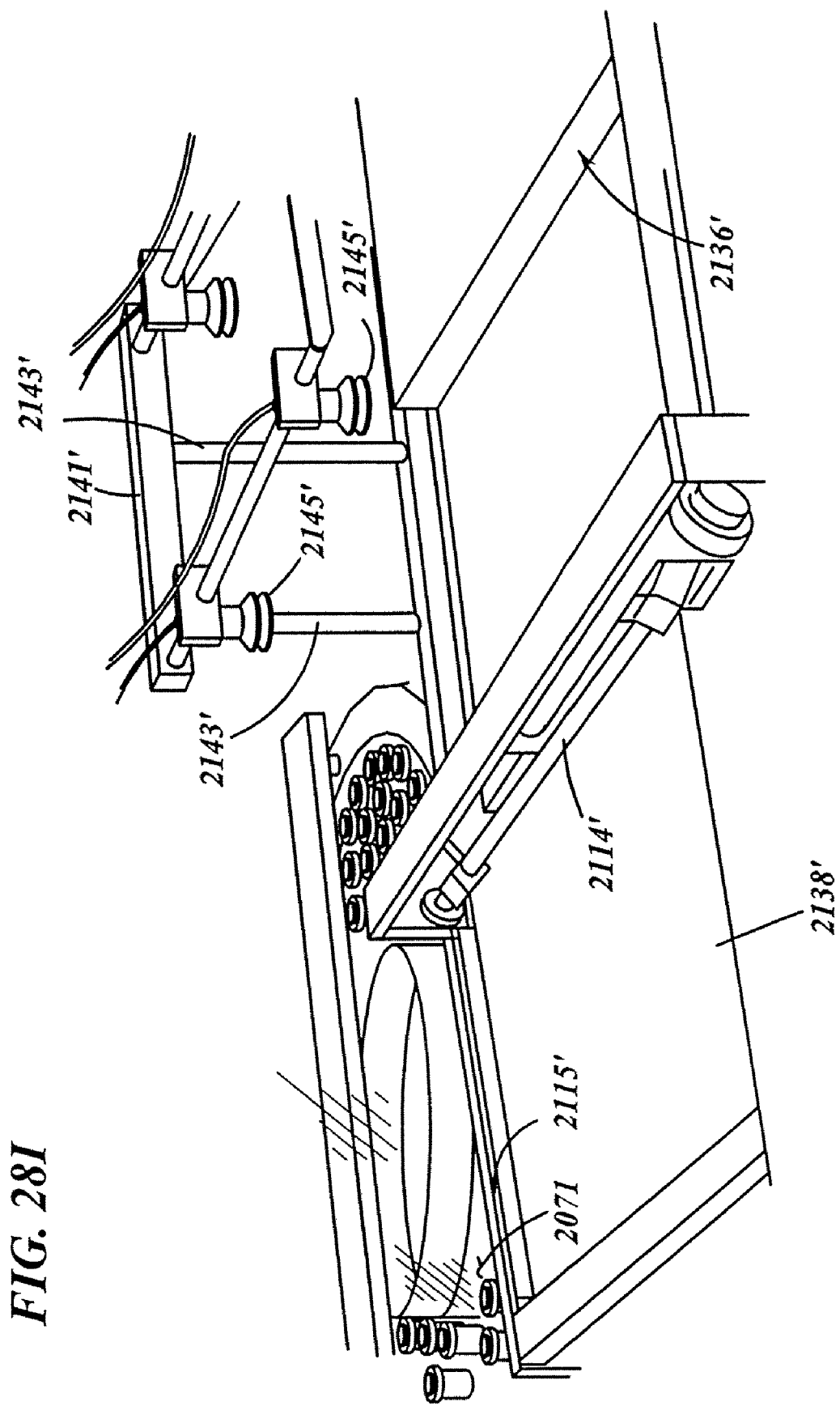

The first sweeper arm 2114' is pivotally mounted and movable between a down position, as shown typically in FIG. 28B, and an up position, as shown typically in FIG. 28D. The first sweeper arm is driven by a suitable drive source (not shown), such as a servo-actuator, between the down and up positions. Further, the first sweeper arm 2114' is driven horizontally by a suitable drive source (not shown), such as a servo-drive, between a rearward position, shown typically in FIG. 28D, and a forward position (not shown) spaced adjacent to the infeed port 2108 for sweeping the vials off of the tray and into the second staging area 2138'. As shown in FIG. 28D, after the lifter 2141' lifts the tray cover away from the vials, the first sweeper arm 2114' is pivoted upwardly and driven from the rearward position (FIG. 28D), to the forward position adjacent to the infeed portion 2108. Then, in the forward position, the first sweeper arm 2114' is pivoted into the down position, and is then driven from the forward position to the rearward position to, in turn, sweep the vials off of the tray and into the second staging area, as shown in FIGS. 28E-28G. Then, when all of the vials are located in the second staging area, the second sweeper arm 2115' is driven laterally from a rearward position, as shown typically in FIG. 28G, to a forward position, as shown in FIG. 28I, to move the vials from the second staging area, beneath the barrier 2017 extending between the infeed unit and the filling unit, and onto the turntable 2150 of the infeed unit.

Referring again to FIG. 24, the fill unit 2014 includes a transport system including a turntable 2150 and four star wheels 2152, 2154, 2156, and 2158. As will be further described below, the turntable 2150 is adapted to rotate in a counter-clockwise direction. The first and third star wheels 2152, 2156 are adapted to rotate in the clockwise direction. The second and fourth star wheels 2154, 2158 are adapted to rotate in the counter-clockwise direction. Examples of the containers filled by this embodiment of the filling machine 2010 are indicated at 2015A, 2015B, 2015C, 2015D, 2015E, and 2015F.

Figure 30A:
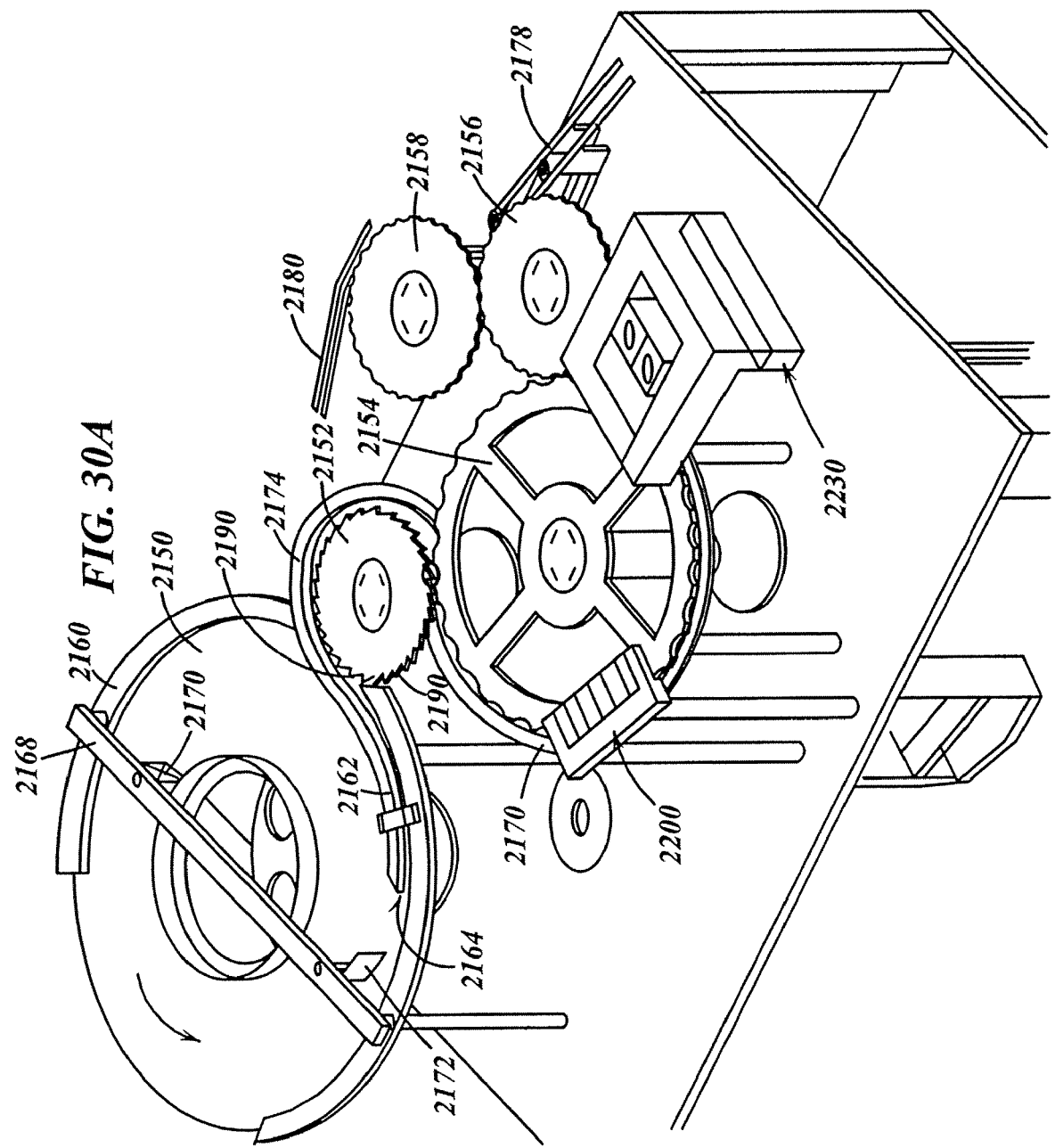

As shown in FIG. 30A, a first guide 2160 is provided at the periphery of the turntable 2150. This guide 2160 keeps the containers from falling off of the turntable 2150. A second guide 2162 is spaced apart from a section of the first guide to define a channel 2164 therebetween. A third guide assembly (see FIG. 30A) includes a support member 2168 which is disposed over the turntable 2150 and supports guides 2170, 2172 (see FIG. 30A), which collectively steer the containers toward the channel 2164 defined by the first and second guides 2160, 2162.

A fourth guide 2174 is provided at the periphery of the first star wheel 2152. A fifth guide 2176 is provided at the periphery of the second star wheel 2154. A sixth guide 2178 is fed from (i.e., in communication with) the periphery of the third star wheel 2156 and transports containers that have been successfully filled and sealed. A seventh guide 2180 is fed from the periphery of the fourth star wheel 2158 and transports containers that have not been successfully filled or not successfully sealed.

Figure 38:
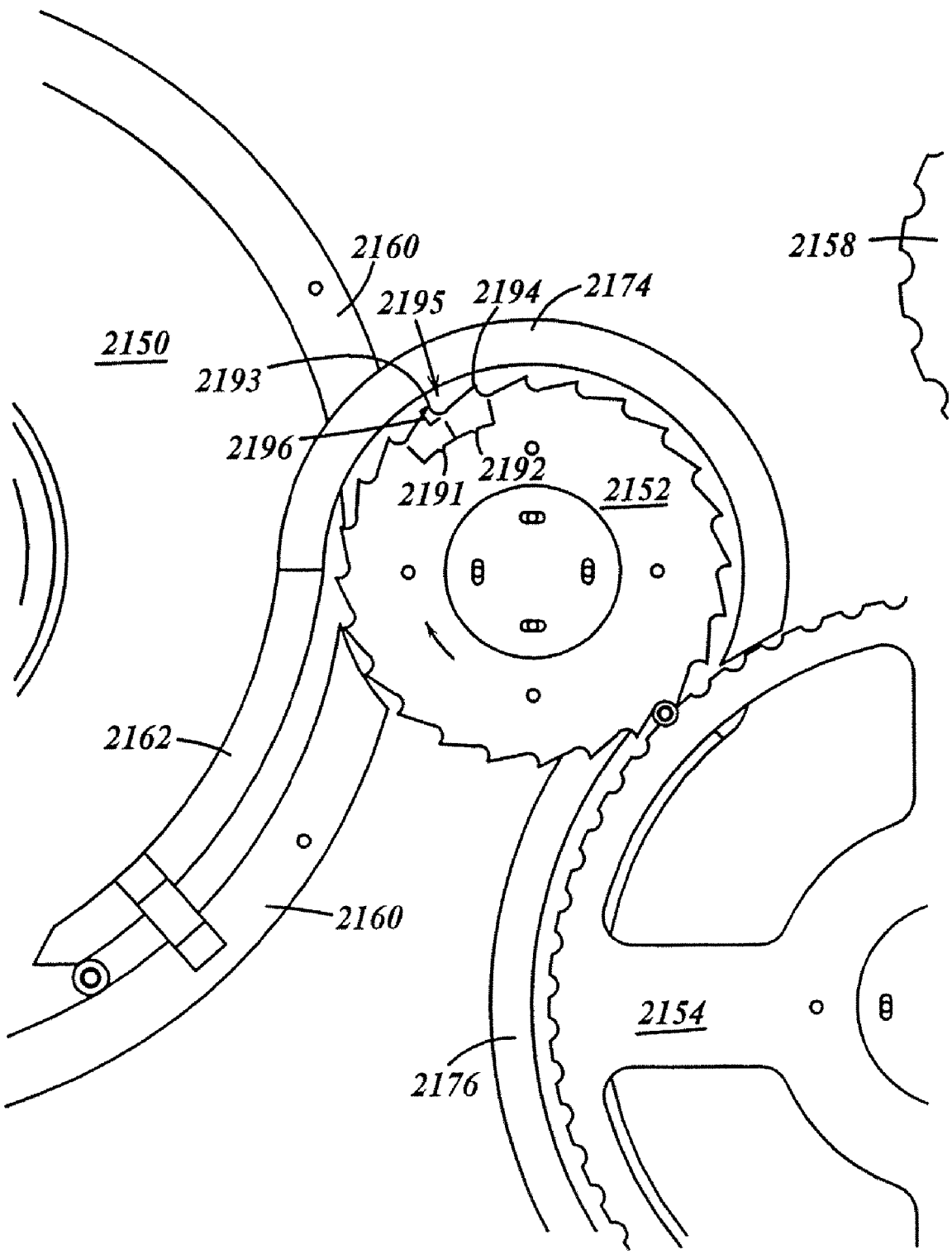
FIG. 38 is an elevational view of a portion of the fill assembly of the filling machine of FIGS. 18-20 including the first star wheel, the turntable, and the second star wheel.

Each of the star wheels 2152, 2154, 2156, 2158 has a plurality of recesses along its peripheral surface that are adapted to receive containers. The first star wheel 2152 preferably has a saw-tooth like periphery 2190 that reduces the likelihood of jamming against containers as they are received from the channel 2164. FIG. 38 is an elevational view of one embodiment of the first star wheel 2152. In such embodiment, the periphery of the first star wheel 2152 defines a plurality of teeth, e.g., 2191, 2192. Each tooth has a pointed end, e.g., 2193, 2194. Each two successive teeth surround, on two opposite sides, a respective one of the recesses adapted to receive a container. For example, in this embodiment teeth 2191, 2192 surround recess 2195. In this embodiment, the teeth and/or recesses are shaped and/or dimensioned such that the portion of the tooth that is substantially upstream and adjacent to the point defines a seat 2196 in which a respective container will rest. In this embodiment, the seat 2196 defines a surface that pushes against the container. Other designs may of course also be employed.

Referring again to FIG. 26A, the recesses of the third and fourth star wheels 2156, 2158 are provided with vacuum ports which are selectively connected to a vacuum source to thereby allow the third and fourth star wheels to carry containers as appropriate.

As shown best in FIGS. 30A and 31A-31H, a needle fill manifold 2200 is disposed at a first position along the periphery of the second star wheel 2154. The needle fill manifold 2200 holds a plurality of needles, e.g., four needles 2202, 2204, 2206, 2208, which are used to deliver medicament into the containers. The needle manifold 2200 is drivingly mounted such that each needle is movable into and out of engagement with the resealable stoppers to pierce the stoppers and fill the vials or other containers with a medicament or other substance to be contained therein, and to then withdraw the needle upon filling the vial. Providing multiple needles makes it possible to fill multiple containers concurrently. As shown in FIG. 31A-31H, each of the needles is in flow communication with a respective flexible tube 2212, 2214, 2216, 2218 that connects the respective needle 2202, 2204, 2206, 2208 to a respective medicament source (not shown) through a respective one of the pumps 2070-2076 (FIG. 30F). Note that the medicament source may be located inside the filling machine 2010 or outside of the filling machine. Note that bellows 2220 (FIG. 26A) may be provided on the shafts that drive the needles or needle manifold 2200 to seal the movable parts of the shafts. In some embodiments, the needle stroke length may be about 1 inch.

A laser sealing and infrared (IR) sense manifold 2230 (see FIGS. 30A, 36, 37A-37D) is disposed at a second position along the periphery of the second star wheel 2154, downstream of the needle fill manifold 2200. The laser sealing and IR sense manifold 2230 is not shown in certain other figures in order to preserve clarity. As shown typically in FIG. 36, this manifold 2230 holds a plurality of laser optics assemblies (e.g., four laser optic assemblies 2232, 2234, 2236, 2238) along with a plurality of IR sensors (e.g., four IR sensors 2242, 2244, 2246, 2248). The laser optic assemblies are adapted to provide a laser beam to reseal the resealable caps or stoppers on the containers after needle filling. Each of the plurality of laser optic assemblies is mounted at a respective location near the periphery of the second star wheel 2154 for transmitting a respective laser beam onto a respective resealable stopper to heat seal the needle aperture in the resealable stopper. Each of the laser optic assemblies 2232, 2234, 2236, 2238 is connected to a respective fiber optic cable 2233 that connects the respective optic assembly 2232, 2234, 2236, 2238 to a respective laser source 2080, 2082, 2084, 2086 (FIG. 20). Providing multiple fiber optic assemblies makes it possible to reseal multiple containers concurrently.

In this embodiment, each of the plurality of IR sensor assemblies 2242-2248 is mounted at a respective location near the periphery of the second star wheel 2154. As shown, the laser sources 2080-2086 are mounted outside of the enclosure 2044 to enable repair and/or replacement of the laser sources without having to open the enclosure and/or otherwise risk contamination of the sterile enclosure. The IR sensors 2242-2248 detect the temperature of the needle penetration region of the resealable stopper achieved during laser resealing, and therefore can be used to determine whether the stopper was sufficiently reheated to achieve resealing. Each of the IR sensors 2242, 2244, 2246, 2248 is connected to a respective IR sensor module 2090, 2092, 2094, 2096 (FIG. 20). Providing multiple IR sensors enables the sterile filling machine 2010 to sense the temperature of multiple containers concurrently, for example, as they are being resealed. As described above, each laser source transmits a predetermined wavelength of laser radiation at about 980 nm, and the predetermined power of each laser is preferably less than about 30 Watts, and preferably less than or equal to about 10 Watts, or within the range of about 8 to about 10 Watts. In the illustrated embodiment, each laser source is a semi-conductor diode laser that outputs at about 15 Watts, and is fiber-optically coupled through a fiber-optic cable to respective collimating lens mounted over the vials within the interior of the filling unit. One advantage of mounting the laser sources outside of the enclosure is that they can be easily repaired or replaced without having to access the interior of the enclosure.

Capacitor sensors (not shown) also may be provided along the periphery of the second star wheel 2154, downstream of the needle fill manifold 2200. Such sensor can be used to sense whether a container received any medicament.

Figure 39A:
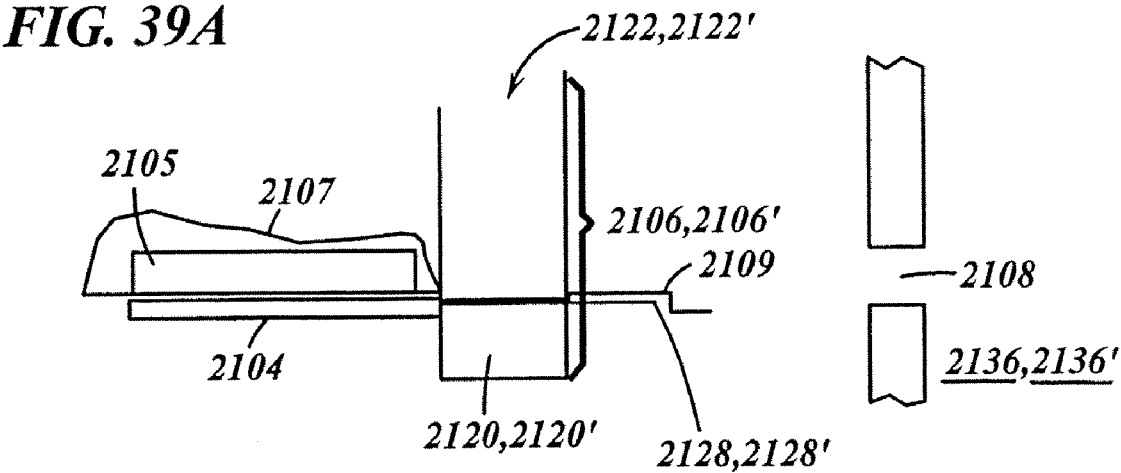
FIGS. 39A-39C show side elevational views of sequential steps employed to insert a tray of containers into the infeed unit of the sterile filling machine of FIGS. 18-20.
Figure 39B:
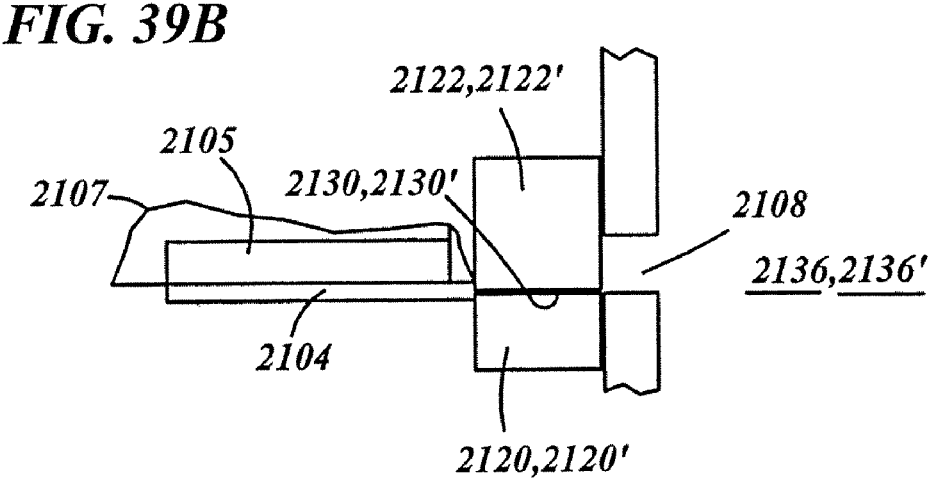
Figure 39C:
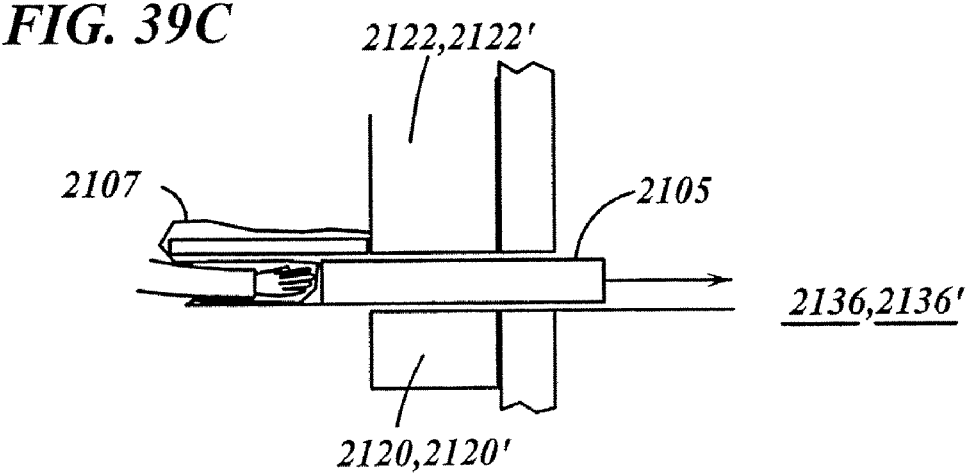

FIGS. 39A-39C show side elevational views of sequential steps employed in one embodiment to insert a tray of containers into the infeed unit 2012. Referring now to FIGS. 39A-39C, in use, a bagged tray of containers 2105 is placed on the shelf 2104. With the clamp 2106, 2106' open, one end of the bag 2107 is inserted through and beyond the open clamp thereby defining a portion 2109 that extends beyond and overhangs the clamp. The end 2109 of the bag is then arranged so as to lay flat on the surface 2128, 2128' of the first clamp portion 2120, 2120' and the clamp 2106, 2106' is closed. With the clamp 2106, 2106' closed, the overhanging portion 2109 of the bag 2107 is cut off and discarded, and the vacuum source is applied to the vacuum ports of the two clamp portions 2120, 2122, 2120', 2122'. The clamp 2106, 2106' is then opened, and because of the vacuum applied to the vacuum ports, the cut end of the bag 2107 opens therewith. This is because the vacuum applied to the vacuum ports 2132, 2132' causes the bottom side of the cut end of the bag to be releasably secured to the surface 2128, 2128' of the first clamp portion 2120, 2120' and causes the top side of the cut end of the bag to be releasably secured to the surface 2130, 2130' of the second clamp portion 2122, 2122'.

After the clamp 2106, 2106' and the cut end 2109 of the bag are open, force is applied to the tray 2105, through the other side of the bag, so as to push the tray through the open clamp, through the infeed port 2108, and onto the first staging area 2136, 2136'. The blower 2139 (FIG. 22) fills the open bag with sterile air and thus facilitates the opening of the bag and the release of the sterile trays and vials therefrom and into the infeed unit. The vacuum is removed from the vacuum ports 2132, thereby releasing the bag 2107, which may then be discarded. As shown in FIG. 39C, the second portion 2122 of the clamp and the wall defining the top of the infeed port 2108 hang low enough to block entry of the overlying tray or lid that had been retaining the containers positioned on the tray. Alternatively, the overlying tray or lid is moved into the infeed unit, and the lifter is actuated to lift the tray cover off the tray to expose the vials thereon.

After the tray 2105 is in the first staging area 2136, 2136', and with reference to FIGS. 28B-28G, the first sweeper arm 2114, 2114' is actuated so as to slide the containers off the tray and into the second staging area 2138, 2138'. The first sweeper arm 2114, 2114' may be actuated manually, using the handle 2110, or automatically, as described above. With reference to FIGS. 28H and 28I, the empty tray 2105 is thereafter removed from the infeed unit 2012, 2012'. After the containers are in the second staging area 2138, 2138', the second sweeper arm 2115, 2115' is actuated so as to slide the containers into the fill unit 2014, and onto the turntable 2150.

As stated above, in this embodiment, each container is a vial defining a substantially "diabolo" shape formed by a base, a cap and a body extending between the base and cap, wherein the base and cap define a diameter or width that is greater than that of the body. The diabolo shape may facilitate securing and otherwise transporting the vials through the filling machine 2010. Further, the "diabolo" shape of the vials facilitates transporting the vials or the star wheels or other transporting mechanism without the need for a base surface to support the base of the vial. In addition, the diabolo shape facilitates supporting the vial in the needle filling station and to hold the vials in place when penetrated by the needles, as shown, for example, in FIG. 31D.

After the containers are on the turntable 2150, they are guided by the guides 2170, 2172 (FIG. 30A) toward the turntable periphery and into a single file relationship within the channel 2164. The recesses of the first star wheel 2152 receive containers from the channel 2164 and advance the containers in a clockwise direction along the guide 2174, typically at predetermined rate.

The containers are transferred to the recesses of the second star wheel 2154 as they reach the first or input end of the guide 2176. The second star wheel 2154 transports the containers along the guide 2176. The second star wheel 2154 is indexed four positions and then paused for a momentary dwell. During the dwell, the needle manifold 2200 is driven downward so as to drive the four needles 2202-2208 through the resealable stoppers on the four containers beneath the needle manifold 2200. Medicament is thereafter delivered to the containers and the manifold is then driven up to thereby retract the four needles 2202-2208 from the four stoppers. In one embodiment, the needles are initially withdrawn at a relatively slow speed to allow the vials to fill "bottom-up"; then, when the vials are filled, the needles are withdrawn at a relatively faster speed to quickly remove the needles and decrease overall cycle time. In another embodiment, the depth of stroke of the needle is set to reduce or prevent the formation of particles. In one such embodiment, at the bottom of the needle stroke, the needle flow apertures are spaced below the bottom wall of the stopper and adjacent or contiguous thereto (i.e., the upstream end of each hole is adjacent to the inside surface of the bottom wall of the stopper). In one such embodiment, the needle tip penetrates beyond the inside surface of the bottom wall of the stopper to a depth within the range of about 1 to about 5 cm, preferably within the range of about 1 to about 3 cm, and most preferably about 1.5 centimeters. At the bottom of the needle stroke, the medicament or other substance is delivered therethrough and into the vials. Then, when the predetermined amount of medicament or other substance is delivered, the needles are withdrawn. Preferably, the needle and/or stopper is treated to reduce friction at least at the needle/stopper interface to, in turn, further prevent the formation of particles. In the latter embodiment, the needles are not withdrawn while filling. Rather, the needles penetrate the stoppers a minimum amount as indicated above to allow filling while holding the needles in place, for example, at the bottom of the stroke, and then the needles are withdrawn from the stoppers after filling. One advantage of this embodiment is that it reduces the relative movement of the needle and stopper surfaces, and thus facilitates in preventing the formation of particles during needle penetration and withdrawal.

Also during the dwell, the four laser optic assemblies 2232-2238 deliver laser energy to the resealable stoppers on the four containers beneath the laser and IR manifold to reseal said stoppers. As the resealable stoppers are heated by the laser energy, the four IR sensors 2242-2248 detect the temperature of each stopper, so as to be able to determine whether each stopper was heated sufficient to cause resealing. After the dwell, the process is repeated, i.e., four star wheels 2152, 2154, 2156, 2158 index another four positions and then dwell again so that the next four containers are filled and four more containers are resealed.

After resealing, the containers are transferred to the third star wheel 2156, which employs the vacuum ports in its recesses to retain each container as it is transported. If a container was successfully filled and sealed, then the third star wheel 2156 transports that container until reaching the guide 2178, at which point the vacuum to the associated vacuum port is selectively removed and the container is transferred to the guide 2178. The guide 2178 transports the container to a bin (not shown) of successfully filled and sealed containers.

If a container was not successfully filled and sealed, then the third star wheel 2156 transports that container until the container reaches the fourth star wheel 2158, at which point the vacuum to the associated vacuum port is selectively removed and vacuum is applied to the respective vacuum port on the fourth star wheel 2158, thereby transferring the container to the fourth star wheel 2158. The fourth star wheel 2158 transports that container until reaching the guide 2180, at which point the vacuum to the associated vacuum port is selectively removed and the container is transferred to the guide 2180, which transports the container to a bin of containers (not shown) that were not successfully filled and resealed.

The turntable 2150 and four wheels 2152, 2154, 2156, 2158 are each driven by a respective drive shaft. Each of the drive shafts is housed within a shaft housing, e.g., the drive shaft for the second star wheel is housed within a shaft housing 2270. Each shaft housing includes a stand, e.g., stand 2272, secured to the plate 2040 of the fill unit 2014, an elongated member, e.g., member 2274, secured to the stand, and a wheel mounting member, e.g., 2276, between the elongated member and the respective star wheel. Note that the housings are preferably provided with O-ring shaped seals in order to reduce the possibility that dirt, grease or other contaminants will enter the filling station 2014 from within the housing. In this embodiment, the O-ring seals comprise an elastic material, for example, a rubber compound such as Viton.

Figure 30B:
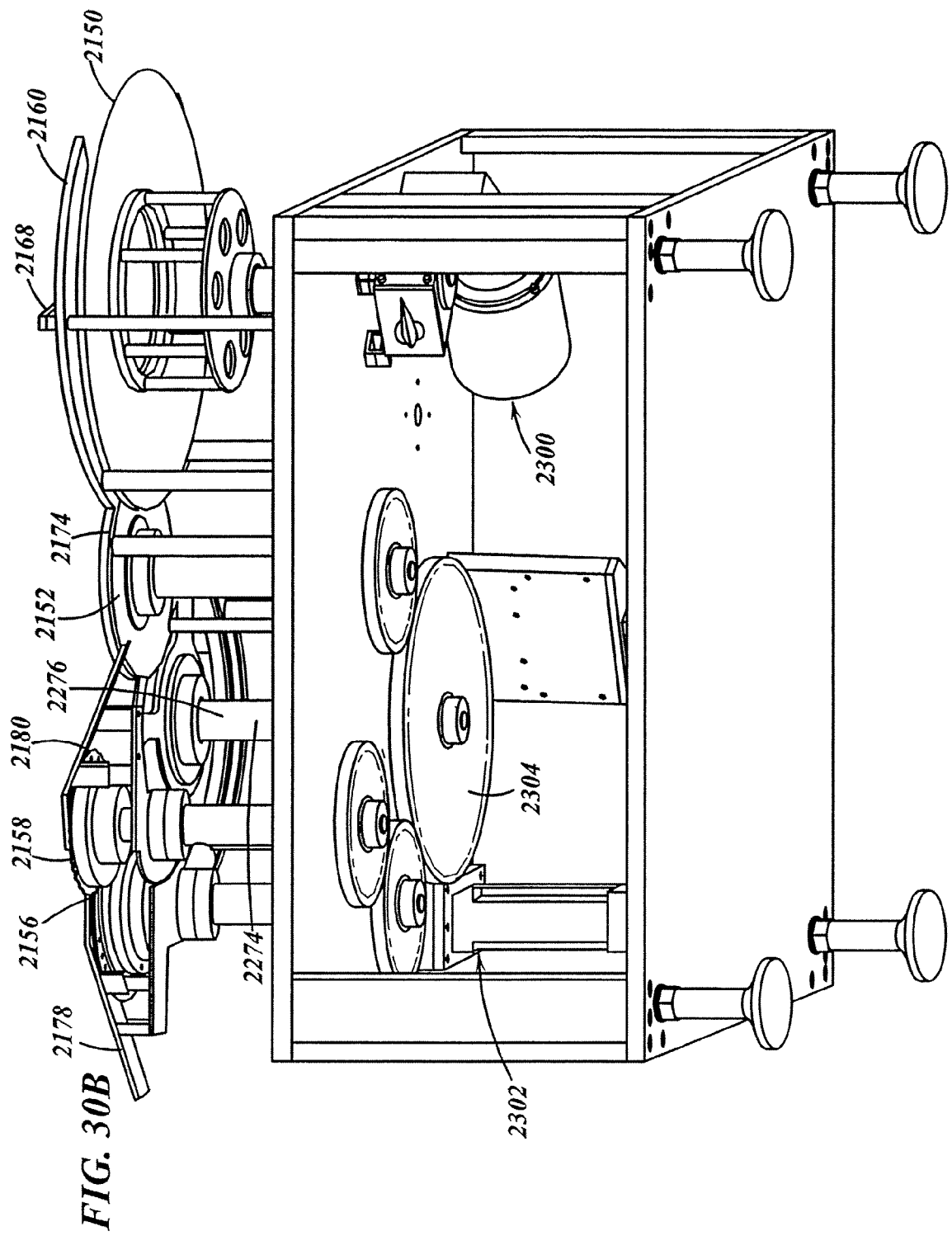
Figure 30D:
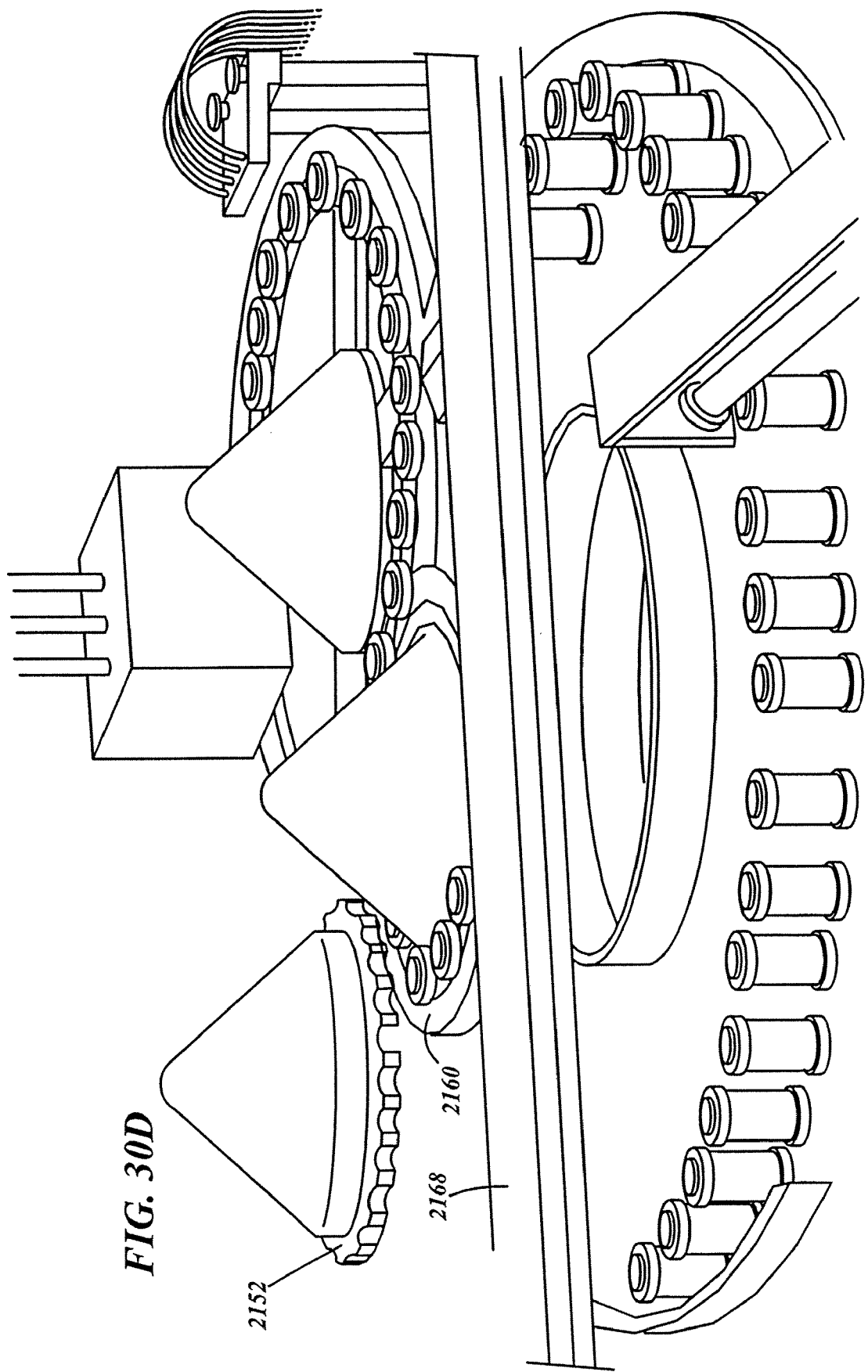
Figure 30E:
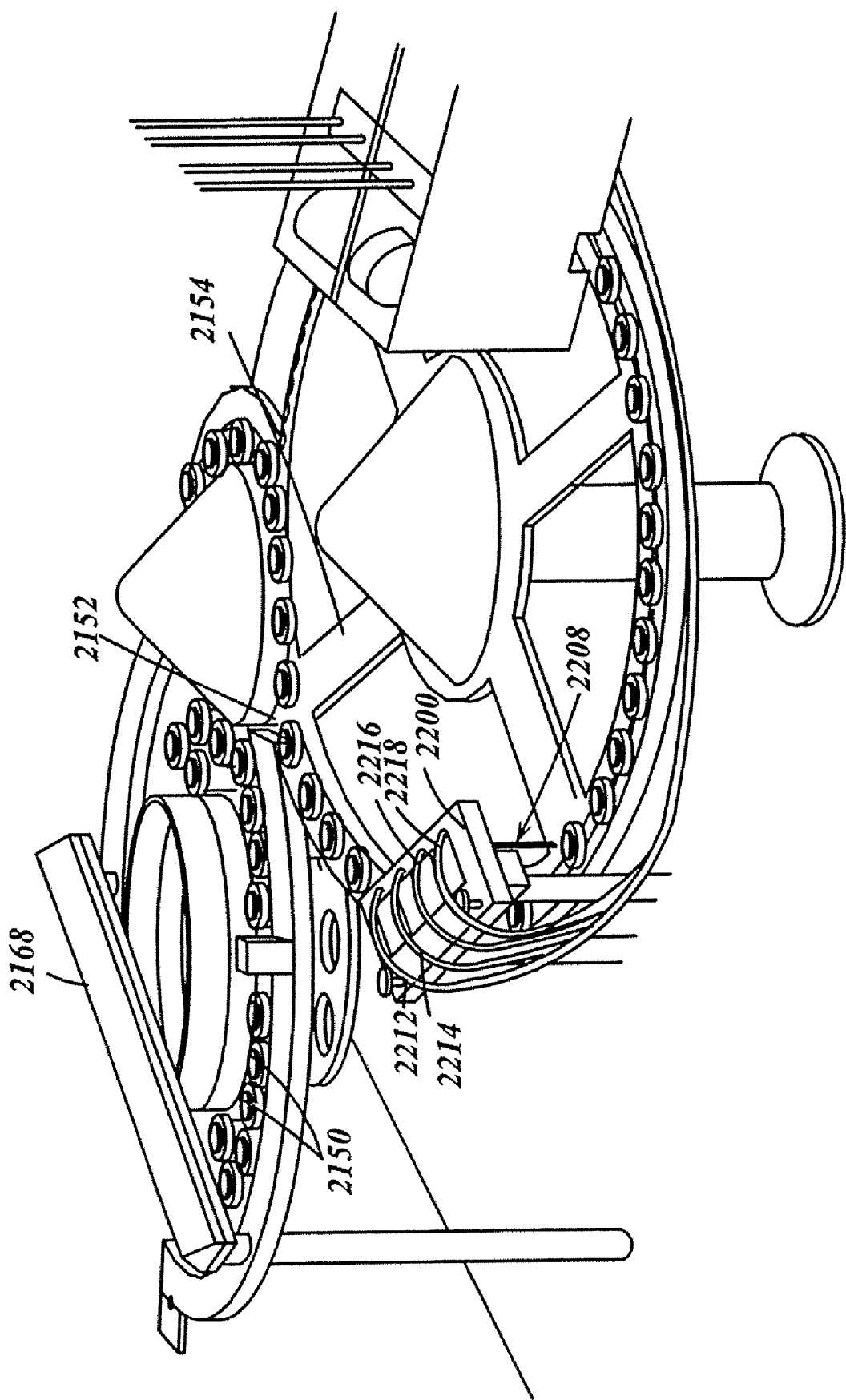
Figure 30F:
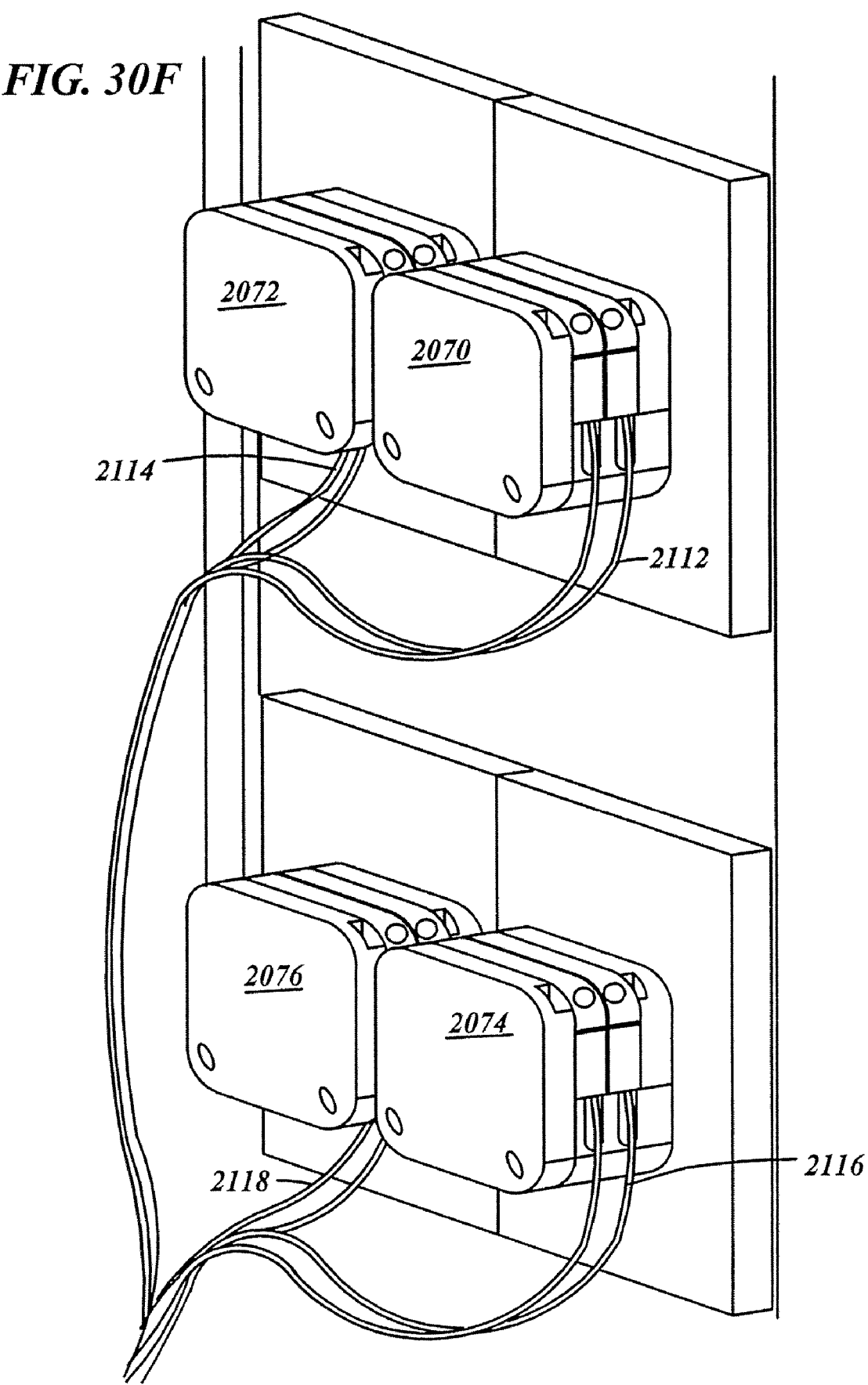

The drive shaft of the turntable 2150 is operatively coupled to and driven by a first drive assembly 2300 (FIG. 30B). The drive shafts of the star wheels are operatively coupled to and driven by a second drive assembly 2302 (FIG. 30B). In particular, the drive assembly 2302 is coupled to a gear 2304 coupled to the drive shaft of the second star wheel 2154. The drive shafts for the first and third star wheels 2152 and 2156, respectively, are driven in rotary fashion from the gear 2304 for the second star wheel. The drive shaft for the fourth star wheel 2156 is driven from the gear for the third star wheel 2154. One advantage of this arrangement is that it results in less stack up tolerance than that achieved by a linear drive arrangement.

In this embodiment, the vertically-extending space between the components of the fill assembly (e.g., the star wheels) and the plate 2040 helps allow laminar, filtered airflow around these components.

In some embodiments, the needles may have grooves on the outside to allow venting of gas out of the vial upon filling. In some other embodiments, the needles may instead be double lumen type needles, to allow venting.

The needle may have any shape now known or later discovered. In some embodiments, the needle has a tip with a pencil point shape. In some other embodiments, the needle has a tip with an arrow head shape or a trocar profile shape. In some embodiments, the shape of the needle and/or the needle tip may be adapted to help minimize or prevent the formation of particles (or debris) upon piercing the stopper, minimize wear on the needle, and/or help ensure that the stopper remains resealable. The width of the needle may impact the fill rate. In some embodiments, the shape of the needle represents a compromise between two or more of the above factors. In some embodiments, the amount of force employed to plunge the needles through the stopper is about two pounds per needle.

Figure 34:
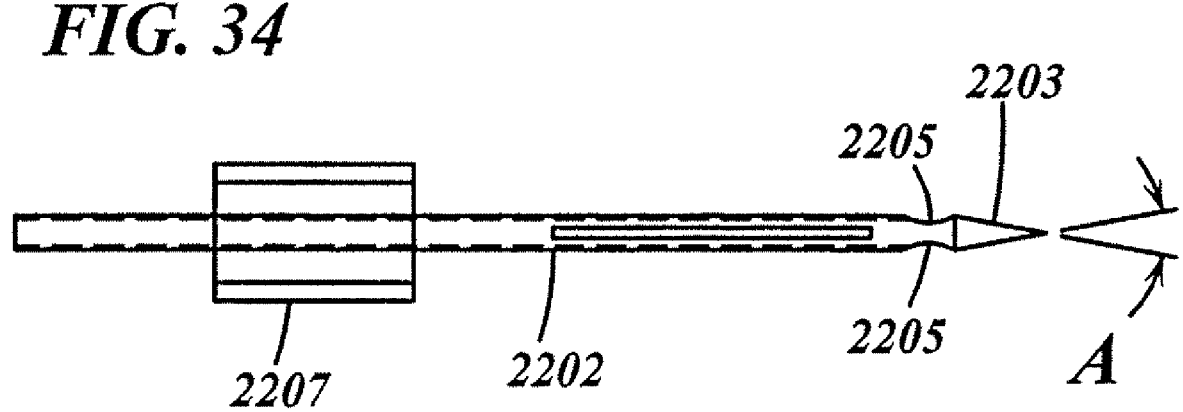
FIG. 34 includes a plurality of cross-sectional views of a pencil point type needle that may be mounted in the needle manifold of FIGS. 31A-31H.
Figure 35:
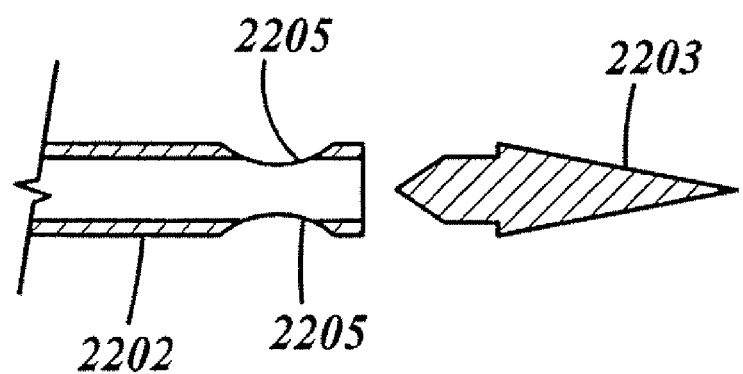
FIG. 35 includes a plurality of cross-sectional views of another needle that may be mounted in the needle manifold of FIGS. 31A-31H.
Figure 36:
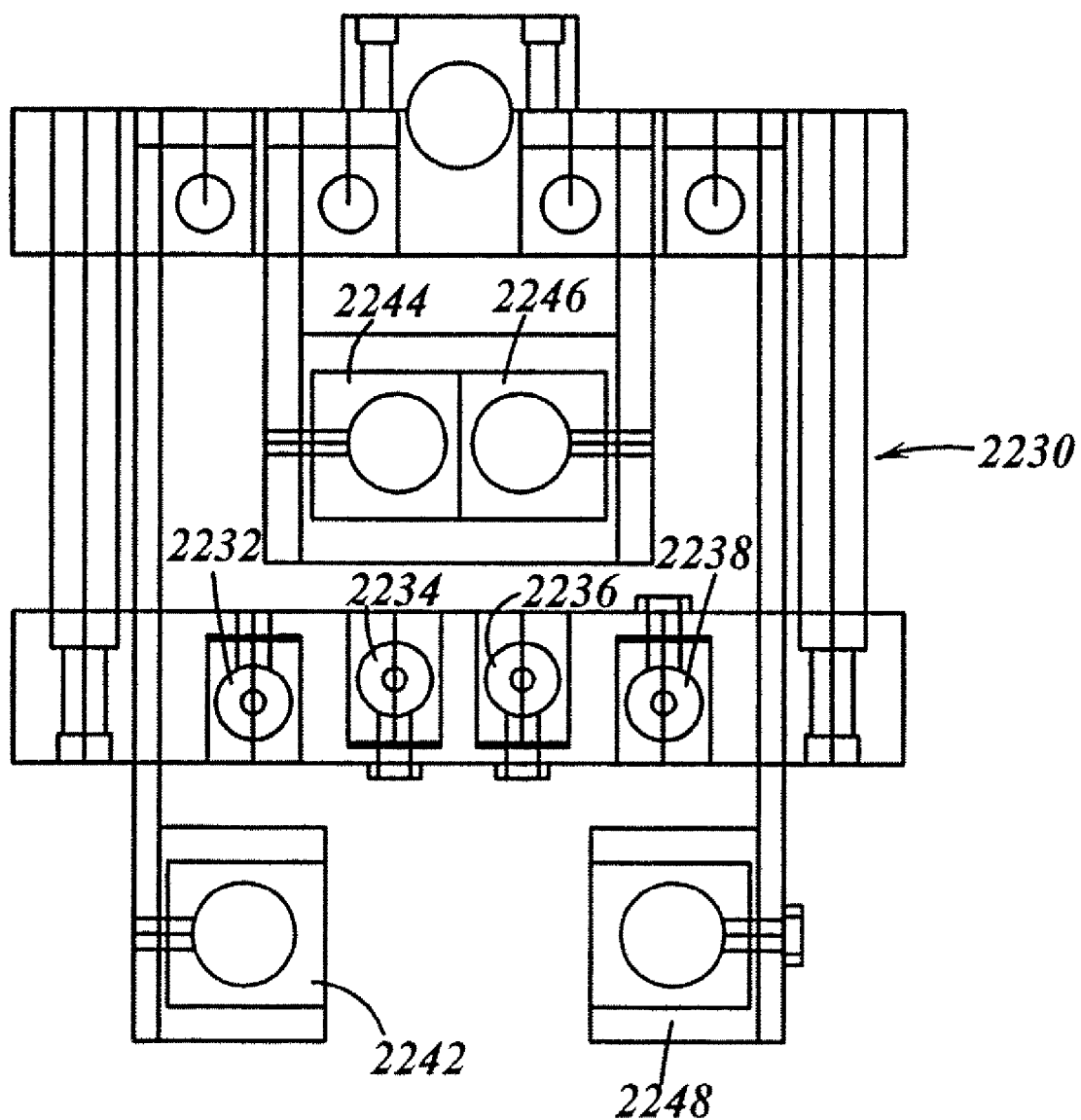
FIG. 36 is an enlarged elevational view of the laser sealing and IR sense manifold of FIGS. 30A-30F.
Figure 37C:
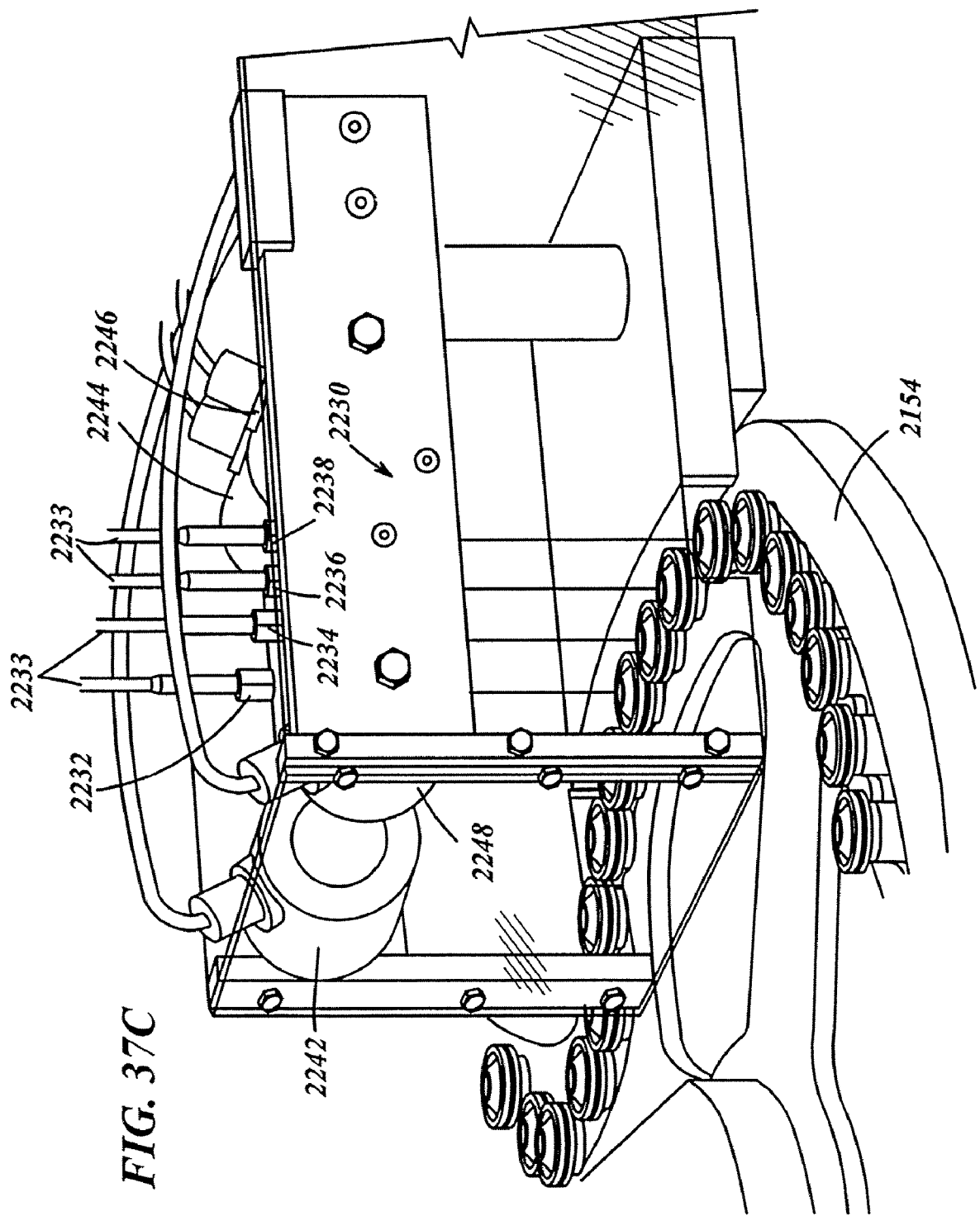
Figure 37D:
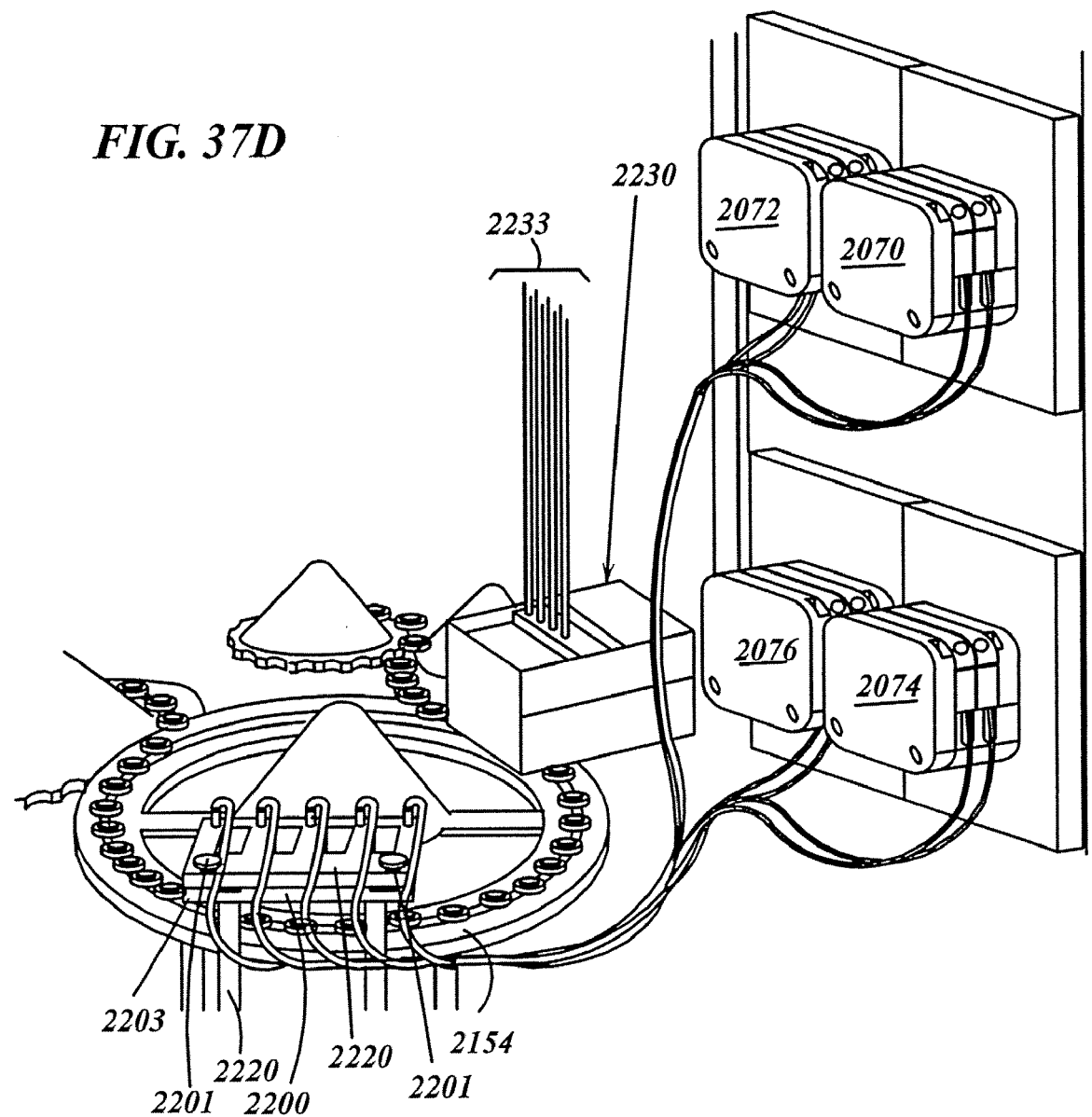

As shown in FIGS. 34 and 35, a typical needle 2202 defines a conically-pointed, non-coring tip (i.e., a "pencil point" tip) 2203, wherein the included angle "A" of the tip in cross-section is within the range of about 15° to about 25°, preferably about 18° to about 22°, and most preferably about 20°. The smooth, sharply-pointed, gradually increasing angle of the needle tip allows for a relative smooth, and gradual expansion of the needle hole upon penetrating the stopper. The needle tip further defines two axially oblong flow apertures 2205 on opposite sides of the needle relative to each other. In the currently preferred embodiment, the needle is about 15 gage (i.e., 0.072 inch diameter). However, as may be recognized by those of ordinary skill in the pertinent art based on the teachings herein, this dimension is only exemplary and may be changed as desired or otherwise required by an application.

Figure 31A:
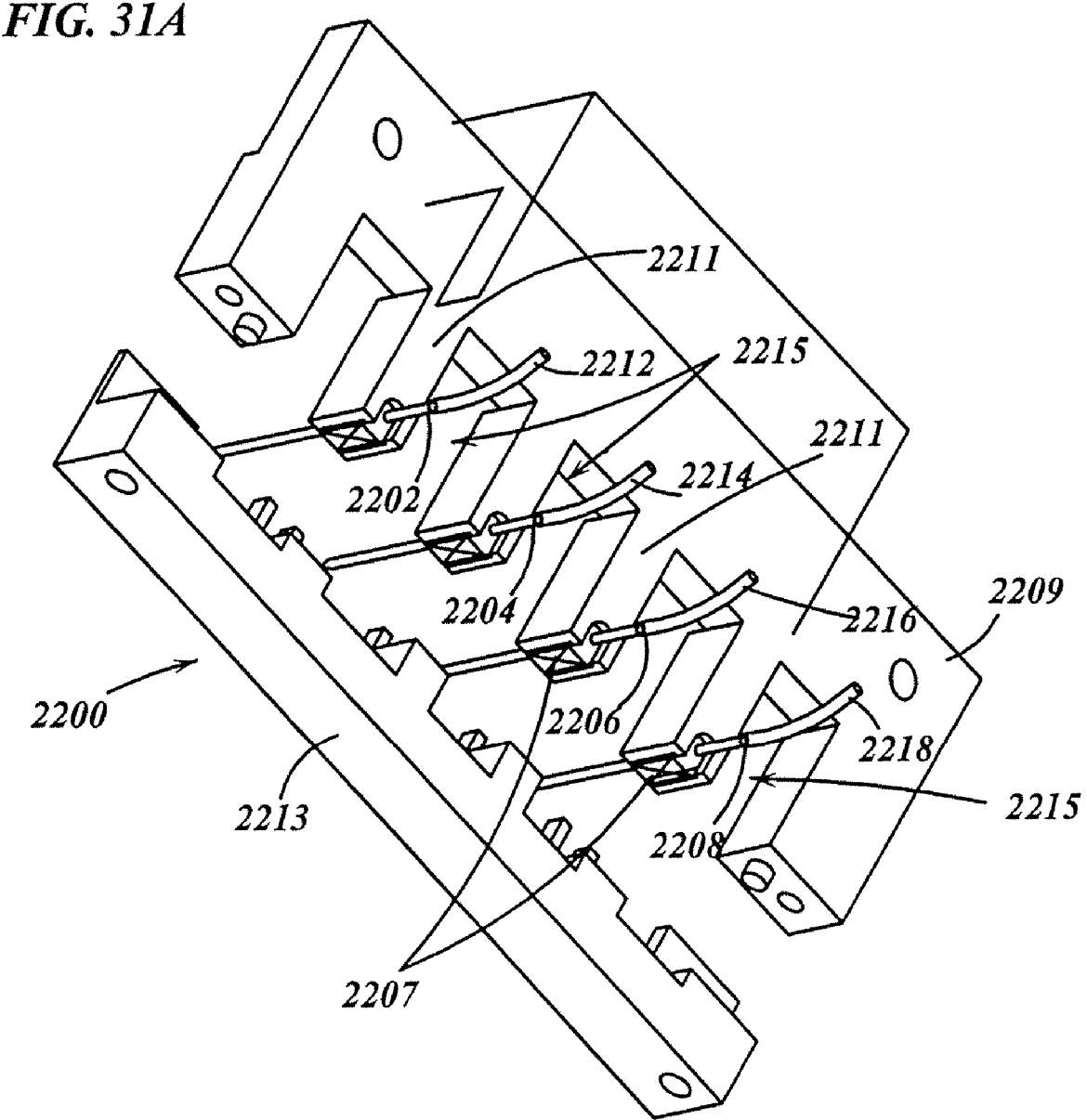
FIGS. 31A-31H are enlarged perspective views of the needle manifold of the filling unit of FIGS. 30A-30F showing progressively the movement of the needle manifold between a non-actuated position spaced above the vials, and an actuated position with the needles penetrating the respective needle penetration regions of the resealable stoppers of the vials located within the filling station for filling the interior chambers of the vials with a medicament or other substance.
Figure 31B:
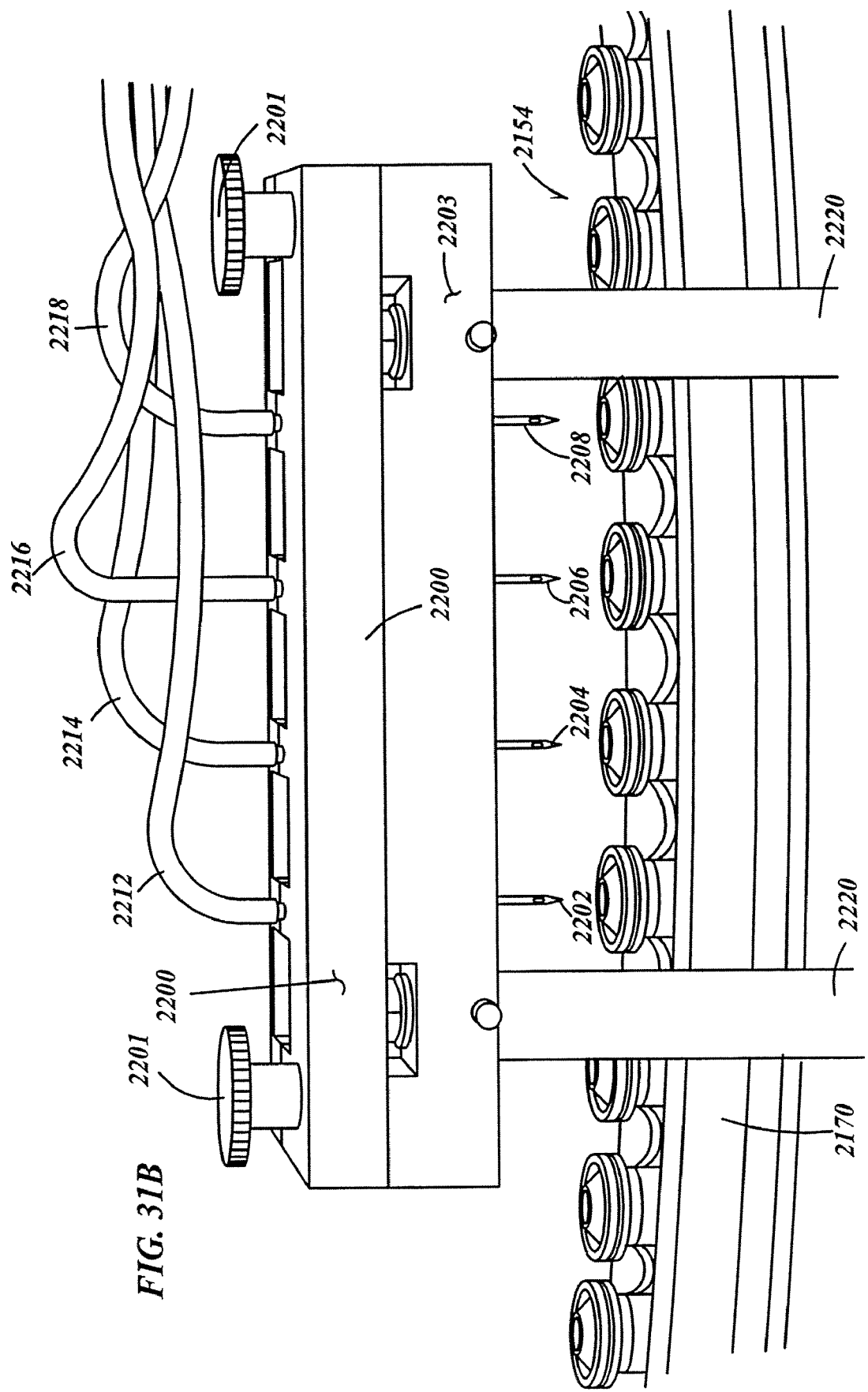
Figure 31C:
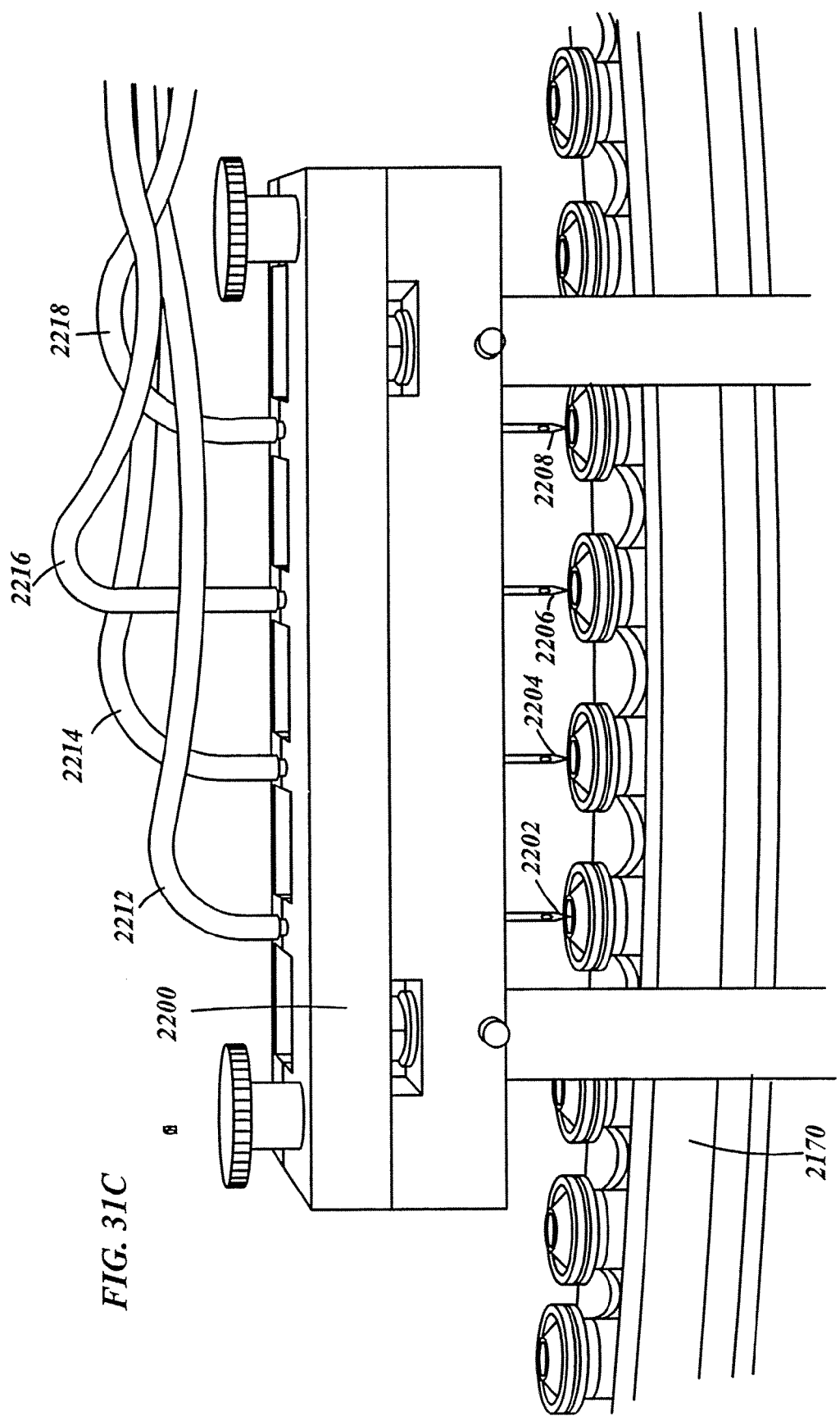
Figure 31D:
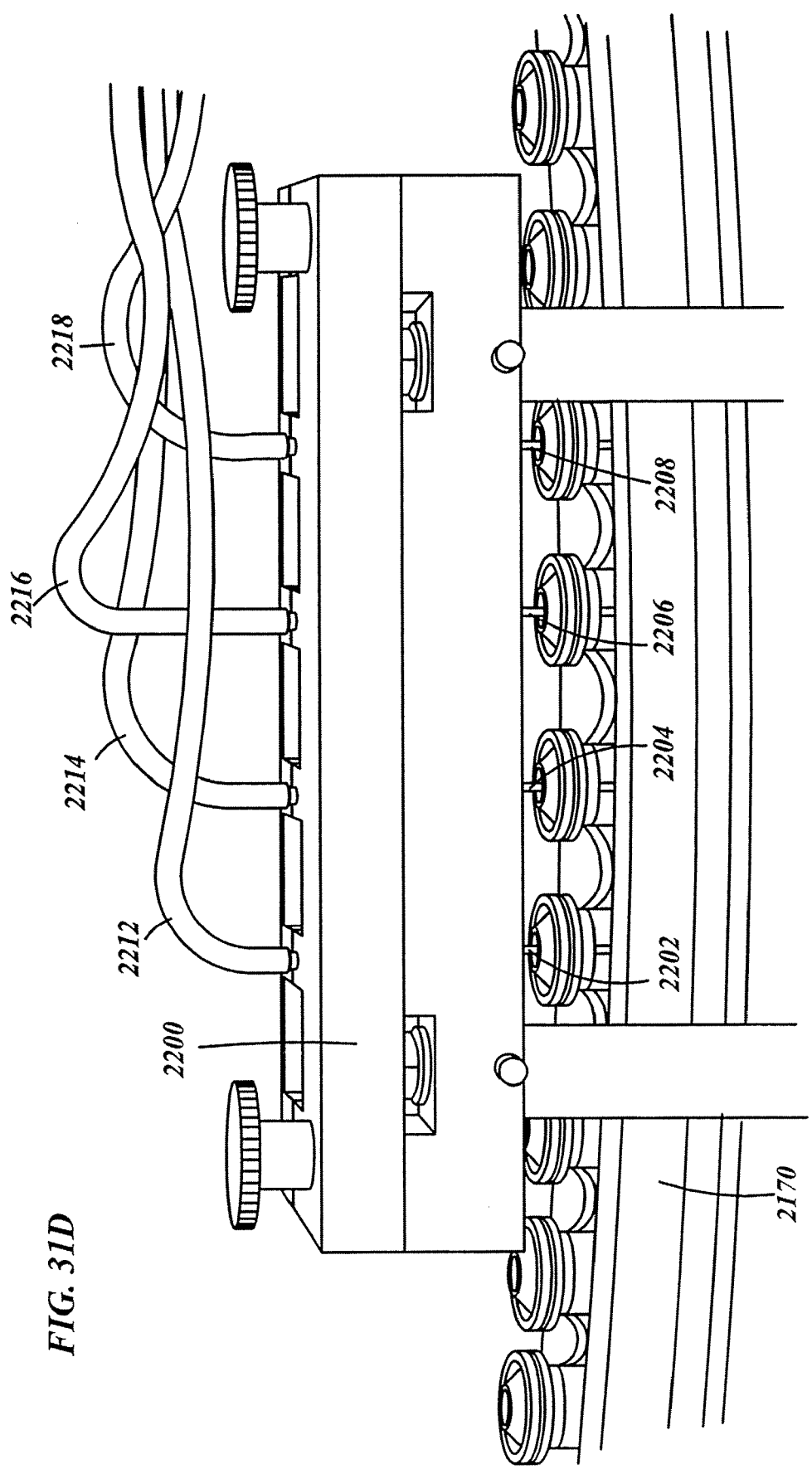
Figure 31E:
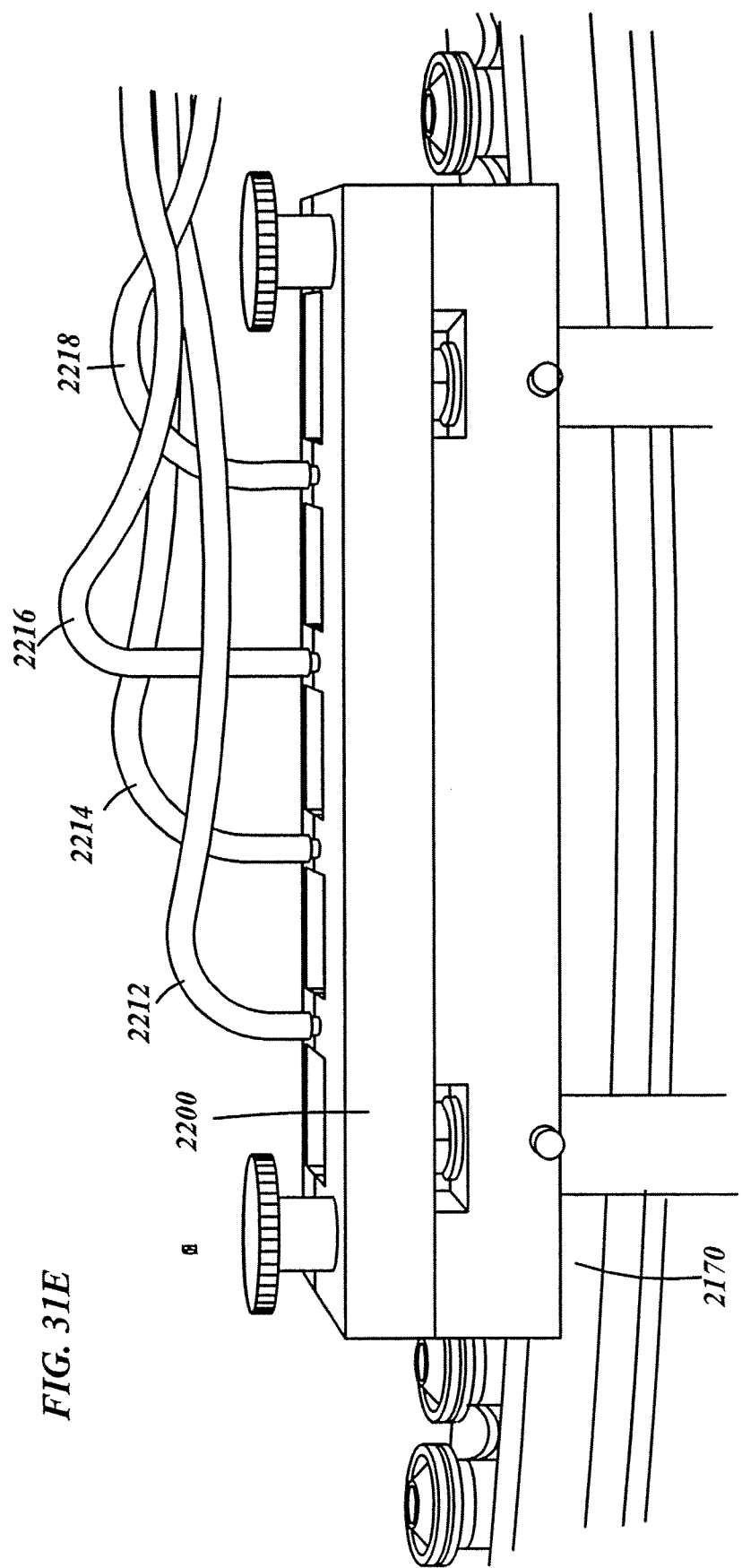
Figure 31F:
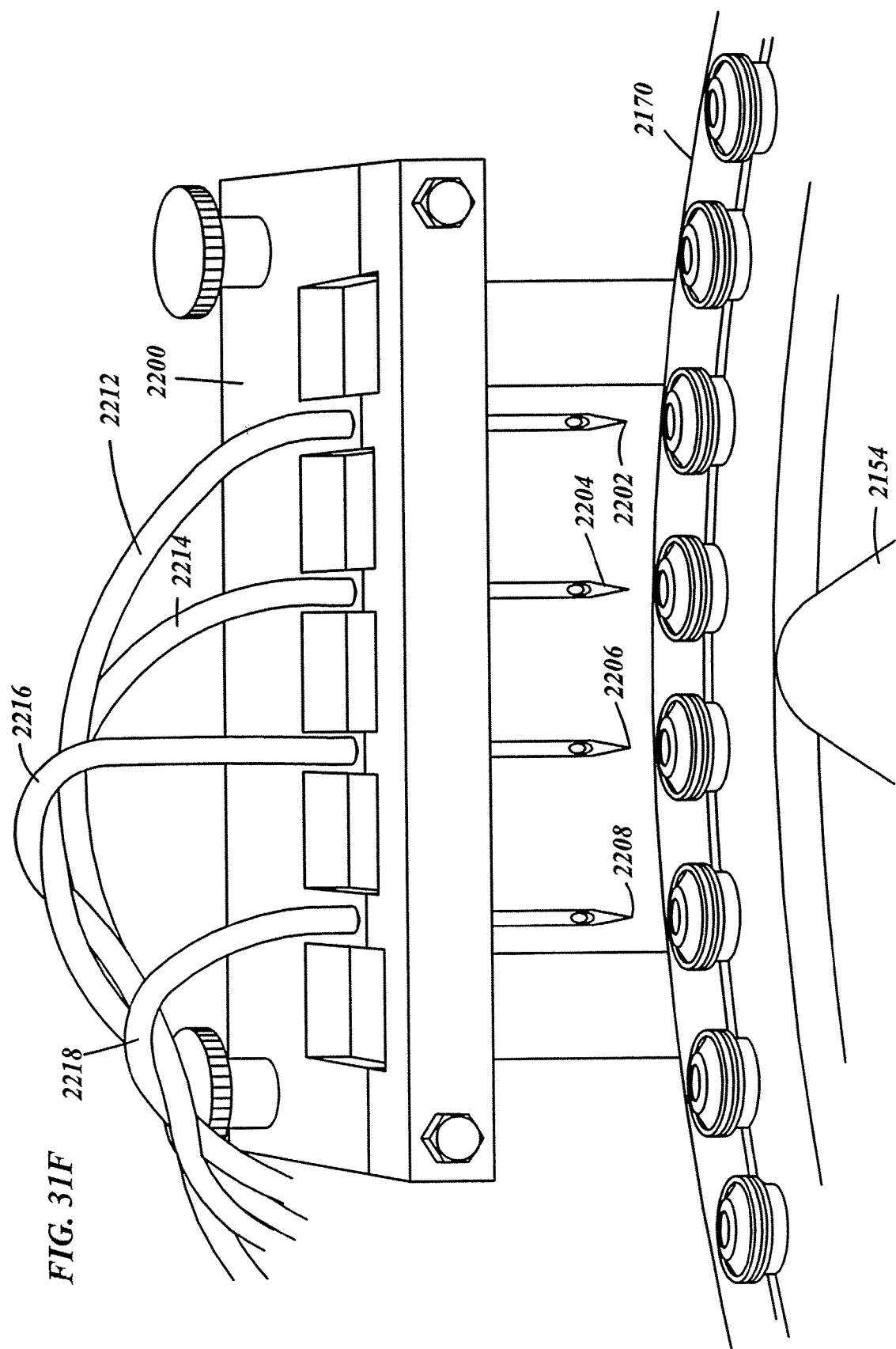
Figure 31G:
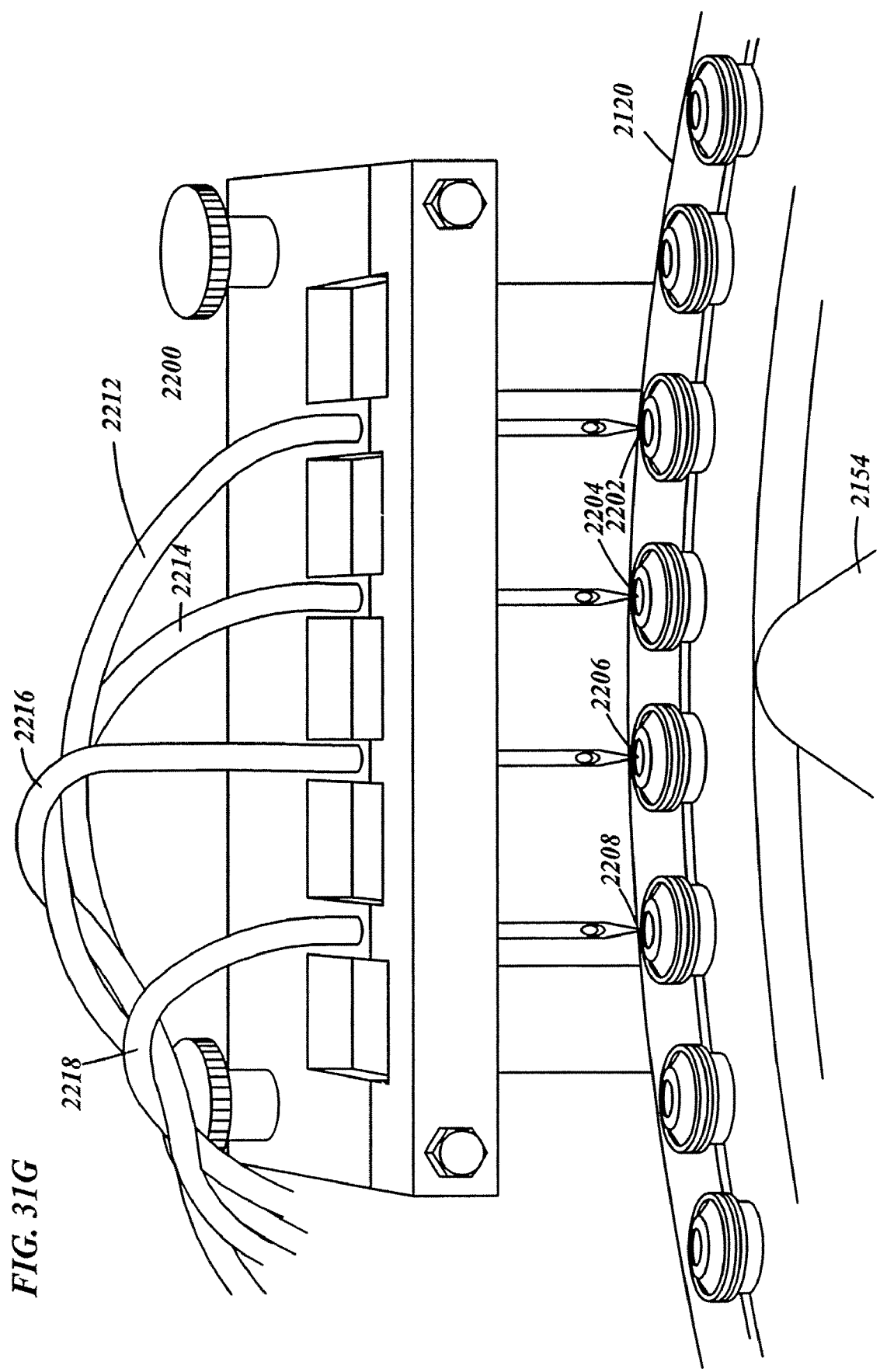
Figure 31H:
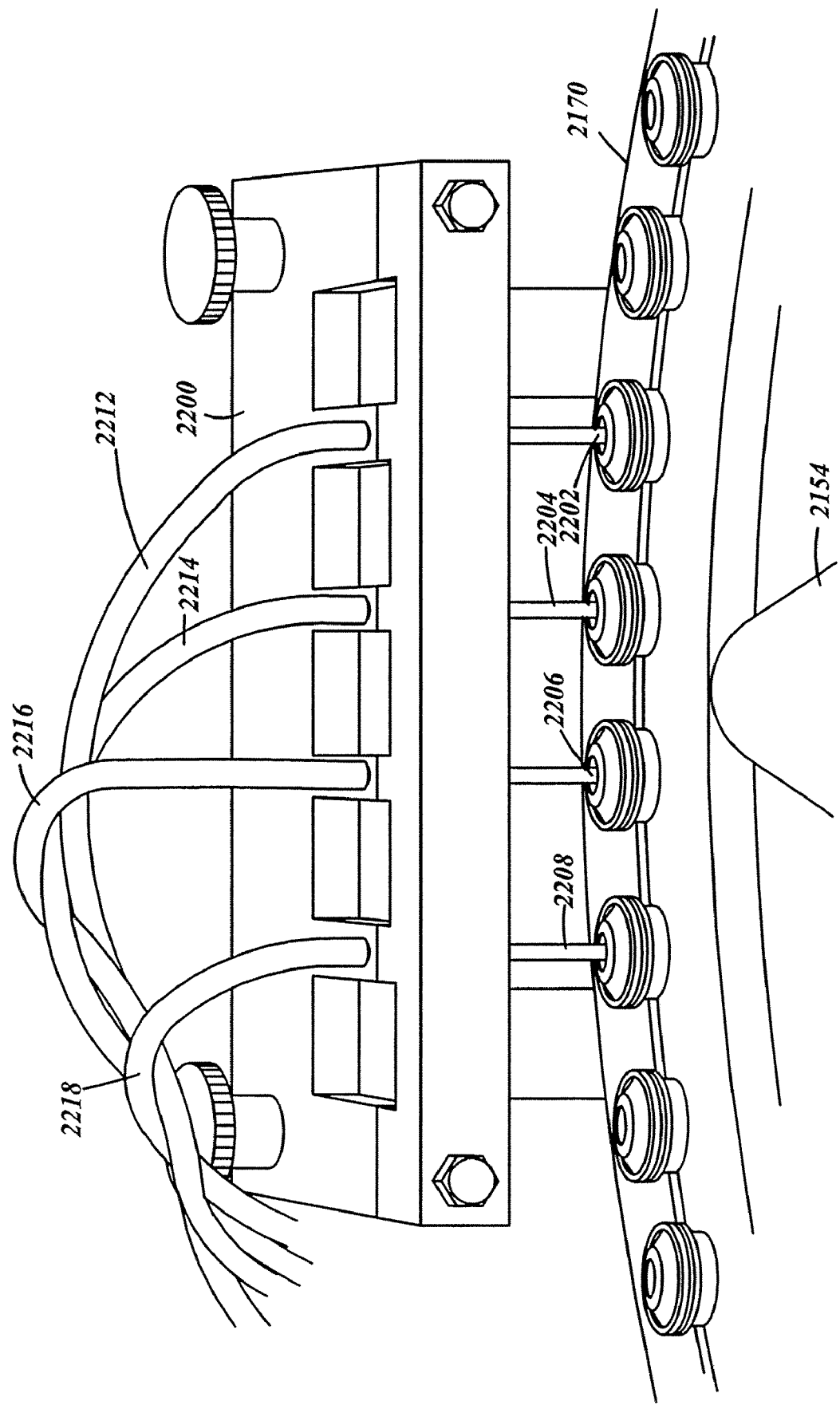
Figure 32:
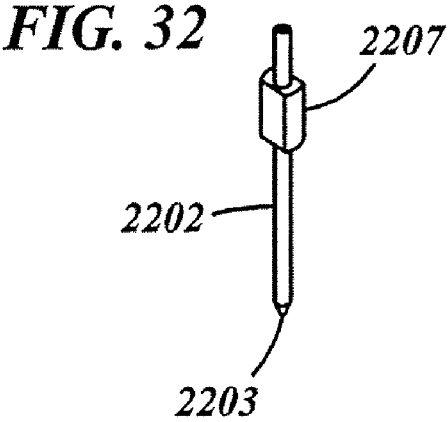
FIG. 32 is a further enlarged perspective view of an example of a needle that may be mounted in the needle manifold of FIGS. 31A-31H.
Figure 33B:
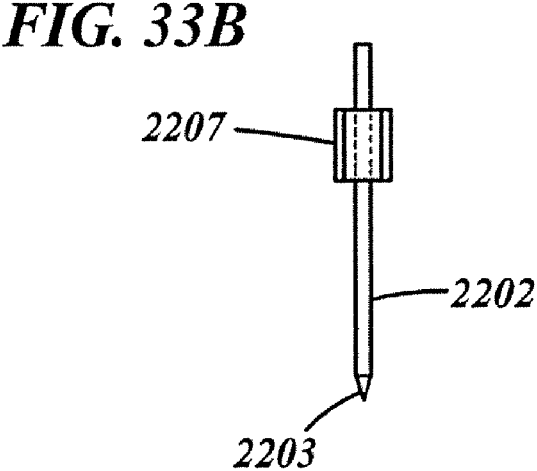
FIGS. 33A-33B are views of one embodiment of the needle of FIG. 32.
Figure 33A:
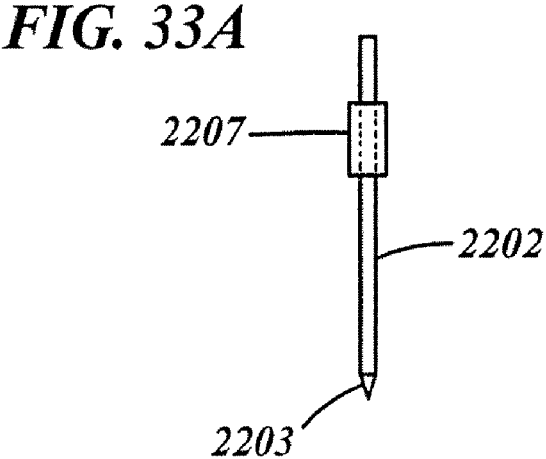

With reference to FIG. 31A and FIGS. 34 and 35, a bushing 2207 is mounted on the shank of each needle for mounting same to the needle manifold 2200. As shown in FIG. 31A, the needle manifold includes a base 2209 defining a plurality of needle mounts 2211 extending laterally therefrom and spaced relative to each other. A needle clamp 2213 is aligned on the base 2209 by alignment pins and corresponding alignments apertures, and is releasably connectable to the base 2209 by screws or like fasteners to fixedly secure the needles to the mounts. A plurality of flow apertures 2215 extend between the needle mounts to allow laminar flow over the needles and downwardly over the vials during needle filling. As shown typically in FIG. 31B, the needle manifold 2200 is releasably connectable by thumb screws 2201 to a drive plate 2203 that is, in turn, fixedly mounted to the drive shafts 2220. One advantage of this configuration is that the needle manifold (and associated filling lines) can be easily replaced without tools between fills or otherwise as required by simply turning the thumb screws.

In many embodiments, heat is generated by plunging the needles into, and extracting the needles from, the resealable caps or stoppers. In some embodiments, the medicament (or other fluid) supplied to the needles conducts heat away from the needles and thereby helps to keep the needles within a desired operating temperature range. In some of these embodiments, the medicament is cooled prior to supplying the medicament (or other fluid) to the needles. In some of these embodiments, the filling station maintains the medicament at about a predetermined temperature, below about a predetermined temperature, or about within a predetermined temperature range.

In some embodiments, the operation of the second arm 2115 is driven automatically. In some of such embodiments, the drive to the second arm may be controlled, for example, based on signals from sensors that may be employed to detect when all of the containers have been moved off of the tray. In some others of such embodiments, the second arm may be controlled for example, by a switch, actuated by an operator.

Although shown having four needles, four laser optic assemblies and four IR sensors, it should be understood that the filling station is not limited to such and may instead include some other number of needles, laser optic assemblies and IR sensors. It should also be understood that there is no absolute requirement that there be the identical numbers of needles, laser optic assemblies and IR sensors.

Thus, the filling machine may include any desired number of needles, or may be mounted or driven in any of numerous different ways that are currently, or later become known, for performing the functions of the needle filling station described herein. Moreover, the filling machine 2010 may include a plurality of needle filling stations mounted therein, in order to increase or otherwise adjust the overall throughput of the filling machine.

Although the needles are shown mounted on a single manifold, it should be understood that this is not required. For example, in some embodiments, each needle may be individually actuatable into and out of engagement with the resealable stoppers of the vials or other containers.

The drive source may take the form of any of numerous different types of drive sources that are currently, or later become known, for performing the function of the drive source as described herein, such as a pneumatic drive, or a solenoid-actuated or other type of electric drive.

In addition, it should be recognized that the infeed unit may take the form of any of numerous devices that are currently, or later become known for performing the functions of the infeed unit, such as any of numerous different types of vibratory feed drives, or "pick and place" robotic systems.

Further, the transport system is not limited to turntables and star wheels. Indeed the transport system may take the form of any of numerous different types of transport or conveyer systems that are currently, or later become known, for performing the functions of the turntable and/or star wheels described herein. For example, a transport system may take the form of a vibratory feed drive, or may take the form of an endless conveyor belt including, for example, a plurality of receptacles, such as cleats, for receiving or otherwise holding the vials at predetermined positions on the conveyor. The transport system may be drivingly connected to a motor or other suitable drive source, which is controlled by a computer or other control unit to start, stop, control the speed, and otherwise coordinate operation of the transport system with the other components of the filling machine.

Further, the rejection and discharge units need not have the forms of star wheels but rather may have the form of pick and place robots, or any of numerous other devices that are currently or later become known for performing the functions of these units described herein.

It should be understood that the filling station is not limited to the type of barrier system described above. For example, some filling stations use a barrier that provides an airtight seal around the filling station rather than vents to the outside. Some of these embodiments may nonetheless provide filtered airflow, with or without laminar flow characteristics, within the filling station. In some situations, the filling station may not need a barrier at all, but rather may be able to rely on the cleanliness of the area in which such filling machine is located.

In some embodiments, the filling machine 2010 also includes means for visually inspecting the filling station. This may take the form of a beta-barrier window, and/or a CCD, video or other camera mounted within the housing for transmitting to an external monitor images of the filling station. As may be recognized by those skilled in the pertinent art based on the teachings herein, these particular devices are only exemplary, and any of numerous other devices that are currently, or later become known, for performing the function of permitting visual inspection equally may be employed. In some embodiments, a vision system is used to inspect each laser seal. The filling station may also be equipped with a level detection system for detecting the level of fluid or other substance within each vial or other container to ensure that it is filled to the correct level, and a labeling station.

In some embodiments, once loaded onto the filling machine 2010, the vials or other containers (or at least the needle penetration surfaces thereof) are sterilized again by laser radiation as described above, or by e-beam radiation, in order to further ensure absolute sterility of the requisite surfaces prior to filling and sealing. For example, in some embodiments, the filling machine may further include an e-beam assembly comprising an e-beam source as disclosed in co-pending U.S. patent application Ser. No. 10/600,525, filed Jun. 19, 2003, or co-pending international PCT Patent Application No. PCT/US03/19656, filed Jun. 19, 2003, each of which is entitled "STERILE FILLING MACHINE HAVING NEEDLE FILLING STATION WITHIN E-BEAM CHAMBER" and is hereby expressly incorporated by reference as part of the present disclosure.

As described in these co-pending patent applications, the e-beam source may be any of numerous different types of e-beam sources that are currently, or later become known, for performing the function of the e-beam source described herein. E-beam radiation is a form of ionizing energy that is generally characterized by its low penetration and high dose rates. The electrons alter various chemical and molecular bonds upon contact with an exposed product, including the reproductive cells of microorganisms, and therefore e-beam radiation is particularly suitable for sterilizing vials, syringes and other containers for medicaments or other sterile substances. An e-beam source produces an electron beam that is formed by a concentrated, highly charged stream of electrons generated by the acceleration and conversion of electricity. Preferably, the electron beam is focused onto a penetrable surface of each container for piercing by a needle to thereby fill the container with a medicament or other substance. For example, in the case of vials, such as the vials including resealable stoppers as described above, the electron beam is focused onto the upper surface of the stopper to sterilize the penetrable surface of the stopper prior to insertion of the filling needle therethrough. In addition, reflective surfaces may be mounted on opposite sides of the conveyor relative to each other to reflect the e-beam, and/or the reflected and scattered electrons, onto the sides of the vials to sterilize these surfaces of the vial. Alternatively, or in combination with such reflective surfaces, more than one e-beam source may be employed, wherein each e-beam source is focused onto a respective surface or surface portion of the vials or other containers to ensure sterilization of each surface area of interest.

In some embodiments the current, scan width, position and energy of the e-beam, the speed of the transport system, and/or the orientation and position of any reflective surfaces, are selected to achieve at least about a 3 log reduction, and preferably about a 6 log reduction in bio-burden testing on the upper surface of the vial's resealable stopper, i.e., the surface of the stopper defining the penetrable region that is pierced by a filling needle to fill the vial. In addition, as an added measure of caution, one or more of the foregoing variables also are preferably selected to achieve at least about a 3 log reduction on the sides of the vial, i.e., on the surfaces of the vial that are not pierced by the needle during filling. These specific levels of sterility are only exemplary, however, and the sterility levels may be set as desired or otherwise required to validate a particular product under, for example, United States FDA or applicable European standards, such as the applicable Sterility Assurance Levels ("SAL"). An exemplary sterile filling machine including an e-beam unit which is adapted to needle fill within the e-beam chamber is described in the above-mentioned co-pending patent application. Further, as may be recognized by those of ordinary skill in the pertinent art based on the teachings herein, such an e-beam unit equally may be used in connection with the sterile filling machine 2010 in order to apply e-beam radiation to at least the needle penetration regions of the stoppers, to the needles during for filling, and/or to the vials or needle penetrated regions of the vials in the laser sealing station.

Except where otherwise stated, terms such as, for example, "comprises", "has", "includes", and all forms thereof, are considered open-ended, so as not to preclude additional elements and/or features.

As may be recognized by those skilled in the pertinent art based on the teachings herein, numerous changes and modifications may be made to the above-described and other embodiments without departing from its scope as defined in the appended claims. For example, the resealable member may be integrally molded with the base such as by insert molding, the resealable member may be fused or otherwise melted to the base of the stopper, or the resealable member may be sequentially molded to the base. In addition, the resealable member may be made of any of numerous different materials which are currently known, or which later become known for performing the functions of the resealable member described herein, such as any of numerous different thermoplastic and/or elastomeric materials, including, for example, low-density polyethylene. Similarly, the base of the stopper can be made of vulcanized rubber as described above, or any of numerous other materials which are currently, or later become known as being compatible with, or otherwise defining a stable enclosure for the particular medicament or other substance contained within the vial or other container. In addition, the resealable stoppers may include more than one layer of vulcanized rubber and/or more than one layer of resealable material. In addition, the cauterization and sealing stations may employ any of numerous different types of heat sources that are currently, or later become known, for performing the functions of the heat sources described herein, such as any of numerous different types of laser or other optical sources or conductive heat sources. Accordingly, this detailed description of the preferred embodiments is to be taken in an illustrative, as opposed to a limiting sense.

What is claimed is:

1. A device defining a chamber for receiving a substance and a thermoplastic portion in fluid communication with the chamber, the thermoplastic portion defining a penetrable region that is penetrable by a filling member and is heat resealable to hermetically seal an aperture therein by applying laser radiation at a predetermined wavelength and power thereto, wherein the thermoplastic portion comprises a thermoplastic body defining a predetermined wall thickness and including (i) a styrene block copolymer; (ii) an olefin; (iii) a predetermined amount of pigment that allows the body to substantially absorb laser radiation at the predetermined wavelength and substantially prevent the passage of radiation through the predetermined wall thickness, and hermetically seal the aperture in the penetrable region in a predetermined time period; and (iv) a predetermined amount of lubricant that reduces friction forces at an interface of the filling member and body during penetration thereof.

2. A device as defined in claim 1, wherein the predetermined time period is less than approximately 2 seconds.

3. A device as defined in claim 1, wherein the styrene block copolymer is within the range of about 80% to about 97% by weight.

4. A device as defined in claim 1, wherein the olefin is within the range of about 3% to about 20% by weight.

5. A device as defined in claim 1, wherein the ratio of the styrene block copolymer to the olefin is within the range of about 50:50 by weight to about 90:5 by weight.

6. A device as defined in claim 1, wherein the predetermined wavelength is approximately 980 nm and the predetermined power is less than approximately 30 Watts.

7. A device as defined in claim 1, wherein the amount of pigment is within the range of about 0.3% to about 0.6% by weight.

8. A device as defined in claim 1, wherein at least one of (i) the thermoplastic portion is a stopper, (ii) the filling member is a needle, (iii) the device is a vial; and (iv) the device is a syringe.

9. A device as defined in claim 1, wherein the lubricant is selected from the group including silicone, mineral oil, and silicone oil.

10. A device as defined in claim 1, wherein the amount of lubricant is within the range of about 0.4% to about 0.6% by weight.

11. A device as defined in claim 1, in combination with a filling member for penetrating the thermoplastic portion, wherein the filling member includes a non-coring, conically-pointed tip.

12. A device and filling member as defined in claim 11, wherein the filling member includes a low-friction coating for reducing friction forces between the filling member and the thermoplastic portion during penetration thereof.

13. A device and filling member as defined in claim 11, wherein the low-friction coating is at least one of tungsten carbide and titanium.

14. A device and filling member as defined in claim 11, wherein the filling member is a needle.

15. A method comprising the following steps:
providing a device including a body defining a chamber for receiving a substance and a thermoplastic portion in fluid communication with the chamber, wherein the thermoplastic portion includes a styrene block copolymer and an olefin, and defines a penetrable region that is penetrable by a filling member and is heat resealable to hermetically seal an aperture therein by applying laser radiation at a predetermined wavelength and power thereto;

providing the thermoplastic portion with a predetermined amount of pigment that allows the penetrable region to substantially absorb laser radiation at the predetermined wavelength and substantially prevent the passage of radiation through the predetermined wall thickness thereof;

providing a filling member defining a non-coring, conically-pointed tip and at least one flow aperture located adjacent to the tip and connectable in fluid communication with a source of substance;

penetrating the penetrable region of the thermoplastic portion with the conically-pointed tip of the filling member such that the flow aperture of the filling member is in fluid communication with the chamber of the device;

providing a lubricant at the interface of the filling member and thermoplastic portion to reduce friction forces therebetween;

introducing the substance through the filling member and into the chamber of the device;

withdrawing the filling member from the thermoplastic portion; and transmitting laser radiation at the predetermined wavelength and power onto an aperture formed in the penetrable region of the thermoplastic portion, and hermetically sealing the aperture within a time period of less than about 2 seconds.

16. A method as defined in claim 15, wherein the step of providing a lubricant includes providing a lubricant within the thermoplastic portion that reduces friction forces at the interface of the filling member and thermoplastic portion.

17. A method as defined in claim 15, further comprising the steps of molding the thermoplastic portion and body from plastic under a substantially laminar flow; and prior to allowing the thermoplastic portion and body to cool to an ambient temperature, assembling the thermoplastic portion and body and, in turn, forming a sterile chamber sealed with respect to ambient atmosphere.

18. A method as defined in claim 15, further comprising the step of transmitting e-beam radiation onto the surface of the filling member prior to penetrating the thermoplastic portion therewith.

19. A method as defined in claim 15, further comprising the step of transmitting e-beam radiation onto the thermoplastic portion during laser sealing thereof.

20. A method as defined in claim 15, wherein the step of introducing includes introducing at least one of a medicament, cosmetic and a food product.

21. A method as defined in claim 15, further comprising the step of sterilizing the sealed empty device prior to introducing the substance.

* * * * *